United States Patent
Park et al.

(10) Patent No.: US 8,940,768 B2
(45) Date of Patent: Jan. 27, 2015

(54) ANTIFUNGAL TRIAZOLE DERIVATIVES

(75) Inventors: Joon Seok Park, Yongin-si (KR); Kyung A Yu, Suwon-si (KR); Yun Soo Yoon, Seoul (KR); Mi Ryeong Han, Anyang-si (KR); Ji Duck Kim, Yongin-si (KR)

(73) Assignee: Daewoong Pharmaceutical Co., Ltd., Sungnam-si (KR)

( * ) Notice: Subject to any disclaimer, the term of this patent is extended or adjusted under 35 U.S.C. 154(b) by 112 days.

(21) Appl. No.: 13/578,590

(22) PCT Filed: Feb. 11, 2011

(86) PCT No.: PCT/KR2011/000925
§ 371 (c)(1),
(2), (4) Date: Aug. 10, 2012

(87) PCT Pub. No.: WO2011/099804
PCT Pub. Date: Aug. 18, 2011

(65) Prior Publication Data
US 2012/0309771 A1 Dec. 6, 2012

(30) Foreign Application Priority Data
Feb. 12, 2010 (KR) .................. 10-2010-0013608

(51) Int. Cl.
*A61K 31/4196* (2006.01)
*C07D 401/12* (2006.01)
*C07D 401/14* (2006.01)
*C07D 401/06* (2006.01)

(52) U.S. Cl.
CPC .......... *C07D 401/14* (2013.01); *A61K 31/4196* (2013.01); *C07D 401/06* (2013.01); *C07D 401/12* (2013.01)
USPC ........... 514/326; 514/256; 514/318; 544/333; 546/194; 546/210

(58) Field of Classification Search
CPC ............. A61K 31/4196; C07D 401/06; C07D 401/12; C07D 401/14
USPC ........... 514/256, 318, 326; 544/333; 546/194, 546/210
See application file for complete search history.

(56) References Cited

U.S. PATENT DOCUMENTS 5,389,663 A * 2/1995 Itoh et al. ................. 514/383
7,973,056 B2 * 7/2011 Nagayama ................. 514/318

FOREIGN PATENT DOCUMENTS

| CN | 001324792 A | 12/2001 |
| CN | 101781263 | * 7/2010 |
| WO | 01/89447 A2 | 11/2001 |
| WO | 2005/014583 A1 | 2/2005 |

OTHER PUBLICATIONS

Wang et al. "Novel conformationally . . . " Eur. J. Med. Chem. v.45 p. 6020-6026 (2010).*
Patani et. al. "Bioisosterism: a rational . . . " Chem. Rev. 96, 3147-3176 (1996).*
Zhao "Synthesis and antifungal . . . " Chinese J. Med. Chem. v.16(3)p. 150-153 (2006).*
Zhao et al. "Synthesis of . . . " CA149:448290 (2007).*
Chai et al., "Design, synthesis, and biological evaluation of novel triazole derivatives as inhibitors of cytochrome P450 14α-demethylase," *European Journal of Medicinal Chemistry* 44(5):1913-1920, 2009.
Dan et al., "Design and synthesis of novel triazole antifungal derivatives based on the active site of fungal lanosterol 14a-demethylase (CYP51)," *Chinese Chemical Letters* 20(8):935-938, 2009.
Lebouvier et al., "Synthesis and antifungal activities of new fluconazole analogues with azaheterocycle moiety," *Bioorganic & Medicinal Chemistry Letters* 17(13):3686-3689, 2007.
Liu et al., "Synthesis and SAR studies of biaryloxy-substituted triazoles as antifungal agents," *Bioorganic & Medicinal Chemistry Letters* 18(11):3261-3265, 2008.
Wang et al., "Discovery of highly potent novel antifungal azoles by structure-based rational design," *Bioorganic & Medicinal Chemistry Letters* 19(20):5965-5969, 2009.
Wang et al., "Design, Synthesis, and Antifungal Activity of Novel Conformationally Restricted Triazole Derivatives," *Arch. Pharm. Chem. Life Sci.* 342(12):732-739, 2009.
Zhao et al., "Design, Synthesis, and Antifungal Activities of Novel 1*H*-Triazole Derivatives Based on the Structure of the Active Site of Fungal Lanosterol α-Demethylase (CYP51)," *Chemistry & Biodiversity* 4(7):1472-1479, 2007.

\* cited by examiner

*Primary Examiner* — Celia Chang
(74) *Attorney, Agent, or Firm* — Seed IP Law Group PLLC

(57) ABSTRACT

Disclosed are novel triazole derivatives. Exhibiting excellent antifungal activity and in vivo safety, they are useful for the treatment or prevention of fungal infections caused by a wide spectrum of fungi.

18 Claims, No Drawings

ANTIFUNGAL TRIAZOLE DERIVATIVES

CROSS-REFERENCES TO RELATED APPLICATION

This application is a U.S. national stage application filed under 35 U.S.C. §371 of International Patent Application No. PCT/KR2011/000925 accorded an international filing date of Feb. 11, 2011, which application claims priority to Korean (KR) Patent Application No. 10-2010-0013608, filed Feb. 12, 2010, all which applications are incorporated herein by reference in their entirety.

TECHNICAL FIELD

The present invention relates to a novel antifungal triazole derivative, a preparation method thereof, an antifungal composition comprising the same, and the use thereof in the treatment or prevention of infectious fungal diseases.

BACKGROUND ART

In most cases, immuno-deficient patients such as cancer patients undergoing chemotherapy, transplant recipients, AIDS patients, etc. are concerned about fungal infections which are caused by opportunistic pathogens such as *Candida* spp., *Aspergillus* spp. and *Cryptococcus neoformans*. Commercially available anti-fungal agents in current use, however, suffer from the disadvantage of being toxic and showing inhibitory activity against only a narrow spectrum of fungi. With the recent progression of an increase in the population of immune-deficient patients, there has been an increasing demand on antifungal agents that can inhibit a wide spectrum of fungi and exhibit excellent pharmacokinetic properties. To meet the demand, a variety of antifungal compounds therapeutic for fungus-infected mammals including humans are under development and study.

Triazole derivatives which can be orally administered were reported as antifungal agents used for the treatment or prevention of fungal infections in the late 1980s. Representative examples include fluconazole consisting of 5-membered rings (UK Patent No. 2099818), and itraconazole (U.S. Pat. No. 4,267,179). In addition, triazole compounds with hetero ring substituents are disclosed in European patent No. 440372 characterized by the 6-membered pyrimidine voriconazole, in European Patent No. 241232 (Shionogi Co.) characterized by the five-membered ring isoxazole, and in European Patent No. 659751 (Takeda Co.) characterized by triazolone. Further, U.S. Pat. No. 5,716,969 (Kaken), US Patent Publication No. 2009/0299071 (Fujifilm Fine-chemicals Co.), *Bioorganic Medicinal Chemistry Letter* 201020 2942-2945) and *Archiv der Pharmazie* 2009342: 732-739 (Second Military Medical University) discloses piperidine, and WO 01/89447 (Second Military Medical University) discloses triazole derivatives with piperidine rings.

However, these conventional compounds are not sufficient as medications in terms of antifungal activity against some pathogenic opportunistic fungi which occasionally cause fatal infections in immune suppressed patients, in terms of safety and in terms of in vivo pharmacokinetics. Therefore, there is a need for compounds that are higher in biosafety and which have greater in vivo absorptivity and have more potential antifungal activity as therapeutics of mycosis.

DISCLOSURE OF INVENTION

Technical Problem

It is therefore an object of the present invention to provide a novel triazole compound which has excellent antifungal activity and in vivo safety, or a pharmaceutically acceptable salt thereof.

It is another object of the present invention to provide a method for the preparation of the compound.

It is a further object of the present invention to provide an antifungal composition comprising the compound as an active ingredient.

Solution to Problem

In order to accomplish the above objects, there is provided a compound represented by the following Chemical Formula 1, or a pharmaceutically acceptable salt thereof:

[Chemical Formula 1]

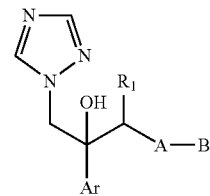

wherein,
Ar is phenyl which is substituted with one to five halogens;
A is

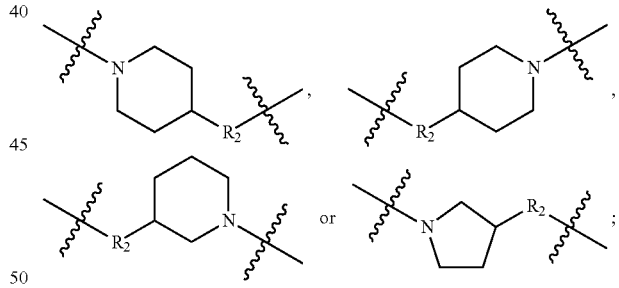

B is phenyl, pyridinyl or pyrimidinyl, which is unsubstituted or substituted with one or two $R_3$ groups;
$R_1$ is hydrogen or $C_{1-4}$ alkyl;
$R_2$ is O, NH or $NCH_3$ and
$R_3$ is independently halogen, $C_{1-4}$ alkyl, $C_{1-4}$ haloalkyl or cyano.

In Chemical Formula 1, preferably, B is pyridinyl which is unsubstituted or substituted with one or two $R_3$ group, and $R_3$ is independently halogen, $C_{1-4}$ alkyl or $C_{1-4}$ haloalkyl.

In a preferred embodiment, B is pyrimidinyl which is unsubstituted or substituted with one $R_3$ group, wherein $R_3$ is a halogen, $C_{1-4}$ alkyl or $C_{1-4}$ haloalkyl.

In another preferred embodiment, B is a phenyl which is unsubstituted or substituted with one or two $R_3$ groups, and $R_2$ is $NCH_3$.

In accordance with a further preferred embodiment, B is phenyl, pyridinyl or pyrimidinyl, which is substituted with two $R_3$ groups, and one of the two $R_3$ groups is halogen, and the other is halogen, $C_{1-4}$alkyl or $C_{1-4}$ haloalkyl or one of the two $R_3$ groups is $C_{1-4}$ alkyl and the other is $C_{1-4}$ haloalkyl.

In still a further preferred embodiment, $R_3$ is F, Cl, Br, methyl, trifluoromethyl or cyano.

In still a further preferred embodiment, Ar is phenyl which is substituted with two halogen, more preferably Ar is 2,4-difluorophenyl.

Examples of the compound useful in the present invention include:

1) (2R,3R)-2-(2,4-difluorophenyl)-3-(4-(4-fluorophenoxy)piperidin-1-yl)-1-(1H-1,2,4-triazol-1-yl)butan-2-ol,
2) (2R,3R)-2-(2,4-difluorophenyl)-3-(4-phenoxypiperidin-1-yl)-1-(1H-1,2,4-triazol-1-yl)butan-2-ol,
3) (2R,3R)-2-(2,4-difluorophenyl)-3-(4-(2-fluorophenoxy)piperidin-1-yl)-1-(1H-1,2,4-triazol-1-yl)butan-2-ol,
4) (2R,3R)-2-(2,4-difluorophenyl)-3-(4-(3-fluorophenoxy)piperidin-1-yl)-1-(1H-1,2,4-triazol-1-yl)butan-2-ol,
5) (2R,3R)-3-(4-(2-chlorophenoxy)piperidin-1-yl)-2-(2,4-difluorophenyl)-1-(1H-1,2,4-triazol-1-yl)butan-2-ol,
6) (2R,3R)-3-(4-(3-chlorophenoxy)piperidin-1-yl)-2-(2,4-difluorophenyl)-1-(1H-1,2,4-triazol-1-yl)butan-2-ol,
7) (2R,3R)-3-(4-(4-chlorophenoxy)piperidin-1-yl)-2-(2,4-difluorophenyl)-1-(1H-1,2,4-triazol-1-yl)butan-2-ol,
8) (2R,3R)-3-(4-(2-bromophenoxy)piperidin-1-yl)-2-(2,4-difluorophenyl)-1-(1H-1,2,4-triazol-1-yl)butan-2-ol,
9) (2R,3R)-3-(4-(3-bromophenoxy)piperidin-1-yl)-2-(2,4-difluorophenyl)-1-(1H-1,2,4-triazol-1-yl)butan-2-ol,
10) (2R,3R)-3-(4-(4-bromophenoxy)piperidin-1-yl)-2-(2,4-difluorophenyl)-1-(1H-1,2,4-triazol-1-yl)butan-2-ol,
11) (2R,3R)-2-(2,4-difluorophenyl)-1-(1H-1,2,4-triazol-1-yl)-3-(4-(2-(trifluoromethyl)phenoxy)piperidin-1-yl)butan-2-ol,
12) (2R,3R)-2-(2,4-difluorophenyl)-1-(1H-1,2,4-triazol-1-yl)-3-(4-(3-(trifluoromethyl)phenoxy)piperidin-1-yl)butan-2-ol,
13) (2R,3R)-2-(2,4-difluorophenyl)-1-(1H-1,2,4-triazol-1-yl)-3-(4-(4-(trifluoromethyl)phenoxy)piperidin-1-yl)butan-2-ol,
14) 2-((1-((2R,3R)-3-(2,4-difluorophenyl)-3-hydroxy-4-(1H-1,2,4-triazol-1-yl)butan-2-yl)piperidin-4-yl)oxy)benzonitrile,
15) 3-((1-((2R,3R)-3-(2,4-difluorophenyl)-3-hydroxy-4-(1H-1,2,4-triazol-1-yl)butan-2-yl)piperidin-4-yl)oxy)benzonitrile,
16) 4-((1-((2R,3R)-3-(2,4-difluorophenyl)-3-hydroxy-4-(1H-1,2,4-triazol-1-yl)butan-2-yl)piperidin-4-yl)oxy)benzonitrile,
17) (2R,3R)-3-(4-(2,4-dichlorophenoxy)piperidin-1-yl)-2-(2,4-difluorophenyl)-1-(1H-1,2,4-triazol-1-yl)butan-2-ol,
18) (2R,3R)-3-(4-(3,4-dichlorophenoxy)piperidin-1-yl)-2-(2,4-difluorophenyl)-1-(1H-1,2,4-triazol-1-yl)butan-2-ol,
19) (2R,3R)-3-(4-(4-chloro-2-fluorophenoxy)piperidin-1-yl)-2-(2,4-difluorophenyl)-1-(1H-1,2,4-triazol-1-yl)butan-2-ol,
20) (2R,3R)-3-(4-(2,4-difluorophenoxy)piperidin-1-yl)-2-(2,4-difluorophenyl)-1-(1H-1,2,4-triazol-1-yl)butan-2-ol,
21) (2R,3R)-3-(4-(4-chloro-3-fluorophenoxy)piperidin-1-yl)-2-(2,4-difluorophenyl)-1-(1H-1,2,4-triazol-1-yl)butan-2-ol,
22) (2R,3R)-3-(4-(4-chloro-2-methylphenoxy)piperidin-1-yl)-2-(2,4-difluorophenyl)-1-(1H-1,2,4-triazol-1-yl)butan-2-ol,
23) (2R,3R)-2-(2,4-difluorophenyl)-3-(4-(pyridin-2-yloxy)piperidin-1-yl)-1-(1H-1,2,4-triazol-1-yl)butan-2-ol,
24) (2R,3R)-2-(2,4-difluorophenyl)-3-(4-((5-methylpyridin-2-yl)oxy)piperidin-1-yl)-1-(1H-1,2,4-triazol-1-yl)butan-2-ol,
25) (2R,3R)-2-(2,4-difluorophenyl)-3-(4-((5-fluoropyridin-2-yl)oxy)piperidin-1-yl)-1-(1H-1,2,4-triazol-1-yl)butan-2-ol,
26) (2R,3R)-3-(4-((5-chloropyridin-2-yl)oxy)piperidin-1-yl)-2-(2,4-difluorophenyl)-1-(1H-1,2,4-triazol-1-yl)butan-2-ol,
27) (2R,3R)-2-(2,4-difluorophenyl)-1-(1H-1,2,4-triazol-1-yl)-3-(4-((5-(trifluoromethyl)pyridin-2-yl)oxy)piperidin-1-yl)butan-2-ol,
28) (2R,3R)-3-(4-((3-chloro-5-(trifluoromethyl)pyridin-2-yl)oxy)piperidin-1-yl)-2-(2,4-difluorophenyl)-1-(1H-1,2,4-triazol-1-yl)butan-2-ol,
29) (2R,3R)-2-(2,4-difluorophenyl)-3-(4-(pyrimidin-2-yloxy)piperidin-1-yl)-1-(1H-1,2,4-triazol-1-yl)butan-2-ol,
30) (2R,3R)-2-(2,4-difluorophenyl)-3-(4-((5-fluoropyrimidin-2-yl)oxy)piperidin-1-yl)-1-(1H-1,2,4-triazol-1-yl)butan-2-ol,
31) (2R,3R)-3-(4-((5-chloropyrimidin-2-yl)oxy)piperidin-1-yl)-2-(2,4-difluorophenyl)-1-(1H-1,2,4-triazol-1-yl)butan-2-ol,
32) (2R,3R)-3-(4-((5-bromopyrimidin-2-yl)oxy)piperidin-1-yl)-2-(2,4-difluorophenyl)-1-(1H-1,2,4-triazol-1-yl)butan-2-ol,
33) (2R,3R)-2-(2,4-difluorophenyl)-3-(4-((5-methylpyrimidin-2-yl)oxy)piperidin-1-yl)-1-(1H-1,2,4-triazol-1-yl)butan-2-ol,
34) (2R,3R)-3-(4-((4-chlorophenyl)amino)piperidin-1-yl)-2-(2,4-difluorophenyl)-1-(1H-1,2,4-triazol-1-yl)butan-2-ol,
35) (2R,3R)-2-(2,4-difluorophenyl)-3-(4-(phenylamino)piperidin-1-yl)-1-(1H-1,2,4-triazol-1-yl)butan-2-ol,
36) (2R,3R)-2-(2,4-difluorophenyl)-3-(4-((2-fluorophenyl)amino)piperidin-1-yl)-1-(1H-1,2,4-triazol-1-yl)butan-2-ol,
37) (2R,3R)-2-(2,4-difluorophenyl)-3-(4-((3-fluorophenyl)amino)piperidin-1-yl)-1-(1H-1,2,4-triazol-1-yl)butan-2-ol,
38) (2R,3R)-2-(2,4-difluorophenyl)-3-(4-((4-fluorophenyl)amino)piperidin-1-yl)-1-(1H-1,2,4-triazol-1-yl)butan-2-ol,
39) (2R,3R)-3-(4-((2-chlorophenyl)amino)piperidin-1-yl)-2-(2,4-difluorophenyl)-1-(1H-1,2,4-triazol-1-yl)butan-2-ol,
40) (2R,3R)-3-(4-((3-chlorophenyl)amino)piperidin-1-yl)-2-(2,4-difluorophenyl)-1-(1H-1,2,4-triazol-1-yl)butan-2-ol,
41) (2R,3R)-3-(4-((2-bromophenyl)amino)piperidin-1-yl)-2-(2,4-difluorophenyl)-1-(1H-1,2,4-triazol-1-yl)butan-2-ol,
42) (2R,3R)-3-(4-((3-bromophenyl)amino)piperidin-1-yl)-2-(2,4-difluorophenyl)-1-(1H-1,2,4-triazol-1-yl)butan-2-ol,
43) (2R,3R)-3-(4-((4-bromophenyl)amino)piperidin-1-yl)-2-(2,4-difluorophenyl)-1-(1H-1,2,4-triazol-1-yl)butan-2-ol,
44) (2R,3R)-2-(2,4-difluorophenyl)-1-(1H-1,2,4-triazol-1-yl)-3-(4-((2-(trifluoromethyl)phenyl)amino)piperidin-1-yl)butan-2-ol,
45) (2R,3R)-2-(2,4-difluorophenyl)-1-(1H-1,2,4-triazol-1-yl)-3-(4-((3-(trifluoromethyl)phenyl)amino)piperidin-1-yl)butan-2-ol, 46) (2R,3R)-2-(2,4-difluorophenyl)-1-(1H-1,2,4-triazol-1-yl)-3-(4-((4-(trifluoromethyl)phenyl)amino)piperidin-1-yl)butan-2-ol,
47) 2-((1-((2R,3R)-3-(2,4-difluorophenyl)-3-hydroxy-4-(1H-1,2,4-triazol-1-yl)butan-2-yl)piperidin-4-yl)amino)benzonitrile,
48) 3-((1-((2R,3R)-3-(2,4-difluorophenyl)-3-hydroxy-4-(1H-1,2,4-triazol-1-yl)butan-2-yl)piperidin-4-yl)amino)benzonitrile,
49) 4-((1-((2R,3R)-3-(2,4-difluorophenyl)-3-hydroxy-4-(1H-1,2,4-triazol-1-yl)butan-2-yl)piperidin-4-yl)amino)benzonitrile,
50) (2R,3R)-3-(4-((2,4-dichlorophenyl)amino)piperidin-1-yl)-2-(2,4-difluorophenyl)-1-(1H-1,2,4-triazol-1-yl)butan-2-ol,
51) (2R,3R)-3-(4-((3,4-dichlorophenyl)amino)piperidin-1-yl)-2-(2,4-difluorophenyl)-1-(1H-1,2,4-triazol-1-yl)butan-2-ol,
52) (2R,3R)-3-(4-((4-chloro-2-fluorophenyl)amino)piperidin-1-yl)-2-(2,4-difluorophenyl)-1-(1H-1,2,4-triazol-1-yl)butan-2-ol,
53) (2R,3R)-2-(2,4-difluorophenyl)-3-(4-((2,4-difluorophenyl)amino)piperidin-1-yl)-1-(1H-1,2,4-triazol-1-yl)butan-2-ol,
54) (2R,3R)-3-(4-((4-chloro-3-fluorophenyl)amino)piperidin-1-yl)-2-(2,4-difluorophenyl)-1-(1H-1,2,4-triazol-1-yl)butan-2-ol,
55) (2R,3R)-3-(4-((4-chloro-2-methylphenyl)amino)piperidin-1-yl)-2-(2,4-difluorophenyl)-1-(1H-1,2,4-triazol-1-yl)butan-2-ol,
56) (2R,3R)-2-(2,4-difluorophenyl)-3-(4-(pyridin-2-ylamino)piperidin-1-yl)-1-(1H-1,2,4-triazol-1-yl)butan-2-ol,
57) (2R,3R)-2-(2,4-difluorophenyl)-3-(4-((5-methylpyridin-2-yl)amino)piperidin-1-yl)-1-(1H-1,2,4-triazol-1-yl)butan-2-ol,
58) (2R,3R)-2-(2,4-difluorophenyl)-3-(4-((5-fluoropyridin-2-yl)amino)piperidin-1-yl)-1-(1H-1,2,4-triazol-1-yl)butan-2-ol,
59) (2R,3R)-3-(4-((5-chloropyridin-2-yl)amino)piperidin-1-yl)-2-(2,4-difluorophenyl)-1-(1H-1,2,4-triazol-1-yl)butan-2-ol,
60) (2R,3R)-3-(4-((3-chloro-5-(trifluoromethyl)pyridin-2-yl)amino)piperidin-1-yl)-2-(2,4-difluorophenyl)-1-(1H-1,2,4-triazol-1-yl)butan-2-ol,
61) (2R,3R)-2-(2,4-difluorophenyl)-1-(1H-1,2,4-triazol-1-yl)-3-(4-((5-(trifluoromethyl)pyridin-2-yl)amino)piperidin-1-yl)butan-2-ol,
62) (2R,3R)-2-(2,4-difluorophenyl)-3-(4-(pyrimidin-2-ylamino)piperidin-1-yl)-1-(1H-1,2,4-triazol-1-yl)butan-2-ol,
63) (2R,3R)-2-(2,4-difluorophenyl)-3-(4-((5-fluoropyrimidin-2-yl)amino)piperidin-1-yl)-1-(1H-1,2,4-triazol-1-yl)butan-2-ol,
64) (2R,3R)-3-(4-((5-bromopyrimidin-2-yl)amino)piperidin-1-yl)-2-(2,4-difluorophenyl)-1-(1H-1,2,4-triazol-1-yl)butan-2-ol,
65) (2R,3R)-3-(4-((5-chloropyrimidin-2-yl)amino)piperidin-1-yl)-2-(2,4-difluorophenyl)-1-(1H-1,2,4-triazol-1-yl)butan-2-ol,
66) (2R,3R)-2-(2,4-difluorophenyl)-3-(4-((5-methylpyrimidin-2-yl)amino)piperidin-1-yl)-1-(1H-1,2,4-triazol-1-yl)butan-2-ol,
67) (2R,3R)-2-(2,4-difluorophenyl)-3-(4-(methyl(phenyl)amino)piperidin-1-yl)-1-(1H-1,2,4-triazol-1-yl)butan-2-ol,
68) (2R,3R)-2-(2,4-difluorophenyl)-3-(4-((2-fluorophenyl)(methyl)amino)piperidin-1-yl)-1-(1H-1,2,4-triazol-1-yl)butan-2-ol,
69) (2R,3R)-2-(2,4-difluorophenyl)-3-(4-((3-fluorophenyl)(methyl)amino)piperidin-1-yl)-1-(1H-1,2,4-triazol-1-yl)butan-2-ol,
70) (2R,3R)-2-(2,4-difluorophenyl)-3-(4-((4-fluorophenyl)(methyl)amino)piperidin-1-yl)-1-(1H-1,2,4-triazol-1-yl)butan-2-ol,
71) (2R,3R)-3-(4-((2-chlorophenyl)(methyl)amino)piperidin-1-yl)-2-(2,4-difluorophenyl)-1-(1H-1,2,4-triazol-1-yl)butan-2-ol,
72) (2R,3R)-3-(4-((3-chlorophenyl)(methyl)amino)piperidin-1-yl)-2-(2,4-difluorophenyl)-1-(1H-1,2,4-triazol-1-yl)butan-2-ol,
73) (2R,3R)-3-(4-((4-chlorophenyl)(methyl)amino)piperidin-1-yl)-2-(2,4-difluorophenyl)-1-(1H-1,2,4-triazol-1-yl)butan-2-ol,
74) (2R,3R)-3-(4-((2-bromophenyl)(methyl)amino)piperidin-1-yl)-2-(2,4-difluorophenyl)-1-(1H-1,2,4-triazol-1-yl)butan-2-ol,
75) (2R,3R)-3-(4-((3-bromophenyl)(methyl)amino)piperidin-1-yl)-2-(2,4-difluorophenyl)-1-(1H-1,2,4-triazol-1-yl)butan-2-ol,
76) (2R,3R)-3-(4-((4-bromophenyl)(methyl)amino)piperidin-1-yl)-2-(2,4-difluorophenyl)-1-(1H-1,2,4-triazol-1-yl)butan-2-ol,
77) (2R,3R)-2-(2,4-difluorophenyl)-3-(4-(methyl(2-(trifluoromethyl)phenyl)amino)piperidin-1-yl)-1-(1H-1,2,4-triazol-1-yl)butan-2-ol,
78) (2R,3R)-2-(2,4-difluorophenyl)-3-(4-(methyl(3-(trifluoromethyl)phenyl)amino)piperidin-1-yl)-1-(1H-1,2,4-triazol-1-yl)butan-2-ol,
79) (2R,3R)-2-(2,4-difluorophenyl)-3-(4-(methyl(4-(trifluoromethyl)phenyl)amino)piperidin-1-yl)-1-(1H-1,2,4-triazol-1-yl)butan-2-ol,
80) 2-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
81) 3-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
82) 4-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
83) (2R,3R)-3-(4-((2,4-dichlorophenyl)(methyl)amino)piperidin-1-yl)-2-(2,4-difluorophenyl)-1-(1H-1,2,4-triazol-1-yl)butan-2-ol,
84) (2R,3R)-3-(4-((3,4-dichlorophenyl)(methyl)amino)piperidin-1-yl)-2-(2,4-difluorophenyl)-1-(1H-1,2,4-triazol-1-yl)butan-2-ol,
85) (2R,3R)-3-(4-((4-chloro-2-fluorophenyl)(methyl)amino)piperidin-1-yl)-2-(2,4-difluorophenyl)-1-(1H-1,2,4-triazol-1-yl)butan-2-ol,
86) (2R,3R)-2-(2,4-difluorophenyl)-3-(4-((2,4-difluorophenyl)(methyl)amino)piperidin-1-yl)-1-(1H-1,2,4-triazol-1-yl)butan-2-ol,
87) (2R,3R)-3-(4-((4-chloro-3-fluorophenyl)(methyl)amino)piperidin-1-yl)-2-(2,4-difluorophenyl)-1-(1H-1,2,4-triazol-1-yl)butan-2-ol,
88) (2R,3R)-3-(4-((4-chloro-2-methylphenyl)(methyl)amino)piperidin-1-yl)-2-(2,4-difluorophenyl)-1-(1H-1,2,4-triazol-1-yl)butan-2-ol,
89) (2R,3R)-2-(2,4-difluorophenyl)-3-((1-(pyrimidin-2-yl)piperidin-4-yl)oxy)-1-(1H-1,2,4-triazol-1-yl)butan-2-ol,
90) (2R,3R)-2-(2,4-difluorophenyl)-3-((1-phenylpiperidin-4-yl)oxy)-1-(1H-1,2,4-triazol-1-yl)butan-2-ol, 91) (2R,3R)-2-(2,4-difluorophenyl)-3-((1-(2-fluorophenyl)piperidin-4-yl)oxy)-1-(1H-1,2,4-triazol-1-yl)butan-2-ol,
92) (2R,3R)-2-(2,4-difluorophenyl)-3-((1-(3-fluorophenyl)piperidin-4-yl)oxy)-1-(1H-1,2,4-triazol-1-yl)butan-2-ol,
93) (2R,3R)-2-(2,4-difluorophenyl)-3-((1-(4-fluorophenyl)piperidin-4-yl)oxy)-1-(1H-1,2,4-triazol-1-yl)butan-2-ol,
94) (2R,3R)-3-((1-(2-bromophenyl)piperidin-4-yl)oxy)-2-(2,4-difluorophenyl)-1-(1H-1,2,4-triazol-1-yl)butan-2-ol,
95) (2R,3R)-3-((1-(3-chlorophenyl)piperidin-4-yl)oxy)-2-(2,4-difluorophenyl)-1-(1H-1,2,4-triazol-1-yl)butan-2-ol,
96) (2R,3R)-3-((1-(4-chlorophenyl)piperidin-4-yl)oxy)-2-(2,4-difluorophenyl)-1-(1H-1,2,4-triazol-1-yl)butan-2-ol,
97) (2R,3R)-3-((1-(2-bromophenyl)piperidin-4-yl)amino)-2-(2,4-difluorophenyl)-1-(1H-1,2,4-triazol-1-yl)butan-2-ol,
98) (2R,3R)-3-((1-(3-bromophenyl)piperidin-4-yl)oxy)-2-(2,4-difluorophenyl)-1-(1H-1,2,4-triazol-1-yl)butan-2-ol,
99) (2R,3R)-3-((1-(4-bromophenyl)piperidin-4-yl)oxy)-2-(2,4-difluorophenyl)-1-(1H-1,2,4-triazol-1-yl)butan-2-ol,
100) (2R,3R)-2-(2,4-difluorophenyl)-1-(1H-1,2,4-triazol-1-yl)-3-(1-(2-(trifluoromethyl)phenyl)piperidin-4-yl)oxy)butan-2-ol,
101) (2R,3R)-2-(2,4-difluorophenyl)-1-(1H-1,2,4-triazol-1-yl)-3-(1-(3-(trifluoromethyl)phenyl)piperidin-4-yl)oxy)butan-2-ol,
102) (2R,3R)-2-(2,4-difluorophenyl)-1-(1H-1,2,4-triazol-1-yl)-3-(1-(4-(trifluoromethyl)phenyl)piperidin-4-yl)oxy)butan-2-ol,
103) 2-(4-((2R,3R)-3-(2,4-difluorophenyl)-3-hydroxy-4-(1H-1,2,4-triazol-1-yl)butan-2-yl)oxy)piperidin-1-yl)benzonitrile,
104) 3-(4-((2R,3R)-3-(2,4-difluorophenyl)-3-hydroxy-4-(1H-1,2,4-triazol-1-yl)butan-2-yl)oxy)piperidin-1-yl)benzonitrile,
105) 4-(4-((2R,3R)-3-(2,4-difluorophenyl)-3-hydroxy-4-(1H-1,2,4-triazol-1-yl)butan-2-yl)oxy)piperidin-1-yl)benzonitrile,
106) (2R,3R)-3-((1-(2,4-dichlorophenyl)piperidin-4-yl)oxy)-2-(2,4-difluorophenyl)-1-(1H-1,2,4-triazol-1-yl)butan-2-ol,
107) (2R,3R)-3-((1-(3,4-dichlorophenyl)piperidin-4-yl)oxy)-2-(2,4-difluorophenyl)-1-(1H-1,2,4-triazol-1-yl)butan-2-ol,
108) (2R,3R)-3-((1-(4-chloro-2-fluorophenyl)piperidin-4-yl)oxy)-2-(2,4-difluorophenyl)-1-(1H-1,2,4-triazol-1-yl)butan-2-ol,
109) (2R,3R)-2-(2,4-difluorophenyl)-3-((1-(2,4-difluorophenyl)piperidin-4-yl)oxy)-1-(1H-1,2,4-triazol-1-yl)butan-2-ol,
110) (2R,3R)-3-((1-(4-chloro-3-fluorophenyl)piperidin-4-yl)oxy)-2-(2,4-difluorophenyl)-1-(1H-1,2,4-triazol-1-yl)butan-2-ol,
111) (2R,3R)-3-((1-(4-chloro-2-methylphenyl)piperidin-4-yl)oxy)-2-(2,4-difluorophenyl)-1-(1H-1,2,4-triazol-1-yl)butan-2-ol,
112) (2R,3R)-2-(2,4-difluorophenyl)-3-(1-(pyridin-2-yl)piperidin-4-yl)oxy)-1-(1H-1,2,4-triazol-1-yl)butan-2-ol,
113) (2R,3R)-2-(2,4-difluorophenyl)-3-((1-(5-methylpyridin-2-yl)piperidin-4-yl)oxy)-1-(1H-1,2,4-triazol-1-yl)butan-2-ol,
114) (2R,3R)-2-(2,4-difluorophenyl)-3-((1-(5-fluoropyridin-2-yl)piperidin-4-yl)oxy)-1-(1H-1,2,4-triazol-1-yl)butan-2-ol,
115) (2R,3R)-3-((1-(5-chloropyridin-2-yl)piperidin-4-yl)oxy)-2-(2,4-difluorophenyl)-1-(1H-1,2,4-triazol-1-yl)butan-2-ol,
116) (2R,3R)-2-(2,4-difluorophenyl)-3-((1-(3-methyl-5-(trifluoromethyl)pyridin-2-yl)piperidin-4-yl)oxy)-1-(1H-1,2,4-triazol-1-yl)butan-2-ol,
117) (2R,3R)-2-(2,4-difluorophenyl)-3-((1-(5-methylpyrimidin-2-yl)piperidin-4-yl)oxy)-1-(1H-1,2,4-triazol-1-yl)butan-2-ol,
118) (2R,3R)-2-(2,4-difluorophenyl)-3-((1-(5-fluoropyrimidin-2-yl)piperidin-4-yl)oxy)-1-(1H-1,2,4-triazol-1-yl)butan-2-ol,
119) (2R,3R)-3-((1-(5-chloropyrimidin-2-yl)piperidin-4-yl)oxy)-2-(2,4-difluorophenyl)-1-(1H-1,2,4-triazol-1-yl)butan-2-ol,
120) (2R,3R)-3-((1-(5-bromopyrimidin-2-yl)piperidin-4-yl)oxy)-2-(2,4-difluorophenyl)-1-(1H-1,2,4-triazol-1-yl)butan-2-ol,
121) (2R,3R)-2-(2,4-difluorophenyl)-1-(1H-1,2,4-triazol-1-yl)-3-((1-(4-(trifluoromethyl)pyrimidin-2-yl)piperidin-4-yl)oxy)butan-2-ol,
122) (2R,3R)-2-(2,4-difluorophenyl)-3-((1-(2-fluorophenyl)piperidin-4-yl)amino)-1-(1H-1,2,4-triazol-1-yl)butan-2-ol,
123) (2R,3R)-2-(2,4-difluorophenyl)-3-((1-phenylpiperidin-4-yl)amino)-1-(1H-1,2,4-triazol-1-yl)butan-2-ol,
124) (2R,3R)-2-(2,4-difluorophenyl)-3-((1-(3-fluorophenyl)piperidin-4-yl)amino)-1-(1H-1,2,4-triazol-1-yl)butan-2-ol,
125) (2R,3R)-2-(2,4-difluorophenyl)-3-((1-(4-fluorophenyl)piperidin-4-yl)amino)-1-(1H-1,2,4-triazol-1-yl)butan-2-ol,
126) (2R,3R)-3-((1-(2-chlorophenyl)piperidin-4-yl)amino)-2-(2,4-difluorophenyl)-1-(1H-1,2,4-triazol-1-yl)butan-2-ol,
127) (2R,3R)-3-((1-(3-chlorophenyl)piperidin-4-yl)amino)-2-(2,4-difluorophenyl)-1-(1H-1,2,4-triazol-1-yl)butan-2-ol,
128) (2R,3R)-3-((1-(4-chlorophenyl)piperidin-4-yl)amino)-2-(2,4-difluorophenyl)-1-(1H-1,2,4-triazol-1-yl)butan-2-ol,
129) (2R,3R)-3-((1-(2-bromophenyl)piperidin-4-yl)amino)-2-(2,4-difluorophenyl)-1-(1H-1,2,4-triazol-1-yl)butan-2-ol,
130) (2R,3R)-3-((1-(3-bromophenyl)piperidin-4-yl)amino)-2-(2,4-difluorophenyl)-1-(1H-1,2,4-triazol-1-yl)butan-2-ol,
131) (2R,3R)-3-((1-(4-bromophenyl)piperidin-4-yl)amino)-2-(2,4-difluorophenyl)-1-(1H-1,2,4-triazol-1-yl)butan-2-ol,
132) (2R,3R)-2-(2,4-difluorophenyl)-1-(1H-1,2,4-triazol-1-yl)-3-((1-(2-(trifluoromethyl)phenyl)piperidin-4-yl)amino)butan-2-ol,
133) (2R,3R)-2-(2,4-difluorophenyl)-1-(1H-1,2,4-triazol-1-yl)-3-((1-(3-(trifluoromethyl)phenyl)piperidin-4-yl)amino)butan-2-ol,
134) (2R,3R)-2-(2,4-difluorophenyl)-1-(1H-1,2,4-triazol-1-yl)-3-((1-(4-(trifluoromethyl)phenyl)piperidin-4-yl)amino)butan-2-ol,
135) 2-(4-(((2R,3R)-3-(2,4-difluorophenyl)-3-hydroxy-4-(1H-1,2,4-triazol-1-yl)butan-2-yl)amino)piperidin-1-yl)benzonitrile,
136) 3-(4-(((2R,3R)-3-(2,4-difluorophenyl)-3-hydroxy-4-(1H-1,2,4-triazol-1-yl)butan-2-yl)amino)piperidin-1-yl)benzonitrile,
137) 4-(4-(((2R,3R)-3-(2,4-difluorophenyl)-3-hydroxy-4-(1H-1,2,4-triazol-1-yl)butan-2-yl)amino)piperidin-1-yl)benzonitrile, 138) (2R,3R)-3-((1-(2,4-dichlorophenyl)piperidin-4-yl)amino)-2-(2,4-difluorophenyl)-1-(1H-1,2,4-triazol-1-yl)butan-2-ol,
139) (2R,3R)-3-((1-(3,4-dichlorophenyl)piperidin-4-yl)amino)-2-(2,4-difluorophenyl)-1-(1H-1,2,4-triazol-1-yl)butan-2-ol,
140) (2R,3R)-3-((1-(4-chloro-2-fluorophenyl)piperidin-4-yl)amino)-2-(2,4-difluorophenyl)-1-(1H-1,2,4-triazol-1-yl)butan-2-ol,
141) (2R,3R)-2-(2,4-difluorophenyl)-3-((1-(2,4-difluorophenyl)piperidin-4-yl)amino)-1-(1H-1,2,4-triazol-1-yl)butan-2-ol,
142) (2R,3R)-3-((1-(4-chloro-3-fluorophenyl)piperidin-4-yl)amino)-2-(2,4-difluorophenyl)-1-(1H-1,2,4-triazol-1-yl)butan-2-ol,
143) (2R,3R)-3-((1-(4-chloro-2-methylphenyl)piperidin-4-yl)amino)-2-(2,4-difluorophenyl)-1-(1H-1,2,4-triazol-1-yl)butan-2-ol,
144) (2R,3R)-2-(2,4-difluorophenyl)-3-((1-(pyridin-2-yl)piperidin-4-yl)amino)-1-(1H-1,2,4-triazol-1-yl)butan-2-ol,
145) (2R,3R)-2-(2,4-difluorophenyl)-3-((1-(5-methylpyridin-2-yl)piperidin-4-yl)amino)-1-(1H-1,2,4-triazol-1-yl)butan-2-ol,
146) (2R,3R)-2-(2,4-difluorophenyl)-3-((1-(5-fluoropyridin-2-yl)piperidin-4-yl)amino)-1-(1H-1,2,4-triazol-1-yl)butan-2-ol,
147) (2R,3R)-3-((1-(5-chloropyridin-2-yl)piperidin-4-yl)amino)-2-(2,4-difluorophenyl)-1-(1H-1,2,4-triazol-1-yl)butan-2-ol,
148) (2R,3R)-2-(2,4-difluorophenyl)-3-((1-(3-methyl-5-(trifluoromethyl)pyridin-2-yl)piperidin-4-yl)amino)-1-(1H-1,2,4-triazol-1-yl)butan-2-ol,
149) (2R,3R)-2-(2,4-difluorophenyl)-3-((1-(pyrimidin-2-yl)piperidin-4-yl)amino)-1-(1H-1,2,4-triazol-1-yl)butan-2-ol,
150) (2R,3R)-2-(2,4-difluorophenyl)-3-((1-(5-methylpyrimidin-2-yl)piperidin-4-yl)amino)-1-(1H-1,2,4-triazol-1-yl)butan-2-ol,
151) (2R,3R)-2-(2,4-difluorophenyl)-3-((1-(5-fluoropyrimidin-2-yl)piperidin-4-yl)amino)-1-(1H-1,2,4-triazol-1-yl)butan-2-ol,
152) (2R,3R)-3-((1-(5-chloropyrimidin-2-yl)piperidin-4-yl)amino)-2-(2,4-difluorophenyl)-1-(1H-1,2,4-triazol-1-yl)butan-2-ol,
153) (2R,3R)-3-((1-(5-bromopyrimidin-2-yl)piperidin-4-yl)amino)-2-(2,4-difluorophenyl)-1-(1H-1,2,4-triazol-1-yl)butan-2-ol,
154) (2R,3R)-2-(2,4-difluorophenyl)-1-(1H-1,2,4-triazol-1-yl)-3-((1-(4-(trifluoromethyl)pyrimidin-2-yl)piperidin-4-yl)amino)butan-2-ol,
155) (2R,3R)-2-(2,4-difluorophenyl)-3-(methyl(1-phenylpiperidin-4-yl)amino)-1-(1H-1,2,4-triazol-1-yl)butan-2-ol,
156) (2R,3R)-2-(2,4-difluorophenyl)-3-((1-(2-fluorophenyl)piperidin-4-yl)(methyl)amino)-1-(1H-1,2,4-triazol-1-yl)butan-2-ol,
157) (2R,3R)-2-(2,4-difluorophenyl)-3-((1-(3-fluorophenyl)piperidin-4-yl)(methyl)amino)-1-(1H-1,2,4-triazol-1-yl)butan-2-ol,
158) (2R,3R)-2-(2,4-difluorophenyl)-3-((1-(4-fluorophenyl)piperidin-4-yl)(methyl)amino)-1-(1H-1,2,4-triazol-1-yl)butan-2-ol,
159) (2R,3R)-3-((1-(2-chlorophenyl)piperidin-4-yl)(methyl)amino)-2-(2,4-difluorophenyl)-1-(1H-1,2,4-triazol-1-yl)butan-2-ol,
160) (2R,3R)-3-((1-(3-chlorophenyl)piperidin-4-yl)(methyl)amino)-2-(2,4-difluorophenyl)-1-(1H-1,2,4-triazol-1-yl)butan-2-ol,
161) (2R,3R)-3-((1-(4-chlorophenyl)piperidin-4-yl)(methyl)amino)-2-(2,4-difluorophenyl)-1-(1H-1,2,4-triazol-1-yl)butan-2-ol,
162) (2R,3R)-3-((1-(2-bromophenyl)piperidin-4-yl)(methyl)amino)-2-(2,4-difluorophenyl)-1-(1H-1,2,4-triazol-1-yl)butan-2-ol,
163) (2R,3R)-3-((1-(3-bromophenyl)piperidin-4-yl)(methyl)amino)-2-(2,4-difluorophenyl)-1-(1H-1,2,4-triazol-1-yl)butan-2-ol,
164) (2R,3R)-3-((1-(4-bromophenyl)piperidin-4-yl)(methyl)amino)-2-(2,4-difluorophenyl)-1-(1H-1,2,4-triazol-1-yl)butan-2-ol,
165) (2R,3R)-2-(2,4-difluorophenyl)-3-(methyl(1-(2-(trifluoromethyl)phenyl)piperidin-4-yl)amino)-1-(1H-1,2,4-triazol-1-yl)butan-2-ol,
166) (2R,3R)-2-(2,4-difluorophenyl)-3-(methyl(1-(3-(trifluoromethyl)phenyl)piperidin-4-yl)amino)-1-(1H-1,2,4-triazol-1-yl)butan-2-ol,
167) (2R,3R)-2-(2,4-difluorophenyl)-3-(methyl(1-(4-(trifluoromethyl)phenyl)piperidin-4-yl)amino)-1-(1H-1,2,4-triazol-1-yl)butan-2-ol,
168) 2-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
169) 3-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
170) 4-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
171) (2R,3R)-3-((1-(2,4-dichlorophenyl)piperidin-4-yl)(methyl)amino)-2-(2,4-difluorophenyl)-1-(1H-1,2,4-triazol-1-yl)butan-2-ol,
172) (2R,3R)-3-((1-(3,4-dichlorophenyl)piperidin-4-yl)(methyl)amino)-2-(2,4-difluorophenyl)-1-(1H-1,2,4-triazol-1-yl)butan-2-ol,
173) (2R,3R)-3-((1-(4-chloro-2-fluorophenyl)piperidin-4-yl)(methyl)amino)-2-(2,4-difluorophenyl)-1-(1H-1,2,4-triazol-1-yl)butan-2-ol,
174) (2R,3R)-2-(2,4-difluorophenyl)-3-((1-(2,4-difluorophenyl)piperidin-4-yl)(methyl)amino)-1-(1H-1,2,4-triazol-1-yl)butan-2-ol,
175) (2R,3R)-3-((1-(4-chloro-3-fluorophenyl)piperidin-4-yl)(methyl)amino)-2-(2,4-difluorophenyl)-1-(1H-1,2,4-triazol-1-yl)butan-2-ol,
176) (2R,3R)-3-((1-(4-chloro-2-methylphenyl)piperidin-4-yl)(methyl)amino)-2-(2,4-difluorophenyl)-1-(1H-1,2,4-triazol-1-yl)butan-2-ol,
177) (2R,3R)-2-(2,4-difluorophenyl)-3-((1-phenylpiperidin-3-yl)amino)-1-(1H-1,2,4-triazol-1-yl)butan-2-ol,
178) (2R,3R)-2-(2,4-difluorophenyl)-3-(3-(phenylamino)pyrrolidin-1-yl)-1-(1H-1,2,4-triazol-1-yl)butan-2-ol,
179) (2R,3R)-3-((R)-3-(4-chlorophenoxy)pyrrolidin-1-yl)-2-(2,4-difluorophenyl)-1-(1H-1,2,4-triazol-1-yl)butan-2-ol, and
180) (2R,3R)-3-((S)-3-(4-chlorophenoxy)pyrrolidin-1-yl)-2-(2,4-difluorophenyl)-1-(1H-1,2,4-triazol-1-yl)butan-2-ol.

Also, the present invention provides a pharmaceutically acceptable inorganic or organic salt of the compound represented by Chemical Formula 1. The pharmaceutically acceptable salt useful in the present invention may be an inorganic or organic acid salt that is known in the technical field to which antifungal agents belong. It can be prepared using a well-known method. Examples of the pharmaceutically acceptable salts include acid addition salts prepared from inorganic acids such as chloric acid, nitric acid, etc.; sulfonic acids such as methanesulfonic acid, etc. or organic carbonic acids such as oxalic acid, etc.

The compound represented by Chemical Formula 1 retains two asymmetric carbons. In Chemical Formula I, there are two chiral centers at positions C2 and C3. Of the optical isomers of Chemical Formula 1, optically active (2R,3R)-configuration compounds are preferred in accordance with the present invention. Unless stated specifically, therefore, the enantiomers of the compounds of Chemical Formula 1 fall within the scope of the present invention.

In addition, hydrates and solvates of the compounds of Chemical Formula 1 are within the scope of the present invention.

In accordance with another aspect thereof, the present invention provides an antifungal composition comprising a compound represented by Chemical Formula 1 or a pharmaceutically acceptable salt thereof as an active ingredient. Further, the present invention provides a pharmaceutical composition for use in the prevention or treatment of fungal infections, comprising a compound represented by Chemical Formula 1 or a pharmaceutically acceptable salt thereof as an active ingredient. Further, the present invention provides a method for prevention or treatment of fungal infections in a subject in need thereof, comprising administering to the subject a therapeutically effective amount of a compound represented by Chemical Formula 1 or a pharmaceutically acceptable salt thereof.

Exhibiting excellent antifungal activity and in vivo safety, the compounds of Chemical Formula 1, and their pharmaceutically acceptable salts, isomers, hydrates and solvates can be useful for treating or preventing various fungal infections caused by for example *Candida* spp., *Aspergillus* spp., *Cryptococcus neoformans*, *Trichophyton* spp., etc. Accordingly, the present invention provides a pharmaceutical composition for the treatment or prevention of fungal infections, comprising a compound selected from the group consisting of the compounds of Chemical Formula 1, and their pharmaceutically acceptable salts, isomers, hydrates and solvates as an active ingredient. In this context, the pharmaceutical composition for the treatment or-prevention of fungal infections in accordance with the present invention may comprise a pharmaceutically acceptable carrier or vehicle.

The pharmaceutical composition in which the compound of the present invention may be in a mixture with a pharmaceutically acceptable, inactive carrier or vehicle may be formulated into various dosage forms using typical techniques.

For example, the compound according to the present invention may be formulated, in combination with a carrier or vehicle, into an injection, a representative parenteral dosage form. Preferable is an isotonic aqueous solution or suspension. Another dosage form into which the composition according to the present invention may be formulated may be in an oral form, such as a tablet or a capsule. These formulations may comprise diluents (for example, lactose, dextrose, sucrose, mannitol, cellulose or glycin), lubricants (for example, silica, talc, stearic acid and its magnesium or calcium salt, or polyethylene glycol) and/or binders (for example, magnesium silicate, starch paste, gelatin, tragacanth, methyl cellulose, sodium carboxymethylcellulose or polyvinyl pyrrolidone) in addition to the active ingredient. Optionally, they may further comprise disintegrants such as starch, agar, alginate or sodium salts thereof, azeotropic mixtures, absorbants, colorants, flavorants and/or sweeteners.

The dose of the active ingredient, that is, the compound of the present invention may vary depending on various factors including a patient's condition and sex, the severity of the disease, administration routes, physician's prescription, etc. and may be readily determined by those skilled in the art. Preferably, the compound of the present invention may be administered orally or by injection at a dose of from 0.05 mg/kg/day to 200 mg/kg/day, and more preferably at a dose of from 0.05 mg/kg/day to 100 mg/kg/day.

In accordance with a further aspect thereof, the present invention provides a method for the preparation of a compound represented by Chemical Formula 1 (wherein A is

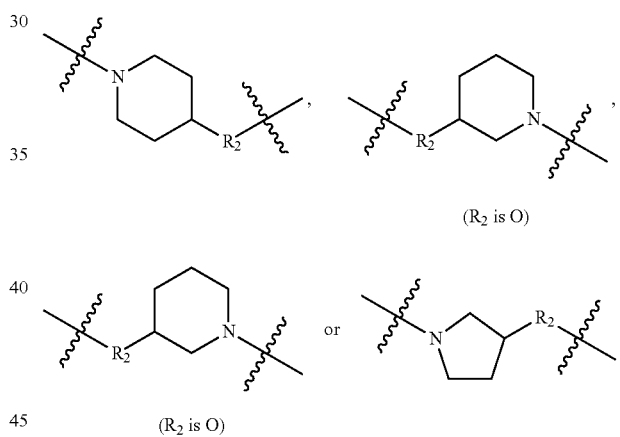

($R_2$ is O)

($R_2$ is O)

), as illustrated in the following Reaction Scheme 1:

[Reaction Scheme 1]

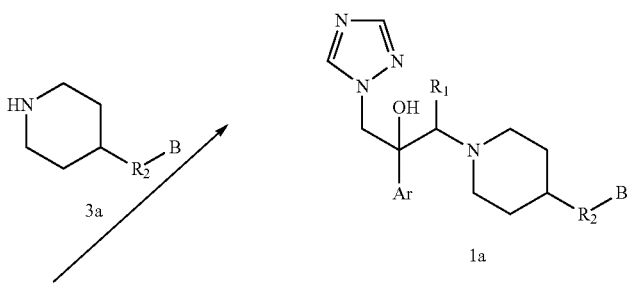

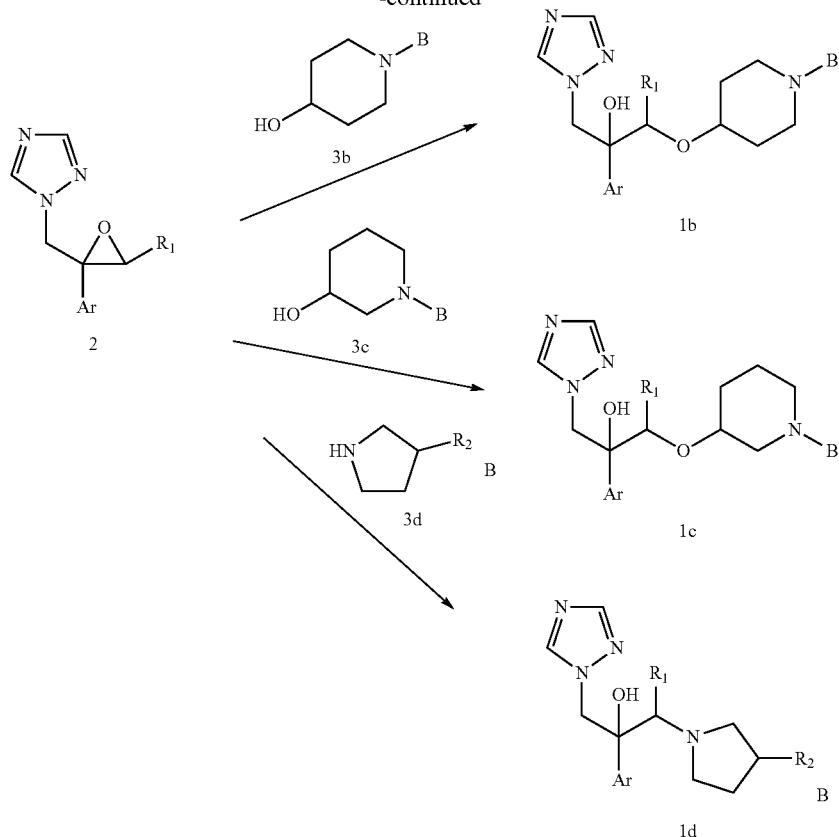

wherein $R_1$, $R_2$ and B are respectively as defined above. The reaction is conducted in the presence of an acid catalyst or a base.

The epoxide of Chemical Formula 2 is a well known compound and may be synthesized using the method disclosed in for example [*Chem. Pharm. Bull.*, Tasaka et al., 1993, 41(6), 1035-1042].

Also, the compounds of Chemical Formula 3a, 3b, 3c or 3d is a well known compound which is may be synthesized using a typical method or may be commercially available.

Preferably, the compound of Chemical Formula 3a, 3b, 3c or 3d may be used in an amount of 1 to 3 moles per mole of the compound of Chemical Formula 2.

A typical inorganic or organic base may be used for the reaction of Reaction Scheme 1. Sodium hydride (NaH), potassium carbonate ($K_2CO_3$) or sodium methoxide (MeONa) is suitable for use as an inorganic base. Among the organic bases useful in the present invention are triethylamine and 1,8-diazabicyclo[5,4,0]undec-7-ene (DBU).

An acid catalyst for use in the reaction of Reaction Scheme 1 may include lithium perchlorate ($LiClO_4$), sodium perchlorate ($NaClO_4$), potassium perchlorate ($KClO_4$), and cesium perchlorate ($CsClO_4$).

For the preparation of the compound of Chemical Formula 1, the reactions of Reaction Scheme 1 may be preferably conducted in a solvent. Suitable is a polar organic solvent such as methanol, ethanol, acetonitrile, dimethoxyethane, dimethyl formamide, dimethyl sulfoxide and tetrahydrofuran.

The reactions may be conducted at 0 to 200° C. and more preferably at 30 to 200° C. for 2 min to 24 hrs using typical organic synthesis methods or a microwave-based system to afford the compound of Chemical Formula 1.

In accordance with a further aspect thereof, the present invention provides a method for the preparation of the compound represented by Chemical Formula 1

(wherein A is

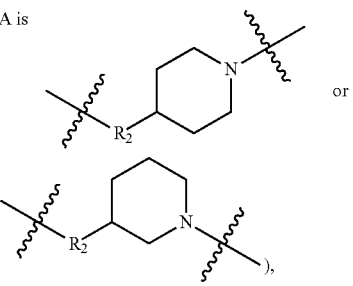

or

), as illustrated in the following Reaction Scheme 2:

[Reaction Scheme 2]

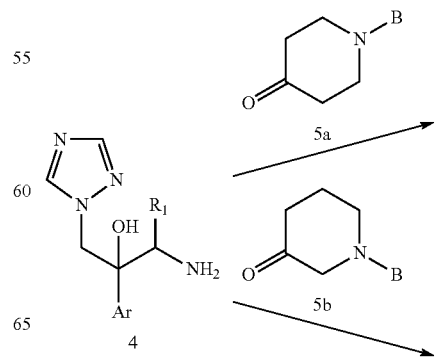

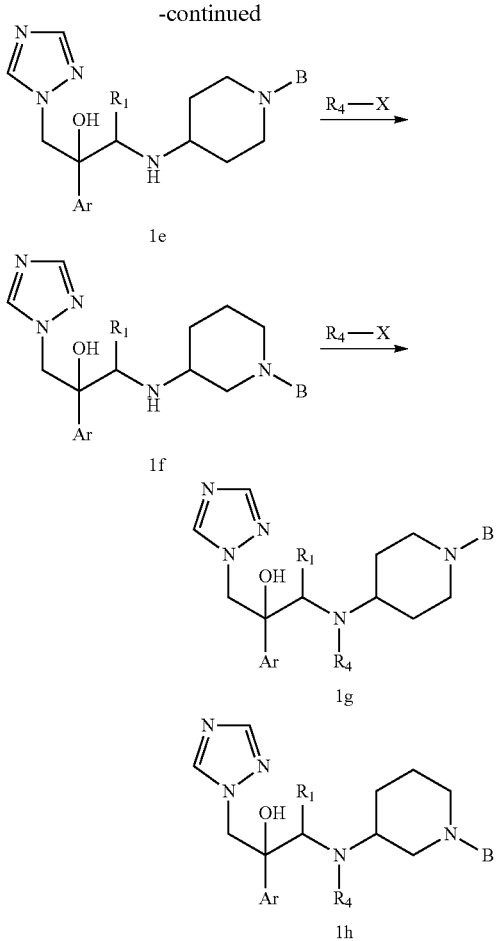

wherein Ar, R$_1$ and B are as defined above, R$_4$ is methyl, and X is halogen, preferably Br or I. The reactions of Reaction Scheme 2 may be performed in a weakly acidic condition and in the presence of a base.

The compound of Chemical Formula 4 may be prepared from the compound of Chemical Formula 2 using a typical method.

The compound of Chemical Formula 5a or 5b is also well known in the art and may be prepared using a typical method or may be commercially available.

Preferably, the compound of Chemical Formula 5a or 5b may be used in an amount of from 0.5 to 2 moles per mole of the compound of Chemical Formula 4.

As for the weakly acidic condition for preparing the compound of Chemical Formula 1e or 1f, it may be performed by using metal alkoxide such as titanium (IV) isopropoxide (Ti (i-PrO)$_4$) in the presence of a reducing agent such as sodium cyanoborohydride (NaCNBH$_4$), sodium triacetoxyborohydride (Na(OAc)$_3$BH), or borane-pyridine (BH$_3$-Pyridine).

As for the weakly acidic condition for preparing the compound of Chemical Formula 1g or 1h, it may be performed by reacting with iodomethane or bromomethane in the presence of an inorganic base such as potassium carbonate (K$_2$CO$_3$), sodium carbonate (Na$_2$CO$_3$) or sodium hydride (NaH), or by reacting with formaldehyde in the presence of sodium cyanoborohydride (NaCNBH$_4$) or sodium triacetoxyborohydride (Na(OAc)$_3$BH) and in a weakly acid condition such as acetic acid, hydrochloride or formic acid.

For the preparation of the compound of Chemical Formula 1, the reactions of Reaction Scheme 2 may be preferably conducted in a solvent. Suitable is a polar organic solvent such as methanol, ethanol, acetonitrile, dimethoxyethane, dimethyl formamide, dimethyl sulfoxide and tetrahydrofuran.

The reactions may be conducted at 0 to 200° C. and more preferably at 30 to 200° C. for 2 min to 24 hrs using typical organic synthesis methods or a microwave-based system to afford the compound of Chemical Formula 1.

Advantageous Effects of Invention

Having excellent antifungal activity and in vivo safety, the triazole derivatives according to the present invention are useful for the treatment or prevention of fungal infections caused by a wide spectrum of fungi.

MODE FOR THE INVENTION

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE 1

Preparation of (2R,3R)-2-(2,4-difluorophenyl)-3-(4-(4-fluorophenoxy)piperidin-1-yl)-1-(1H-1,2,4-triazol-1-yl)butan-2-ol To a suspension of acetonitrile (4 mL) in 4-(4-fluorophenoxy)piperidine (180.5 mg, 0.92 mmol) in a microwave reaction vessel were added lithium perchlorate (133.4 mg, 1.25 mmol) and 1-(((2R,3R)-2-(2,4-difluorophenyl)-3-methyloxyran-2-yl)methyl)-1H-1,2,4-triazole (126.0 mg, 0.48 mmol), followed by exposure to microwaves at 160° C. for 30 min. After the termination of the reaction, the reaction mixture was concentrated in a vacuum, diluted in ethyl acetate and washed with distilled water and saline to separate an organic solvent layer. The organic solvent layer was dried over anhydrous magnesium sulfate and evaporated at reduced pressure. Isolation and purification of the residue through silica gel chromatography afforded the title compound as a white solid (yield 42%).

$^1$H-NMR (CDCl$_3$, 300 MHz) δ 8.00 (s, 1H), 7.78 (s, 1H), 7.53-7.44 (m, 1H), 6.98-6.91 (m, 2H), 6.86-6.69 (m, 4H), 5.34 (bs, 1H), 4.87 (d, 1H, J=14.4 Hz), 4.80 (d, 1H, J=15.2 Hz), 4.25-4.11 (m, 1H), 3.02-2.89 (m, 2H), 2.62-2.59 (m, 2H), 2.28-2.20 (m, 1H), 1.98-1.93 (m, 2H), 1.85-1.72 (m, 2H), 1.00-0.96 (d, 3H).

Compounds of Examples 2 to 33 were synthesized in similar manners to the method of Example 1.

EXAMPLE 2

Preparation of (2R,3R)-2-(2,4-difluorophenyl)-3-(4-phenoxypiperidin-1-yl)-1-(1H-1,2,4-triazol-1-yl)butan-2-ol $^1$H-NMR (CDCl$_3$, 300 MHz) δ 8.00 (s, 1H), 7.78 (s, 1H), 7.35 (m, 2H), 7.01 (m, 2H), 6.78 (m, 4H), 5.34 (bs, 1H), 4.87 (d, 1H, J=14.4 Hz), 4.80 (d, 1H, J=15.2 Hz), 4.18 (m, 1H), 2.92 (m, 2H), 2.60 (m, 2H), 2.24 (m, 1H), 1.95 (m, 2H), 1.79 (m, 2H), 0.99 (d, 3H)

EXAMPLE 3

Preparation of (2R,3R)-2-(2,4-difluorophenyl)-3-(4-(2-fluorophenoxy)piperidin-1-yl)-1-(1H-1,2,4-triazol-1-yl)butan-2-ol $^1$H-NMR (CDCl$_3$, 300 MHz) δ 8.02 (s, 1H), 7.78 (s, 1H), 7.48 (m, 1H), 7.01 (m, 2H), 6.78 (m, 4H), 5.34 (bs, 1H), 4.87 (d, 1H, J=14.4 Hz), 4.80 (d, 1H, J=15.2 Hz), 4.18 (m, 1H), 2.91 (m, 2H), 2.60 (m, 2H), 2.24 (m, 1H), 1.95 (m, 2H), 1.79 (m, 2H), 0.99 (d, 3H)

EXAMPLE 4

Preparation of (2R,3R)-2-(2,4-difluorophenyl)-3-(4-(3-fluorophenoxy)piperidin-1-yl)-1-(1H-1,2,4-triazol-1-yl)butan-2-ol $^1$H-NMR (CDCl$_3$, 300 MHz) δ 8.00 (s, 1H), 7.75 (s, 1H), 7.48 (m, 1H), 7.02 (m, 2H), 6.78 (m, 4H), 5.34 (bs, 1H), 4.87 (d, 1H, J=14.4 Hz), 4.80 (d, 1H, J=15.2 Hz), 4.18 (m, 1H), 2.91 (m, 2H), 2.53 (m, 2H), 2.24 (m, 1H), 1.95 (m, 2H), 1.79 (m, 2H), 0.99 (d, 3H)

EXAMPLE 5

Preparation of (2R,3R)-3-(4-(2-chlorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.02 (s, 1H), 7.88 (s, 1H), 7.48 (m, 1H), 7.01 (m, 2H), 6.78 (m, 4H), 5.50 (bs, 1H), 4.87 (d, 1H, J=14.4 Hz), 4.80 (d, 1H, J=15.2 Hz), 4.18 (m, 1H), 2.91 (m, 2H), 2.60 (m, 2H), 2.24 (m, 1H), 1.95 (m, 2H), 1.79 (m, 2H), 0.99 (d, 3H)

EXAMPLE 6

Preparation of (2R,3R)-3-(4-(3-chlorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.00 (s, 1H), 7.82 (s, 1H), 7.48 (m, 1H), 7.02 (m, 2H), 6.78 (m, 4H), 5.50 (bs, 1H), 4.87 (d, 1H, J=14.4 Hz), 4.80 (d, 1H, J=15.2 Hz), 4.18 (m, 1H), 2.91 (m, 2H), 2.53 (m, 2H), 2.24 (m, 1H), 1.95 (m, 2H), 1.79 (m, 2H), 0.99 (d, 3H)

EXAMPLE 7

Preparation of (2R,3R)-3-(4-(4-chlorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 7.99 (s, 1H), 7.78 (s, 1H), 7.49-7.44 (m, 1H), 7.22-7.19 (m, 2H), 6.82-6.70 (m, 4H), 4.85-4.82 (m, 2H), 4.82 (s, 1H), 2.96-2.92 (m, 2H), 2.63-2.60 (m, 2H), 2.26-2.24 (m, 1H), 1.98-1.93 (m, 2H), 1.80-1.74 (m, 2H), 0.98 (d, 3H)

EXAMPLE 8

Preparation of (2R,3R)-3-(4-(2-bromophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.10 (s, 1H), 7.91 (s, 1H), 7.48 (m, 1H), 7.05 (m, 2H), 6.87 (m, 4H), 4.90 (d, 1H, J=14.4 Hz), 4.80 (d, 1H, J=15.2 Hz), 4.18 (m, 1H), 2.95 (m, 2H), 2.60 (m, 2H), 2.24 (m, 1H), 2.01 (m, 2H), 1.81 (m, 2H), 1.10 (d, 3H)

EXAMPLE 9

Preparation of (2R,3R)-3-(4-(3-bromophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.00 (s, 1H), 7.82 (s, 1H), 7.48 (m, 1H), 7.02 (m, 2H), 6.78 (m, 4H), 5.50 (bs, 1H), 4.87 (d, 1H, J=14.4 Hz), 4.80 (d, 1H, J=15.2 Hz), 4.18 (m, 1H), 2.91 (m, 2H), 2.53 (m, 2H), 2.24 (m, 1H), 1.98 (m, 2H), 1.79 (m, 2H), 1.09 (d, 3H)

EXAMPLE 10

Preparation of (2R,3R)-3-(4-(4-bromophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.00 (s, 1H), 7.81 (s, 1H), 7.48 (m, 1H), 7.02 (m, 2H), 6.78 (m, 4H), 5.48 (bs, 1H), 4.87 (d, 1H, J=14.4 Hz), 4.80 (d, 1H, J=15.2 Hz), 4.18 (m, 1H), 2.91 (m, 2H), 2.41 (m, 2H), 2.24 (m, 1H), 1.98 (m, 2H), 1.79 (m, 2H), 1.0 (d, 3H)

EXAMPLE 11

Preparation of (2R,3R)-2-(2,4-difluorophenyl)-1-(1H-1,2,4-triazol-1-yl)-3-(4-(2-(trifluoromethyl)$_p$henoxy)piperidin-1-yl)butan-2-ol $^1$H-NMR (CDCl$_3$, 300 MHz) δ 7.89 (s, 1H), 7.73 (s, 1H), 7.48 (m, 3H), 6.87 (m, 4H), 5.52 (bs, 1H), 4.90 (d, 1H, J=14.4 Hz), 4.80 (d, 1H, J=15.2 Hz), 4.18 (m, 1H), 2.95 (m, 2H), 2.60 (m, 2H), 2.24 (m, 1H), 2.01 (m, 2H), 1.81 (m, 2H), 0.97 (d, 3H)

EXAMPLE 12

Preparation of (2R,3R)-2-(2,4-difluorophenyl)-1-(1H-1,2,4-triazol-1-yl)-3-(4-(3-(trifluoromethyl)$_p$henoxy)piperidin-1-yl)butan-2-ol $^1$H-NMR (CDCl$_3$, 300 MHz) δ 7.92 (s, 1H), 7.73 (s, 1H), 7.51 (m, 3H), 6.78 (m, 4H), 5.50 (bs, 1H), 4.87 (d, 1H, J=14.4 Hz), 4.80 (d, 1H, J=15.2 Hz), 4.18 (m, 1H), 2.91 (m, 2H), 2.53 (m, 2H), 2.24 (m, 1H), 1.98 (m, 2H), 1.79 (m, 2H), 0.98 (d, 3H)

EXAMPLE 13

Preparation of (2R,3R)-2-(2,4-difluorophenyl)-1-(1H-1,2,4-triazol-1-yl)-3-(4-(4-(trifluoromethyl)phenoxy)piperidin-1-yl)butan-2-ol $^1$H-NMR (CDCl$_3$, 300 MHz) δ 7.98 (s, 1H), 7.78 (s, 1H), 7.52-7.45 (m, 3H), 6.94-6.91 (d, 2H), 6.79-6.69 (m, 2H), 4.85-4.83 (q, 2H), 4.33 (s, 1H), 3.03-2.93 (m, 2H), 2.66-2.63 (m, 2H), 2.29-2.27 (m, 1H), 1.98-1.97 (m, 1H), 1.86-1.77 (m, 3H), 0.97 (d, 3H)

EXAMPLE 14

Preparation of 2-((1-(((2R,3R)-3-(2,4-difluorophenyl)-3-hydroxy-4-(1H-1,2,4-triazol-1-yl)butan-2-yl)piperidin-4-yl)oxy)benzonitrile $^1$H-NMR (CDCl$_3$, 300 MHz) δ 8.10 (s, 1H), 7.91 (s, 1H), 7.63 (m, 3H), 6.96 (m, 4H), 5.68 (bs, 1H), 4.87 (d, 1H, J=14.4 Hz), 4.80 (d, 1H, J=15.2 Hz), 4.18 (m, 1H), 2.94 (m, 2H), 2.58 (m, 2H), 2.24 (m, 1H), 1.98 (m, 2H), 1.79 (m, 2H), 1.09 (d, 3H)

EXAMPLE 15

Preparation of 3-((1-(((2R,3R)-3-(2,4-difluorophenyl)-3-hydroxy-4-(1H-1,2,4-triazol-1-yl)butan-2-yl)piperidin-4-yl)oxy)benzonitrile $^1$H-NMR (CDCl$_3$, 300 MHz) δ 8.10 (s, 1H), 7.90 (s, 1H), 7.68 (m, 3H), 6.96 (m, 4H), 5.70 (bs, 1H), 4.87 (d, 1H, J=14.4 Hz), 4.80 (d, 1H, J=15.2 Hz), 4.18 (m, 1H), 2.95 (m, 2H), 2.62 (m, 2H), 2.24 (m, 1H), 1.98 (m, 2H), 1.79 (m, 2H), 1.09 (d, 3H)

EXAMPLE 16

Preparation of 4-((1-(((2R,3R)-3-(2,4-difluorophenyl)-3-hydroxy-4-(1H-1,2,4-triazol-1-yl)butan-2-yl)piperidin-4-yl)oxy)benzonitrile $^1$H-NMR (CDCl$_3$, 300 MHz) δ 8.11 (s, 1H), 7.92 (s, 1H), 7.71 (m, 3H), 6.96 (m, 4H), 5.70 (bs, 1H), 4.87 (d, 1H, J=14.4 Hz), 4.80 (d, 1H, J=15.2 Hz), 4.18 (m, 1H), 2.95 (m, 2H), 2.62 (m, 2H), 2.24 (m, 1H), 1.98 (m, 2H), 1.79 (m, 2H), 1.12 (d, 3H)

EXAMPLE 17

Preparation of (2R,3R)-3-(4-(2,4-dichlorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.13 (s, 1H), 7.90 (s, 1H), 7.59 (m, 2H), 6.61 (m, 4H), 5.70 (bs, 1H), 4.87 (d, 1H), 4.80 (d, 1H), 4.18 (m, 1H), 2.95 (m, 2H), 2.52 (m, 2H), 2.24 (m, 1H), 1.98 (m, 2H), 1.79 (m, 2H), 1.10 (d, 3H)

EXAMPLE 18

Preparation of (2R,3R)-3-(4-(3,4-dichlorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.89 (s, 1H), 7.61 (m, 2H), 6.61 (m, 4H), 5.70 (bs, 1H), 4.87 (d, 1H), 4.80 (d, 1H), 4.18 (m, 1H), 2.93 (m, 2H), 2.36 (m, 2H), 2.24 (m, 1H), 1.98 (m, 2H), 1.79 (m, 2H), 1.12 (d, 3H)

EXAMPLE 19

Preparation of (2R,3R)-3-(4-(4-chloro-2-fluorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.90 (s, 1H), 762 (m, 2H), 6.81 (m, 4H), 5.70 (bs, 1H), 4.80 (d, 1H), 4.18 (m, 1H), 2.95 (m, 2H), 2.52 (m, 2H), 2.24 (m, 1H), 1.98 (m, 2H), 1.79 (m, 2H), 1.08 (d, 3H)

EXAMPLE 20

Preparation of (2R,3R)-3-(4-(2,4-difluorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.89 (s, 1H), 7.61 (m, 2H), 6.61 (m, 4H), 5.70 (bs, 1H), 4.87 (d, 1H), 4.80 (d, 1H), 4.18 (m, 1H), 2.94 (m, 2H), 2.31 (m, 2H), 2.24 (m, 1H), 1.98 (m, 2H), 1.79 (m, 2H), 1.10 (d, 3H)

EXAMPLE 21

Preparation of (2R,3R)-3-(4-(4-chloro-3-fluorophenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.99 (s, 1H), 7.72 (m, 2H), 6.61 (m, 4H), 5.70 (bs, 1H), 4.87 (d, 1H), 4.80 (d, 1H), 4.18 (m, 1H), 2.93 (m, 2H), 2.59 (m, 2H), 2.24 (m, 1H), 1.98 (m, 2H), 1.79 (m, 2H), 1.09 (d, 3H)

EXAMPLE 22

Preparation of (2R,3R)-3-(4-(4-chloro-2-methylphenoxy)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.99 (s, 1H), 7.42 (m, 2H), 6.91 (m, 4H), 5.70 (bs, 1H), 4.87 (d, 1H), 4.80 (d, 1H), 4.18 (m, 1H), 2.93 (m, 2H), 2.59 (m, 2H), 2.24 (m, 1H), 2.15 (s, 3H), 1.98 (m, 2H), 1.79 (m, 2H), 1.09 (d, 3H)

EXAMPLE 23

Preparation of (2R,3R)-2-(2,4-difluorophenyl)-3-(4-(pyridin-2-yloxy)piperidin-1-yl)-1-(1H-1,2,4-triazol-1-yl)butan-2-ol $^1$H-NMR (CDCl$_3$, 300 MHz) δ 8.32 (s, 1H), 7.98 (s, 1H), 7.66 (m, 3H), 6.94 (m, 4H), 5.70 (bs, 1H), 4.87 (d, 1H, J=14.4 Hz), 4.80 (d, 1H, J=15.2 Hz), 4.18 (m, 1H), 2.95 (m, 2H), 2.62 (m, 2H), 2.24 (m, 1H), 1.98 (m, 2H), 1.79 (m, 2H), 1.12 (d, 3H)

EXAMPLE 24

Preparation of (2R,3R)-2-(2,4-difluorophenyl)-3-(4-((5-methylpyridin-2-yl)oxy)piperidin-1-yl)-1-(1H-1,2,4-triazol-1-yl)butan-2-ol $^1$H-NMR (CDCl$_3$, 300 MHz) δ 8.30 (s, 1H), 7.91 (s, 1H), 7.42 (m, 2H), 6.94 (m, 4H), 5.70 (bs, 1H), 4.87 (d, 1H), 4.80 (d, 1H), 4.18 (m, 1H), 2.93 (m, 2H), 2.59 (m, 2H), 2.31 (s, 3H), 2.24 (m, 1H), 1.98 (m, 2H), 1.79 (m, 2H), 1.09 (d, 3H)

EXAMPLE 25

Preparation of (2R,3R)-2-(2,4-difluorophenyl)-3-(4-((5-fluoropyridin-2-yl)oxy)piperidin-1-yl)-1-(1H-1,2,4-triazol-1-yl)butan-2-ol $^1$H-NMR (CDCl$_3$, 300 MHz) δ 8.30 (s, 1H), 7.91 (s, 1H), 7.42 (m, 2H), 6.94 (m, 4H), 5.70 (bs, 1H), 4.87 (d, 1H), 4.80

(d, 1H), 4.18 (m, 1H), 2.93 (m, 2H), 2.59 (m, 2H), 2.24 (m, 1H), 1.98 (m, 2H), 1.79 (m, 2H), 1.09 (d, 3H)

EXAMPLE 26

Preparation of (2R,3R)-3-(4-((5-chloropyridin-2-yl)oxy)piperidin-1-yl)-2-(2,4-difluorophenyl)-1-(1H-1,2,4-triazol-1-yl)butan-2-ol $^1$H-NMR (CDCl$_3$, 300 MHz) δ 8.32 (s, 1H), 7.98 (s, 1H), 7.49 (m, 2H), 6.94 (m, 4H), 5.70 (bs, 1H), 4.87 (d, 1H), 4.80 (d, 1H), 4.18 (m, 1H), 2.93 (m, 2H), 2.62 (m, 2H), 2.24 (m, 1H), 1.98 (m, 2H), 1.79 (m, 2H), 1.12 (d, 3H)

EXAMPLE 27

Preparation of (2R,3R)-2-(2,4-difluorophenyl)-1-(1H-1,2,4-triazol-1-yl)-3-(4-((5-(trifluoromethyl)pyridin-2-yl)oxy)piperidin-1-yl)butan-2-ol $^1$H-NMR (CDCl$_3$, 300 MHz) δ 8.30 (s, 1H), 7.95 (s, 1H), 7.49 (m, 2H), 6.94 (m, 4H), 5.70 (bs, 1H), 4.87 (d, 1H), 4.80 (d, 1H), 4.18 (m, 1H), 2.97 (m, 2H), 2.65 (m, 2H), 2.24 (m, 1H), 1.98 (m, 2H), 1.79 (m, 2H), 1.13 (d, 3H)

EXAMPLE 28

Preparation of (2R,3R)-3-(4-((3-chloro-5-(trifluoromethyl)pyridin-2-yl)oxy)piperidin-1-yl)-2-(2,4-difluorophenyl)-1-(1H-1,2,4-triazol-1-yl)butan-2-ol $^1$H-NMR (CDCl$_3$, 300 MHz) δ 8.30 (s, 1H), 7.95 (s, 1H), 7.49 (m, 2H), 6.94 (m, 3H), 5.70 (bs, 1H), 4.87 (d, 1H), 4.80 (d, 1H), 4.18 (m, 1H), 2.97 (m, 2H), 2.65 (m, 2H), 2.24 (m, 1H), 1.98 (m, 2H), 1.79 (m, 2H), 1.13 (d, 3H)

EXAMPLE 29

Preparation of (2R,3R)-2-(2,4-difluorophenyl)-3-(4-(pyrimidin-2-yloxy)piperidin-1-yl)-1-(1H-1,2,4-triazol-1-yl)butan-2-ol $^1$H-NMR (CDCl$_3$, 300 MHz) δ 8.50 (s, 1H), 8.48 (s, 1H), 8.01 (s, 1H), 7.78 (s, 1H), 7.54-7.46 (m, 1H), 6.92-6.88 (m, 1H), 6.81-6.69 (m, 2H), 5.40 (bs, 1H), 4.88 (d, 1H), 4.81 (d, 1H), 3.06-2.99 (m, 1H), 2.97-2.90 (q, 2H), 2.66 (t, 2H), 2.36-2.28 (m, 1H), 2.08-2.02 (m, 2H), 1.94-1.83 (m, 2H), 1.01-0.97 (d, 3H)

EXAMPLE 30

Preparation of (2R,3R)-2-(2,4-difluorophenyl)-3-(4-((5-fluoropyrimidin-2-yl)oxy)piperidin-1-yl)-1-(1H-1,2,4-triazol-1-yl)butan-2-ol $^1$H-NMR (CDCl$_3$, 300 MHz) δ 8.51 (s, 1H), 7.90 (s, 1H), 7.78 (s, 2H), 7.49-7.47 (m, 1H), 6.75 (m, 2H), 4.84 (q, 2H), 3.01 (m, 2H), 2.65 (m, 2H), 2.30 (m, 1H), 1.91 (m, 4H), 0.98 (d, 3H)

EXAMPLE 31

Preparation of (2R,3R)-3-(4-((5-chloropyrimidin-2-yl)oxy)piperidin-1-yl)-2-(2,4-difluorophenyl)-1-(1H-1,2,4-triazol-1-yl)butan-2-ol $^1$H-NMR (CDCl$_3$, 300 MHz) δ 8.50 (s, 1H), 7.95 (s, 1H), 7.81 (s, 2H), 7.48 (m, 2H), 6.75 (m, 2H), 4.84 (q, 2H), 3.01 (m, 2H), 2.65 (m, 2H), 2.33 (m, 1H), 1.91 (m, 4H), 0.98 (d, 3H)

EXAMPLE 32

Preparation of (2R,3R)-3-(4-((5-bromopyrimidin-2-yl)oxy)piperidin-1-yl)-2-(2,4-difluorophenyl)-1-(1H-1,2,4-triazol-1-yl)butan-2-ol $^1$H-NMR (CDCl$_3$, 300 MHz) δ 8.50 (s, 1H), 7.99 (s, 1H), 7.78 (s, 2H), 7.49-7.47 (m, 1H), 6.77-6.73 (m, 2H), 4.85-4.84 (q, 2H), 3.02-2.91 (m, 2H), 2.67-2.63 (m, 2H), 2.30 (m, 1H), 2.02-1.81 (m, 4H), 0.96 (d, 3H)

EXAMPLE 33

Preparation of (2R,3R)-2-(2,4-difluorophenyl)-3-(4-((5-methylpyrimidin-2-yl)oxy)piperidin-1-yl)-1-(1H-1,2,4-triazol-1-yl)butan-2-ol $^1$H-NMR (CDCl$_3$, 300 MHz) δ 8.50 (s, 1H), 7.99 (s, 1H), 7.78 (s, 2H), 7.49-7.47 (m, 1H), 6.77-6.73 (m, 2H), 4.85-4.84 (q, 2H), 3.02-2.91 (m, 2H), 2.67-2.63 (m, 2H), 2.35 (s, 3H), 2.30 (m, 1H), 2.02-1.81 (m, 4H), 0.96 (d, 3H)

EXAMPLE 34

Preparation of (2R,3R)-3-(4-((4-chlorophenyl)amino)piperidin-1-yl)-2-(2,4-difluorophenyl)-1-(1H-1,2,4-triazol-1-yl)butan-2-ol

Step 1

Synthesis of tert-butyl-4-(4-chlorophenylamino)piperidine-1-carboxylate

To a solution of tert-butyl-4-oxopiperidine-1-carboxylate (1.0 g, 0.005 mmol) in tetrahydrofuran (16 mL) in a microwave reaction vessel were added 4-chloroaniline (640 mg, 0.005 mmol) and sodium triacetoxyboryhidride (3.2 g, 0.015 mmol), followed by irradiating the solution with microwaves at 80° C. for 10 min. The reaction was terminated by the addition of distilled water. The resulting reaction mixture was diluted in ethyl acetate (100 mL) and washed with distilled water (200 mL) to separate an organic solvent layer. The organic solvent layer was dried over anhydrous magnesium sulfate and evaporated at reduced pressure. Isolation and purification of the residue through silica gel chromatography produced tert-butyl-4-(4-chlorophenylamino)piperidine-1-carboxylate (yield: 65%).

Step 2

Synthesis of N-(4-chlorophenyl)piperidine-4-amine

The tert-butyl-4-(4-chlorophenylamino)piperidine-1-carboxylate (973.2 mg, 3.1 mmol) obtained in step 1 was dissolved in ethyl acetate and mixed at 0 C for 3 hr with 6N HCl (5 mL), with stirring, after which distilled water was added to terminate the reaction. The resulting reaction mixture was washed with ethyl acetate. The pH of the aqueous layer thus formed was adjusted to 10 to 12 with 2N sodium hydroxide, followed by washing with ethyl acetate and saline to separate an organic solvent layer. This organic solvent layer was dried over anhydrous magnesium sulfate and evaporated at reduced pressure to afford N-(4-chlorophenyl)piperidine-4-amine (yield 87%).

Step 3

Synthesis of (2R,3R)-3-(4-(4-chlorophenylamino) piperidin-1-yl)-2-(2,4-difluorophenyl)-1-(1H-1,2,4-triazol-1-yl)butan-2-ol To a solution of the N-(4-chlorophenyl)piperidine-4-amine (400.0 mg, 1.9 mmol) obtained in step 2 in acetonitrile were added lithium perchlorate (134.1 mg, 1.3 mmol) and 1-(((2R, 3R)-2-(2,4-difluorophenyl)-3-methyloxiran-2-yl)methyl)-1H-1,2,4-triazole (158.9 mg, 0.6 mmol), followed by irradiating microwaves onto the solution at 150° C. for 30 min. After removal of the solvent, the reaction mixture was diluted in ethyl acetate and washed with distilled water and saline to separate an organic solvent layer. The organic solvent layer was dried over anhydrous magnesium sulfate and concentrated in a vacuum. Isolation and purification of the concentrate through silica gel chromatography afforded the title compound (yield 31%).

$^1$H-NMR (CDCl$_3$, 300 MHz) δ 7.99 (s, 1H), 7.78 (s, 1H), 7.49-7.45 (m, 1H), 7.09 (d, 2H), 6.80-6.70 (m, 2H), 6.47 (d, 2H), 4.88-4.76 (q, 2H), 3.19-3.17 (m, 1H), 2.94-2.89 (m, 2H), 2.67-2.64 (m, 2H), 2.22-2.20 (m, 1H), 2.08-1.96 (m, 3H), 0.97 (d, 3H, J=7.0 Hz).

Compounds of Examples 35 to 88 were synthesized in similar manners to the method of Example 34.

EXAMPLE 35

Preparation of (2R,3R)-2-(2,4-difluorophenyl)-3-(4-(phenylamino)piperidin-1-yl)-1-(1H-1,2,4-triazol-1-yl)butan-2-ol $^1$H-NMR (CDCl$_3$, 300 MHz) δ 7.99 (s, 1H), 7.78 (s, 1H), 7.48 (m, 2H), 7.09 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.01 (m, 3H), 0.97 (d, 3H)

EXAMPLE 36

Preparation of (2R,3R)-2-(2,4-difluorophenyl)-3-(4-((2-fluorophenyl)amino)piperidin-1-yl)-1-(1H-1,2,4-triazol-1-yl)butan-2-ol $^1$H-NMR (CDCl$_3$, 300 MHz) δ 8.01 (s, 1H), 7.78 (s, 1H), 7.48 (m, 1H), 7.09 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.01 (m, 3H), 0.97 (d, 3H)

EXAMPLE 37

Preparation of (2R,3R)-2-(2,4-difluorophenyl)-3-(4-((3-fluorophenyl)amino)piperidin-1-yl)-1-(1H-1,2,4-triazol-1-yl)butan-2-ol $^1$H-NMR (CDCl$_3$, 300 MHz) δ 8.01 (s, 1H), 7.79 (s, 1H), 7.51 (m, 1H), 7.09 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.01 (m, 3H), 0.98 (d, 3H)

EXAMPLE 38

Preparation of (2R,3R)-2-(2,4-difluorophenyl)-3-(4-((4-fluorophenyl)amino)piperidin-1-yl)-1-(1H-1,2,4-triazol-1-yl)butan-2-ol $^1$H-NMR (CDCl$_3$, 300 MHz) δ 8.01 (s, 1H), 7.78 (s, 1H), 7.48 (m, 1H), 7.11 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.01 (m, 3H), 0.98 (d, 3H)

EXAMPLE 39

Preparation of (2R,3R)-3-(4-((2-chlorophenyl) amino)piperidin-1-yl)-2-(2,4-difluorophenyl)-1-(1H-1,2,4-triazol-1-yl)butan-2-ol $^1$H-NMR (CDCl$_3$, 300 MHz) δ 8.00 (s, 1H), 7.79 (s, 1H), 7.48 (m, 1H), 7.09 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.01 (m, 3H), 0.99 (d, 3H)

EXAMPLE 40

Preparation of (2R,3R)-3-(4-((3-chlorophenyl) amino)piperidin-1-yl)-2-(2,4-difluorophenyl)-1-(1H-1,2,4-triazol-1-yl)butan-2-ol $^1$H-NMR (CDCl$_3$, 300 MHz) δ 8.01 (s, 1H), 7.79 (s, 1H), 7.52 (m, 1H), 7.09 (d, 2H), 6.75 (m, 2H), 6.47 (d, 2H), 4.81 (q, 2H), 3.18 (m, 1H), 2.90 (m, 2H), 2.67-2.64 (m, 2H), 2.21 (m, 1H), 2.00 (m, 3H), 0.99 (d, 3H)

EXAMPLE 41

Preparation of (2R,3R)-3-(4-((2-bromophenyl) amino)piperidin-1-yl)-2-(2,4-difluorophenyl)-1-(1H-1,2,4-triazol-1-yl)butan-2-ol $^1$H-NMR (CDCl$_3$, 300 MHz) δ 8.05 (s, 1H), 781 (s, 1H), 7.48 (m, 1H), 7.09 (d, 2H), 6.75 (m, 2H), 6.47 (d, 2H), 4.81 (q, 2H), 3.18 (m, 1H), 2.90 (m, 2H), 2.64 (m, 2H), 2.21 (m, 1H), 2.01 (m, 3H), 0.98 (d, 3H)

EXAMPLE 42

Preparation of (2R,3R)-3-(4-((3-bromophenyl) amino)piperidin-1-yl)-2-(2,4-difluorophenyl)-1-(1H-1,2,4-triazol-1-yl)butan-2-ol $^1$H-NMR (CDCl$_3$, 300 MHz) δ 8.05 (s, 1H), 7.82 (s, 1H), 7.52 (m, 1H), 7.09 (d, 2H), 6.75 (m, 2H), 6.47 (d, 2H), 4.81 (q, 2H), 3.18 (m, 1H), 2.90 (m, 2H), 2.66 (m, 2H), 2.21 (m, 1H), 2.00 (m, 3H), 0.98 (d, 3H)

EXAMPLE 43

Preparation of (2R,3R)-3-(4-((4-bromophenyl) amino)piperidin-1-yl)-2-(2,4-difluorophenyl)-1-(1H-1,2,4-triazol-1-yl)butan-2-ol $^1$H-NMR (CDCl$_3$, 300 MHz) δ 8.04 (s, 1H), 7.82 (s, 1H), 7.51 m, 1H), 7.09 (d, 2H), 6.75 (m, 2H), 6.47 (d, 2H), 4.83 (q, 2H), 3.18 (m, 1H), 2.90 (m, 2H), 2.66 (m, 2H), 2.21 (m, 1H), 2.01 (m, 3H), 0.98 (d, 3H)

EXAMPLE 44

Preparation of (2R,3R)-2-(2,4-difluorophenyl)-1-(1H-1,2,4-triazol-1-yl)-3-(4-((2-(trifluoromethyl)phenyl)amino)piperidin-1-yl)butan-2-ol $^1$H-NMR (CDCl$_3$, 300 MHz) δ 7.98 (s, 1H), 7.75 (s, 1H), 7.51 m, 1H), 7.10 (d, 2H), 6.75 (m, 2H), 6.47 (d, 2H), 4.83 (q, 2H), 3.18 (m, 1H), 2.90 (m, 2H), 2.66 (m, 2H), 2.21 (m, 1H), 1.96 (m, 3H), 0.98 (d, 3H)

EXAMPLE 45

Preparation of (2R,3R)-2-(2,4-difluorophenyl)-1-(1H-1,2,4-triazol-1-yl)-3-(4-((3-(trifluoromethyl)phenyl)amino)piperidin-1-yl)butan-2-ol $^1$H-NMR (CDCl$_3$, 300 MHz) δ 7.98 (s, 1H), 7.76 (s, 1H), 7.51 m, 1H), 7.10 (d, 2H), 6.75 (m, 2H), 6.47 (d, 2H), 4.83 (q, 2H), 3.18 (m, 1H), 2.90 (m, 2H), 2.65 (m, 2H), 2.21 (m, 1H), 1.98 (m, 3H), 0.98 (d, 3H)

EXAMPLE 46

Preparation of (2R,3R)-2-(2,4-difluorophenyl)-1-(1H-1,2,4-triazol-1-yl)-3-(4-((4-(trifluoromethyl)phenyl)amino)piperidin-1-yl)butan-2-ol $^1$H-NMR (CDCl$_3$, 300 MHz) δ 7.98 (s, 1H), 7.74 (s, 1H), 7.51 m, 1H), 7.10 (d, 2H), 6.75 (m, 2H), 6.47 (d, 2H), 4.83 (q, 2H), 3.18 (m, 1H), 2.90 (m, 2H), 2.67 (m, 2H), 2.23 (m, 1H), 1.97 (m, 3H), 0.99 (d, 3H)

EXAMPLE 47

Preparation of 2-((1-((2R,3R)-3-(2,4-difluorophenyl)-3-hydroxy-4-(1H-1,2,4-triazol-1-yl)butan-2-yl)piperidin-4-yl)amino)benzonitrile $^1$H-NMR (CDCl$_3$, 300 MHz) δ 8.05 (s, 1H), 7.74 (s, 1H), 7.61 m, 1H), 7.22 (d, 2H), 6.75 (m, 2H), 6.51 (d, 2H), 4.93 (q, 2H), 3.18 (m, 1H), 2.90 (m, 2H), 2.67 (m, 2H), 2.23 (m, 1H), 1.97 (m, 3H), 1.10 (d, 3H)

EXAMPLE 48

Preparation of 3-((1-((2R,3R)-3-(2,4-difluorophenyl)-3-hydroxy-4-(1H-1,2,4-triazol-1-yl)butan-2-yl)piperidin-4-yl)amino)benzonitrile $^1$H-NMR (CDCl$_3$, 300 MHz) δ 8.04 (s, 1H), 7.74 (s, 1H), 7.61 m, 1H), 7.22 (d, 2H), 6.75 (m, 2H), 6.51 (d, 2H), 4.93 (q, 2H), 3.18 (m, 1H), 2.90 (m, 2H), 2.65 (m, 2H), 2.23 (m, 1H), 1.99 (m, 3H), 1.09 (d, 3H)

EXAMPLE 49

Preparation of 4-((1-((2R,3R)-3-(2,4-difluorophenyl)-3-hydroxy-4-(1H-1,2,4-triazol-1-yl)butan-2-yl)piperidin-4-yl)amino)benzonitrile $^1$H-NMR (CDCl$_3$, 300 MHz) δ 8.05 (s, 1H), 7.74 (s, 1H), 7.51 m, 1H), 7.31 (d, 2H), 6.75 (m, 2H), 6.51 (d, 2H), 4.93 (q, 2H), 3.18 (m, 1H), 2.90 (m, 2H), 2.67 (m, 2H), 2.23 (m, 1H), 1.97 (m, 3H), 1.09 (d, 3H)

EXAMPLE 50

Preparation of (2R,3R)-3-(4-((2,4-dichlorophenyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.03 (s, 1H), 7.74 (s, 1H), 7.61 m, 1H), 7.22 (d, 2H), 6.75 (m, 1H), 6.51 (d, 2H), 4.93 (q, 2H), 3.18 (m, 1H), 2.90 (m, 2H), 2.65 (m, 2H), 2.23 (m, 1H), 1.99 (m, 3H), 1.00 (d, 3H)

EXAMPLE 51

Preparation of (2R,3R)-3-(4-((3,4-dichlorophenyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.03 (s, 1H), 7.78 (s, 1H), 7.61 m, 1H), 7.22 (d, 2H), 6.75 (m, 1H), 6.51 (d, 2H), 4.93 (q, 2H), 3.18 (m, 1H), 2.90 (m, 2H), 2.65 (m, 2H), 2.23 (m, 1H), 1.99 (m, 3H), 1.02 (d, 3H)

EXAMPLE 52

Preparation of (2R,3R)-3-(4-((4-chloro-2-fluorophenyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.03 (s, 1H), 7.74 (s, 1H), 7.61 m, 1H), 7.22 (d, 2H), 6.75 (m, 1H), 6.51 (d, 2H), 4.95 (q, 2H), 3.18 (m, 1H), 2.90 (m, 2H), 2.65 (m, 2H), 2.23 (m, 1H), 1.99 (m, 3H), 0.99 (d, 3H)

EXAMPLE 53

Preparation of (2R,3R)-2-(2,4-difluorophenyl)-3-(4-((2,4-difluorophenyl)amino)piperidin-1-yl)-1-(1H-1,2,4-triazol-1-yl)butan-2-ol $^1$H-NMR (CDCl$_3$, 300 MHz) δ 8.02 (s, 1H), 7.74 (s, 1H), 7.63 (m, 1H), 7.21 (d, 2H), 6.75 (m, 1H), 6.51 (d, 2H), 4.95 (q, 2H), 3.18 (m, 1H), 2.93 (m, 2H), 2.65 (m, 2H), 2.23 (m, 1H), 1.99 (m, 3H), 0.98 (d, 3H)

EXAMPLE 54

Preparation of (2R,3R)-3-(4-((4-chloro-3-fluorophenyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.03 (s, 1H), 7.74 (s, 1H), 7.61 m, 1H), 7.22 (d, 2H), 6.75 (m, 1H), 6.53 (d, 2H), 4.95 (q, 2H), 3.18 (m, 1H), 2.90 (m, 2H), 2.64 (m, 2H), 2.23 (m, 1H), 1.99 (m, 3H), 0.99 (d, 3H)

EXAMPLE 55

Preparation of (2R,3R)-3-(4-((4-chloro-2-methylphenyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.01 (s, 1H), 7.74 (s, 1H), 7.61 m, 1H), 7.22 (d, 2H), 6.75 (m, 1H), 6.53 (d, 2H), 4.95 (q, 2H), 3.18 (m, 1H), 2.90 (m, 2H), 2.64 (m, 2H), 2.23 (m, 1H), 2.12 (s, 3H), 1.99 (m, 3H), 0.99 (d, 3H)

EXAMPLE 56

Preparation of (2R,3R)-2-(2,4-difluorophenyl)-3-(4-(pyridin-2-ylamino)piperidin-1-yl)-1-(1H-1,2,4-triazol-1-yl)butan-2-ol ¹H-NMR (CDCl$_3$, 300 MHz) δ 8.11 (s, 1H), 8.05 (s, 1H), 7.81 (m, 1H), 7.22 (d, 2H), 6.75 (m, 2H), 6.53 (d, 2H), 4.95 (q, 2H), 3.18 (m, 1H), 2.90 (m, 2H), 2.64 (m, 2H), 2.43 (m, 1H), 2.12 (s, 3H), 2.03 (m, 3H), 1.10 (d, 3H)

EXAMPLE 57

Preparation of (2R,3R)-2-(2,4-difluorophenyl)-3-(4-((5-methylpyridin-2-yl)amino)piperidin-1-yl)-1-(1H-1,2,4-triazol-1-yl)butan-2-ol ¹H-NMR (CDCl$_3$, 300 MHz) δ 8.11 (s, 1H), 7.74 (s, 1H), 7.61 (m, 1H), 7.22 (d, 2H), 6.75 (m, 1H), 6.53 (d, 2H), 4.95 (q, 2H), 3.18 (m, 1H), 2.90 (m, 2H), 2.64 (m, 2H), 2.43 (m, 1H), 2.31 (s, 3H), 1.99 (m, 3H), 1.10 (d, 3H)

EXAMPLE 58

Preparation of (2R,3R)-2-(2,4-difluorophenyl)-3-(4-((5-fluoropyridin-2-yl)amino)piperidin-1-yl)-1-(1H-1,2,4-triazol-1-yl)butan-2-ol ¹H-NMR (CDCl$_3$, 300 MHz) δ 8.05 (s, 1H), 7.87 (s, 1H), 7.46 (m, 1H), 7.32 (d, 2H), 6.73 (m, 2H), 6.30 (d, 1H), 4.81 (q, 2H), 4.34 (d, 1H), 3.56 (m, 1H), 2.91 (m, 2H), 268 (m, 2H), 2.24 (m, 1H), 2.01 (m, 2H), 1.45 (m, 3H), 0.96 (d, 2H)

EXAMPLE 59

Preparation of (2R,3R)-3-(4-((5-chloropyridin-2-yl)-amino)piperidin-1-yl)-2-(2,4-difluorophenyl)-1-(1H-1,2,4-triazol-1-yl)butan-2-ol ¹H-NMR (CDCl$_3$, 300 MHz) δ 7.97 (s, 1H), 7.77 (s, 1H), 7.48-7.45 (m, 1H), 7.34-7.30 (d, 2H), 6.75-6.72 (m, 2H), 6.30-6.27 (d, 1H), 4.83-4.80 (q, 2H), 4.38-4.35 (d, 1H), 3.58-3.55 (m, 1H), 2.93-2.89 (m, 2H), 2.69-2.63 (m, 2H), 2.25-2.22 (m, 1H), 2.06-1.93 (m, 2H), 1.53-1.38 (m, 3H), 0.96 (d, 2H)

EXAMPLE 60

Preparation of (2R,3R)-3-(4-((3-chloro-5-(trifluoromethyl)pyridin-2-yl)amino)piperidin-1-yl)-2-(2,4-difluorophenyl)-1-(1H-1,2,4-triazol-1-yl)butan-2-ol ¹H-NMR (CDCl$_3$, 300 MHz) δ 8.03 (s, 1H), 7.82 (s, 1H), 7.46 (m, 1H), 7.32 (d, 2H), 6.73 (m, 1H), 6.3 (d, 1H), 4.81 (q, 2H), 4.34 (d, 1H), 3.56 (m, 1H), 2.91 (m, 2H), 268 (m, 2H), 2.24 (m, 1H), 2.01 (m, 2H), 1.45 (m, 3H), 0.97 (d, 2H)

EXAMPLE 61

Preparation of (2R,3R)-2-(2,4-difluorophenyl)-1-(1H-1,2,4-triazol-1-yl)-3-(4-((5-(trifluoromethyl)pyridin-2-yl)amino)piperidin-1-yl)butan-2-ol ¹H-NMR (CDCl$_3$, 300 MHz) δ 7.99 (s, 1H), 7.94 (s, 1H), 7.79 (s, 1H), 7.48 (m, 1H), 7.19 (m, 1H), 6.76 (m, 2H), 6.33 (m, 1H), 4.83 (q, 1H), 4.36 (m, 1H), 3.53 (m, 1H), 2.91 (m, 2H), 2.70 (m, 2H), 2.23 (m, 1H), 2.03 (m, 4H), 0.99 (d, 3H)

EXAMPLE 62

Preparation of (2R,3R)-2-(2,4-difluorophenyl)-3-(4-(pyrimidin-2-ylamino)piperidin-1-yl)-1-(1H-1,2,4-triazol-1-yl)butan-2-ol ¹H-NMR (CDCl$_3$, 300 MHz) δ 8.00 (s, 1H), 7.92 (s, 1H), 7.78 (s, 1H), 7.48 (m, 1H), 7.19 (m, 1H), 6.76 (m, 2H), 6.30 (m, 1H), 4.83 (q, 1H), 4.36 (m, 1H), 3.53 (m, 1H), 2.91 (m, 2H), 2.70 (m, 2H), 2.23 (m, 1H), 2.03 (m, 4H), 0.98 (d, 3H)

EXAMPLE 63

Preparation of (2R,3R)-2-(2,4-difluorophenyl)-3-(4-((5-fluoropyrimidin-2-yl)amino)piperidin-1-yl)-1-(1H-1,2,4-triazol-1-yl)butan-2-ol ¹H-NMR (CDCl$_3$, 300 MHz) δ 7.99 (s, 1H), 7.92 (s, 1H), 7.78 (s, 1H), 7.49-7.45 (m, 1H), 7.21-7.17 (m, 1H), 6.79-6.73 (m, 2H), 4.84-4.81 (q, 1H), 4.38-4.35 (m, 1H), 3.54-3.52 (m, 1H), 2.93-2.91 (m, 2H), 2.70-2.62 (m, 2H), 2.25-2.24 (m, 1H), 2.08-1.96 (m, 4H), 0.97 (d, 3H)

EXAMPLE 64

Preparation of (2R,3R)-3-(4-((5-bromopyrimidin-2-yl)-amino)piperidin-1-yl)-2-(2,4-difluorophenyl)-1-(1H-1,2,4-triazol-1-yl)butan-2-ol ¹H-NMR (CDCl$_3$, 300 MHz) δ 8.01 (s, 1H), 7.93 (s, 1H), 7.78 (s, 1H), 7.48 (m, 1H), 7.19 (m, 1H), 6.76 (m, 2H), 4.83 (q, 1H), 4.36 (m, 1H), 3.53 (m, 1H), 2.91 (m, 2H), 2.70 (m, 2H), 2.23 (m, 1H), 2.03 (m, 4H), 0.99 (d, 3H)

EXAMPLE 65

Preparation of (2R,3R)-3-(4-((5-chloropyrimidin-2-yl)amino)piperidin-1-yl)-2-(2,4-difluorophenyl)-1-(1H-1,2,4-triazol-1-yl)butan-2-ol ¹H-NMR (CDCl$_3$, 300 MHz) δ 8.00 (s, 1H), 7.93 (s, 1H), 7.78 (s, 1H), 7.48 (m, 1H), 7.19 (m, 1H), 6.76 (m, 2H), 4.83 (q, 1H), 4.36 (m, 1H), 3.53 (m, 1H), 2.91 (m, 2H), 2.70 (m, 2H), 2.30 (m, 1H), 2.03 (m, 4H), 0.98 (d, 3H)

EXAMPLE 66

Preparation of (2R,3R)-2-(2,4-difluorophenyl)-3-(4-((5-methylpyrimidin-2-yl)amino)piperidin-1-yl)-1-(1H-1,2,4-triazol-1-yl)butan-2-ol ¹H-NMR (CDCl$_3$, 300 MHz) δ 8.41 (s, 1H), 8.06 (s, 1H), 7.98 (s, 1H), 7.48 (m, 1H), 7.19 (m, 1H), 6.91 (m, 2H), 4.83 (q, 1H), 4.36 (m, 1H), 3.53 (m, 1H), 2.91 (m, 2H), 2.70 (m, 2H), 2.34 (s, 3H), 2.23 (m, 1H), 2.03 (m, 4H), 1.12 (d, 3H)

EXAMPLE 67

Preparation of (2R,3R)-2-(2,4-difluorophenyl)-3-(4-(methyl(phenyl)amino)piperidin-1-yl)-1-(1H-1,2,4-triazol-1-yl)butan-2-ol ¹H-NMR (CDCl$_3$, 300 MHz) δ 8.01 (s, 1H), 7.91 (s, 1H), 7.48 (m, 2H), 7.09 (d, 2H), 6.75 (m, 2H), 6.47 (d, 2H), 4.81 (q, 2H), 3.18 (m, 1H), 2.90 (m, 2H), 2.70 (s, 3H), 2.67-2.64 (m, 2H), 2.21 (m, 1H), 2.01 (m, 4H), 0.99 (d, 3H)

EXAMPLE 68

Preparation of (2R,3R)-2-(2,4-difluorophenyl)-3-(4-((2-fluorophenyl)(methyl)amino)piperidin-1-yl)-1-(1H-1,2,4-triazol-1-yl)butan-2-ol $^1$H-NMR (CDCl$_3$, 300 MHz) δ 8.02 (s, 1H), 7.91 (s, 1H), 7.51 (m, 1H), 7.09 (d, 2H), 6.75 (m, 2H), 6.47 (d, 2H), 4.81 (q, 2H), 3.18 (m, 1H), 2.90 (m, 2H), 2.70 (s, 3H), 2.67-2.64 (m, 2H), 2.21 (m, 1H), 2.01 (m, 4H), 1.01 (d, 3H)

EXAMPLE 69

Preparation of (2R,3R)-2-(2,4-difluorophenyl)-3-(4-((3-fluorophenyl)(methyl)amino)piperidin-1-yl)-1-(1H-1,2,4-triazol-1-yl)butan-2-ol $^1$H-NMR (CDCl$_3$, 300 MHz) δ 8.02 (s, 1H), 7.91 (s, 1H), 7.51 (m, 1H), 7.09 (d, 2H), 6.75 (m, 2H), 6.47 (d, 2H), 4.81 (q, 2H), 3.18 (m, 1H), 2.91 (m, 2H), 2.70 (s, 3H), 2.67-2.64 (m, 2H), 2.21 (m, 1H), 2.01 (m, 4H), 1.01 (d, 3H)

EXAMPLE 70

Preparation of (2R,3R)-2-(2,4-difluorophenyl)-3-(4-((4-fluorophenyl)(methyl)amino)piperidin-1-yl)-1-(1H-1,2,4-triazol-1-yl)butan-2-ol $^1$H-NMR (CDCl$_3$, 300 MHz) δ 8.02 (s, 1H), 7.93 (s, 1H), 7.51 (m, 1H), 7.09 (d, 2H), 6.75 (m, 2H), 6.47 (d, 2H), 4.82 (q, 2H), 3.18 (m, 1H), 2.91 (m, 2H), 2.72 (s, 3H), 2.65 (m, 2H), 2.21 (m, 1H), 2.01 (m, 4H), 1.00 (d, 3H)

EXAMPLE 71

Preparation of (2R,3R)-3-(4-((2-chlorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.03 (s, 1H), 7.91 (s, 1H), 7.51 (m, 1H), 7.09 (d, 2H), 6.77 (m, 2H), 6.49 (d, 2H), 4.81 (q, 2H), 3.18 (m, 1H), 2.90 (m, 2H), 2.70 (s, 3H), 2.66 (m, 2H), 2.21 (m, 1H), 2.01 (m, 4H), 1.01 (d, 3H)

EXAMPLE 72

Preparation of (2R,3R)-3-(4-((3-chlorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.02 (s, 1H), 7.91 (s, 1H), 7.51 (m, 1H), 7.09 (d, 2H), 6.76 (m, 2H), 6.47 (d, 2H), 4.81 (q, 2H), 3.18 (m, 1H), 2.90 (m, 2H), 2.70 (s, 3H), 2.67 (m, 2H), 2.21 (m, 1H), 2.01 (m, 4H), 1.01 (d, 3H)

EXAMPLE 73

Preparation of (2R,3R)-3-(4-((4-chlorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.02 (s, 1H), 7.93 (s, 1H), 7.51 (m, 1H), 7.09 (d, 2H), 6.75 (m, 2H), 6.47 (d, 2H), 4.82 (q, 2H), 3.18 (m, 1H), 2.91 (m, 2H), 2.72 (s, 3H), 2.65 (m, 2H), 2.21 (m, 1H), 2.01 (m, 4H), 1.01 (d, 3H)

EXAMPLE 74

Preparation of (2R,3R)-3-(4-β2-bromophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.93 (s, 1H), 7.51 (m, 1H), 7.09 (d, 2H), 6.77 (m, 2H), 6.49 (d, 2H), 4.81 (q, 2H), 3.18 (m, 1H), 2.90 (m, 2H), 2.75 (s, 3H), 2.66 (m, 2H), 2.21 (m, 1H), 2.01 (m, 4H), 1.12 (d, 3H)

EXAMPLE 75

Preparation of (2R,3R)-3-(4-((3-bromophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.92 (s, 1H), 7.59 (m, 1H), 7.39 (d, 2H), 6.76 (m, 2H), 6.47 (d, 2H), 4.81 (q, 2H), 3.18 (m, 1H), 2.90 (m, 2H), 2.73 (s, 3H), 2.67 (m, 2H), 2.21 (m, 1H), 2.01 (m, 4H), 1.11 (d, 3H)

EXAMPLE 76

Preparation of (2R,3R)-3-(4-((4-bromophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.12 (s, 1H), 7.93 (s, 1H), 7.53 (m, 1H), 7.39 (d, 2H), 6.75 (m, 2H), 6.47 (d, 2H), 4.82 (q, 2H), 3.18 (m, 1H), 2.91 (m, 2H), 2.74 (s, 3H), 2.65 (m, 2H), 2.21 (m, 1H), 2.01 (m, 4H), 1.12 (d, 3H)

EXAMPLE 77

Preparation of (2R,3R)-2-(2,4-difluorophenyl)-3-(4-(methyl(2-(trifluoromethyl)phenyl)amino)piperidin-1-yl)-1-(1H-1,2,4-triazol-1-yl)butan-2-ol $^1$H-NMR (CDCl$_3$, 300 MHz) δ 8.05 (s, 1H), 7.93 (s, 1H), 7.51 (m, 1H), 7.09 (d, 2H), 6.77 (m, 2H), 6.49 (d, 2H), 4.81 (q, 2H), 3.18 (m, 1H), 2.90 (m, 2H), 2.59 (s, 3H), 2.43 (m, 2H), 2.21 (m, 1H), 2.01 (m, 4H), 1.08 (d, 3H)

EXAMPLE 78

Preparation of (2R,3R)-2-(2,4-difluorophenyl)-3-(4-(methyl(3-(trifluoromethyl)phenyl)amino)piperidin-1-yl)-1-(1H-1,2,4-triazol-1-yl)butan-2-ol $^1$H-NMR (CDCl$_3$, 300 MHz) δ 8.05 (s, 1H), 7.92 (s, 1H), 7.59 (m, 1H), 7.39 (d, 2H), 6.76 (m, 2H), 6.47 (d, 2H), 4.81 (q, 2H), 3.18 (m, 1H), 2.90 (m, 2H), 2.59 (s, 3H), 2.42 (m, 2H), 2.21 (m, 1H), 2.01 (m, 4H), 1.07 (d, 3H)

EXAMPLE 79

Preparation of (2R,3R)-2-(2,4-difluorophenyl)-3-(4-(methyl(4-(trifluoromethyl)phenyl)amino)piperidin-1-yl)-1-(1H-1,2,4-triazol-1-yl)butan-2-ol $^1$H-NMR (CDCl$_3$, 300 MHz) δ 8.06 (s, 1H), 7.93 (s, 1H), 7.53 (m, 1H), 7.39 (d, 2H), 6.75 (m, 2H), 6.47 (d, 2H), 4.82 (q, 2H), 3.18 (m, 1H), 2.91 (m, 2H), 2.59 (s, 3H), 2.41 (m, 2H), 2.21 (m, 1H), 2.01 (m, 4H), 1.08 (d, 3H)

EXAMPLE 80

Preparation of 2-((1-((2R,3R)-3-(2,4-difluorophenyl)-3-hydroxy-4-(1H-1,2,4-triazol-1-yl)butan-2-yl)piperidin-4-yl)(methyl)amino)benzonitrile $^1$H-NMR (CDCl$_3$, 300 MHz) δ 8.01 (s, 1H), 7.90 (s, 1H), 7.45 (m, 1H), 7.02 (d, 2H), 6.77 (m, 2H), 6.49 (d, 2H), 4.81 (q, 2H), 3.18 (m, 1H), 2.90 (m, 2H), 2.59 (s, 3H), 2.43 (m, 2H), 2.21 (m, 1H), 2.01 (m, 4H), 1.00 (d, 3H)

EXAMPLE 81

Preparation of 3-((1-((2R,3R)-3-(2,4-difluorophenyl)-3-hydroxy-4-(1H-1,2,4-triazol-1-yl)butan-2-yl)piperidin-4-yl)(methyl)amino)benzonitrile $^1$H-NMR (CDCl$_3$, 300 MHz) δ 7.99 (s, 1H), 7.90 (s, 1H), 7.45 (m, 1H), 7.02 (d, 2H), 6.56 (m, 2H), 6.32 (d, 2H), 4.81 (q, 2H), 3.18 (m, 1H), 2.90 (m, 2H), 2.55 (s, 3H), 2.42 (m, 2H), 2.21 (m, 1H), 2.01 (m, 4H), 0.98 (d, 3H)

EXAMPLE 82

Preparation of 4-((1-((2R,3R)-3-(2,4-difluorophenyl)-3-hydroxy-4-(1H-1,2,4-triazol-1-yl)butan-2-yl)piperidin-4-yl)(methyl)amino)benzonitrile $^1$H-NMR (CDCl$_3$, 300 MHz) δ 8.01 (s, 1H), 7.89 (s, 1H), 7.51 (m, 1H), 7.39 (d, 2H), 6.75 (m, 2H), 6.47 (d, 2H), 4.82 (q, 2H), 3.18 (m, 1H), 2.91 (m, 2H), 2.57 (s, 3H), 2.41 (m, 2H), 2.21 (m, 1H), 2.01 (m, 4H), 0.99 (d, 3H)

EXAMPLE 83

Preparation of (2R,3R)-3-(4-((2,4-dichlorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.11 (s, 1H), 8.01 (s, 1H), 7.78 (m, 1H), 7.45 (d, 2H), 6.95 (m, 1H), 6.51 (d, 2H), 4.91 (q, 2H), 3.18 (m, 1H), 2.91 (m, 2H), 2.57 (s, 3H), 2.41 (m, 2H), 2.21 (m, 1H), 2.01 (m, 4H), 0.99 (d, 3H)

EXAMPLE 84

Preparation of (2R,3R)-3-(4-((3,4-dichlorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.11 (s, 1H), 7.89 (s, 1H), 7.51 (m, 1H), 7.39 (d, 2H), 6.75 (m, 1H), 6.47 (d, 2H), 4.82 (q, 2H), 3.18 (m, 1H), 2.91 (m, 2H), 2.57 (s, 3H), 2.41 (m, 2H), 2.21 (m, 1H), 2.01 (m, 4H), 1.01 (d, 3H)

EXAMPLE 85

Preparation of (2R,3R)-3-(4-((4-chloro-2-fluorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.08 (s, 1H), 7.93 (s, 1H), 7.51 (m, 1H), 7.39 (d, 2H), 6.75 (m, 1H), 6.57 (d, 2H), 4.82 (q, 2H), 3.18 (m, 1H), 2.91 (m, 2H), 2.57 (s, 3H), 2.41 (m, 2H), 2.21 (m, 1H), 2.01 (m, 4H), 1.00 (d, 3H)

EXAMPLE 86

Preparation of (2R,3R)-2-(2,4-difluorophenyl)-3-(4-((2,4-difluorophenyl)(methyl)amino)piperidin-1-yl)-1-(1H-1,2,4-triazol-1-yl)butan-2-ol $^1$H-NMR (CDCl$_3$, 300 MHz) δ 8.09 (s, 1H), 7.89 (s, 1H), 7.51 (m, 1H), 7.39 (d, 2H), 6.75 (m, 1H), 6.51 (d, 2H), 4.88 (q, 2H), 3.18 (m, 1H), 2.91 (m, 2H), 2.57 (s, 3H), 2.41 (m, 2H), 2.21 (m, 1H), 2.01 (m, 4H), 0.98 (d, 3H)

EXAMPLE 87

Preparation of (2R,3R)-3-(4-((4-chloro-3-fluorophenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.11 (s, 1H), 7.99 (s, 1H), 7.71 (m, 1H), 7.39 (d, 2H), 6.75 (m, 1H), 6.57 (d, 2H), 4.91 (q, 2H), 3.18 (m, 1H), 2.94 (m, 2H), 2.57 (s, 3H), 2.41 (m, 2H), 2.21 (m, 1H), 2.01 (m, 4H), 0.99 (d, 3H)

EXAMPLE 88

Preparation of (2R,3R)-3-(4-((4-chloro-2-methylphenyl)(methyl)amino)piperidin-1-yl)-2-(2,4-difluorophenyl)-1-(1H-1,2,4-triazol-1-yl)butan-2-ol $^1$H-NMR (CDCl$_3$, 300 MHz) δ 8.11 (s, 1H), 7.89 (s, 1H), 7.51 (m, 1H), 7.39 (d, 2H), 6.75 (m, 1H), 6.47 (d, 2H), 4.82 (q, 2H), 3.18 (m, 1H), 2.91 (m, 2H), 2.57 (s, 3H), 2.41 (m, 2H), 2.21 (m, 1H), 2.01 (m, 4H), 0.99 (d, 3H)

EXAMPLE 89

Preparation of (2R,3R)-2-(2,4-difluorophenyl)-3-((1-(pyrimidin-2-yl)piperidin-4-yl)oxy)-1-(1H-1,2,4-triazol-1-yl)butan-2-ol To a solution of 1-(pyrimidin-2-yl)piperidin-4-ol (19.4 mg, 0.08 mmol) in N,N-dimethylformamide (0.5 mL) was added potassium tert-butoxide (10.7 mg, 0.01 mmol), followed by stirring at room temperature for 2 hrs. The resulting solution was mixed with 1-(((2R,3R)-2-(2,4-difluorophenyl)-3-methyloxiran-2-yl)methyl)-1H-1,2,4-triazole (20.0 mg, 0.08 mmol) and anhydrous potassium carbonate (13.2 mg, 0.01 mmol) and stirred at room temperature for one hr. The resulting reaction mixture was diluted with ethyl acetate, and washed with a saturated aqueous ammonium chloride solution and then with saline to separate an organic solvent layer. The organic solvent layer was dried over anhydrous magnesium sulfate and concentrated by evaporation at reduced pressure. The concentrate was purified using silica gel chromatography to afford the title compound (yield 21%).

$^1$H-NMR (CDCl$_3$, 300 MHz) δ 8.30 (d, 1H, J=1.4 Hz), 8.28 (d, 1H, J=2.6 Hz), 7.87 (s, 1H), 7.62 (s, 1H), 7.37 (d, 1H, J=1.2 Hz), 7.22-7.13 (m, 1H), 6.99-6.86 (m, 2H), 5.38 (s, 1H), 4.45-4.28 (m, 2H), 3.99-3.91 (m, 1H), 3.35-3.26 (m, 2H), 2.00-1.92 (m, 2H), 1.59-1.47 (m, 2H), 1.33-1.31 (dd, 3H, J=3.1 Hz, J=3.4 Hz).

Compounds of Examples 90 to 121 were synthesized in similar manners to the method of Example 89.

EXAMPLE 90

Preparation of (2R,3R)-2-(2,4-difluorophenyl)-3-((1-phenylpiperidin-4-yl)oxy)-1-(1H-1,2,4-triazol-1-yl)butan-2-ol $^1$H-NMR (CDCl$_3$, 300 MHz) δ 7.90 (s, 1H), 7.77 (s, 1H), 7.35 (m, 2H), 7.18 (m, 2H), 6.83 (m, 2H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 91

Preparation of (2R,3R)-2-(2,4-difluorophenyl)-3-((1-(2-fluorophenyl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 1H), 7.09 (m, 2H), 6.83 (m, 2H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 92

Preparation of (2R,3R)-2-(2,4-difluorophenyl)-3-((1-(3-fluorophenyl)piperidin-4-yl)oxy)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 93

Preparation of (2R,3R)-2-(2,4-difluorophenyl)-3-((1-(4-fluorophenyl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 1H), 7.10 (m, 2H), 6.83 (m, 2H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 94

Preparation of (2R,3R)-3-((1-(2-bromophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.42 (m, 1H), 7.19 (m, 2H), 6.83 (m, 2H), 6.70 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 95

Preparation of (2R,3R)-3-((1-(3-chlorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 96

Preparation of (2R,3R)-3-((1-(4-chlorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.28 (m, 3H), 6.83 (m, 2H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 97

Preparation of (2R,3R)-3-((1-(2-bromophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.52 (m, 1H), 7.19 (m, 2H), 6.93 (m, 2H), 6.70 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 98

Preparation of (2R,3R)-3-((1-(3-bromophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 1H), 6.99 (m, 3H), 6.81 (m, 2H), 6.67 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 99

Preparation of (2R,3R)-3-((1-(4-bromophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 2H), 6.83 (m, 2H), 6.72 (m, 3H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 100

Preparation of (2R,3R)-2-(2,4-difluorophenyl)-1-(1H-1,2,4-triazol-1-yl)-3-((1-(2-(trifluoromethyl)phenyl)piperidin-4-yl)oxy)butan-2-ol $^1$H-NMR (CDCl$_3$, 300 MHz) δ 7.91 (s, 1H), 7.77 (s, 1H), 7.50 (m, 1H), 7.17 (m, 2H), 6.92 (m, 2H), 6.69 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 101

Preparation of (2R,3R)-2-(2,4-difluorophenyl)-1-(1H-1,2,4-triazol-1-yl)-3-((1-(3-(trifluoromethyl)phenyl)piperidin-4-yl)oxy)butan-2-ol $^1$H-NMR (CDCl$_3$, 300 MHz) δ 7.90 (s, 1H), 7.76 (s, 1H), 7.31 (m, 4H), 6.99 (m, 2H), 6.67 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 102

Preparation of (2R,3R)-2-(2,4-difluorophenyl)-1-(1H-1,2,4-triazol-1-yl)-3-((1-(4-(trifluoromethyl)phenyl)piperidin-4-yl)oxy)butan-2-ol $^1$H-NMR (CDCl$_3$, 300 MHz) δ 7.91 (s, 1H), 7.77 (s, 1H), 7.34 (m, 2H), 6.83 (m, 2H), 6.74 (m, 3H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 103

2-(4-(((2R,3R)-3-(2,4-difluorophenyl)-3-hydroxy-4-(1H-1,2,4-triazol-1-yl)butan-2-yl)oxy)piperidin-1-yl)benzonitrile $^1$H-NMR (CDCl$_3$, 300 MHz) δ 7.91 (s, 1H), 7.77 (s, 1H), 7.50 (m, 1H), 7.37 (m, 1H), 7.27 (m, 1H), 6.92 (m, 3H), 6.62 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 104

3-(4-(((2R,3R)-3-(2,4-difluorophenyl)-3-hydroxy-4-(1H-1,2,4-triazol-1-yl)butan-2-yl)oxy)piperidin-1-yl)benzonitrile $^1$H-NMR (CDCl$_3$, 300 MHz) δ 7.90 (s, 1H), 7.76 (s, 1H), 7.26 (m, 3H), 6.99 (m, 2H), 6.67 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 105

4-(4-(((2R,3R)-3-(2,4-difluorophenyl)-3-hydroxy-4-(1H-1,2,4-triazol-1-yl)butan-2-yl)oxy)piperidin-1-yl)benzonitrile $^1$H-NMR (CDCl$_3$, 300 MHz) δ 7.91 (s, 1H), 7.77 (s, 1H), 7.47 (m, 2H), 7.32 (m, 2H), 6.83 (m, 2H), 6.74 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 106

Preparation of (2R,3R)-3-((1-(2,4-dichlorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.55 (m, 1H), 7.25 (m, 1H), 7.11 (d, 1H), 6.83 (m, 1H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 107

Preparation of (2R,3R)-3-((1-(3,4-dichlorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 2H), 7.11 (m, 1H), 6.83 (m, 1H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 108

Preparation of (2R,3R)-3-((1-(4-chloro-2-fluorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.45 (m, 1H), 7.25 (m, 1H), 7.01 (d, 1H), 6.83 (m, 1H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 109

Preparation of (2R,3R)-2-(2,4-difluorophenyl)-3-((1-(2,4-difluorophenyl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 1H), 6.94 (m, 1H), 6.83 (m, 1H), 6.72 (m, 2H), 6.55 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 110

Preparation of (2R,3R)-3-((1-(4-chloro-3-fluorophenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.37 (m, 2H), 7.11 (m, 1H), 6.65 (m, 2H), 6.49 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 111

Preparation of (2R,3R)-3-((1-(4-chloro-2-methylphenyl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.25 (m, 1H), 7.15 (m, 1H), 7.01 (d, 1H), 6.83 (m, 1H), 6.72 (m, 2H), 4.82 (m, 2H), 3.58 (m, 2H), 3.19 (m, 1H), 2.75 (m, 3H), 2.20 (s, 3H), 1.91 (m, 2H), 1.50 (m, 2H), 0.92 (d, 3H)

EXAMPLE 112

Preparation of (2R,3R)-2-(2,4-difluorophenyl)-3-((1-(pyridin-2-yl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.75 (s, 1H), 7.55 (m, 1H), 7.30 (m, 1H), 6.94 (m, 1H), 6.83 (m, 1H), 6.72 (m, 2H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 113

Preparation of (2R,3R)-2-(2,4-difluorophenyl)-3-((1-(5-methylpyridin-2-yl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.65 (s, 1H), 7.30 (m, 2H), 6.94 (m, 1H), 6.72 (m, 2H), 4.82 (m, 2H), 3.58 (m, 2H), 3.19 (m, 1H), 2.75 (m, 3H), 2.31 (s, 3H), 1.91 (m, 2H), 1.50 (m, 2H), 0.92 (d, 3H)

EXAMPLE 114

Preparation of (2R,3R)-2-(2,4-difluorophenyl)-3-((1-(5-fluoropyridin-2-yl)piperidin-4-yl)oxy)-1-(1H-1,2,4-triazol-1-yl)butan-2-ol $^1$H-NMR (CDCl$_3$, 300 MHz) δ 7.91 (s, 1H), 7.77 (s, 1H), 7.61 (s, 1H), 7.29 (m, 2H), 6.94 (m, 1H), 6.72 (m, 2H), 4.82 (m, 2H), 3.58 (m, 2H), 3.19 (m, 1H), 2.75 (m, 3H), 2.31 (s, 3H), 1.91 (m, 2H), 1.50 (m, 2H), 0.92 (d, 3H)

EXAMPLE 115

Preparation of (2R,3R)-3-((1-(5-chloropyridin-2-yl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.72 (s, 1H), 7.59 (m, 2H), 6.94 (m, 1H), 6.72 (m, 2H), 4.82 (m, 2H), 3.58 (m, 2H), 3.19 (m, 1H), 2.75 (m, 3H), 2.31 (s, 3H), 1.91 (m, 2H), 1.50 (m, 2H), 0.92 (d, 3H)

EXAMPLE 116

Preparation of (2R,3R)-2-(2,4-difluorophenyl)-3-((1-(3-methyl-5-(trifluoromethyl)pyridin-2-yl)piperidin-4-yl)oxy)-1-(1H-1,2,4-triazol-1-yl)butan-2-ol $^1$H-NMR (CDCl$_3$, 300 MHz) δ 7.91 (s, 1H), 7.87 (s, 1H), 7.72 (s, 1H), 7.59 (m, 2H), 6.94 (m, 1H), 6.72 (m, 1H), 4.82 (m, 2H), 3.58 (m, 2H), 3.19 (m, 1H), 2.75 (m, 3H), 2.31 (s, 3H), 1.91 (m, 2H), 1.50 (m, 2H), 0.92 (d, 3H)

EXAMPLE 117

Preparation of (2R,3R)-2-(2,4-difluorophenyl)-3-((1-(5-methylpyrimidin-2-yl)piperidin-4-yl)oxy)-1-(1H-1,2,4-triazol-1-yl)butan-2-ol $^1$H-NMR (CDCl$_3$, 300 MHz) δ 8.25 (s, 1H), 8.15 (s, 1H), 7.85 (s, 1H), 7.60 (m, 2H), 6.94 (m, 1H), 6.70 (m, 1H), 4.82 (m, 2H), 3.58 (m, 2H), 3.19 (m, 1H), 2.75 (m, 3H), 2.31 (s, 3H), 1.91 (m, 2H), 1.50 (m, 2H), 0.92 (d, 3H)

EXAMPLE 118

Preparation of (2R,3R)-2-(2,4-difluorophenyl)-3-((1-(5-fluoropyrimidin-2-yl)piperidin-4-yl)oxy)-1-(1H-1,2,4-triazol-1-yl)butan-2-ol $^1$H-NMR (CDCl$_3$, 300 MHz) δ 8.29 (s, 1H), 8.20 (s, 1H), 7.86 (s, 1H), 7.60 (m, 2H), 6.94 (m, 1H), 6.67 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 119

Preparation of (2R,3R)-3-((1-(5-chloropyrimidin-2-yl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 8.29 (s, 1H), 8.20 (s, 1H), 7.89 (s, 1H), 7.65 (m, 2H), 6.94 (m, 1H), 6.65 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 120

Preparation of (2R,3R)-3-((1-(5-bromopyrimidin-2-yl)piperidin-4-yl)oxy)-2-(2,4-difluorophenyl)-1-(1H-1,2,4-triazol-1-yl)butan-2-ol $^1$H-NMR (CDCl$_3$, 300 MHz) δ 8.29 (s, 1H), 8.20 (s, 1H), 7.88 (s, 1H), 7.69 (m, 2H), 6.94 (m, 1H), 6.69 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 121

Preparation of (2R,3R)-2-(2,4-difluorophenyl)-1-(1H-1,2,4-triazol-1-yl)-3-((1-(4-(trifluoromethyl)pyrimidin-2-yl)piperidin-4-yl)oxy)butan-2-ol $^1$H-NMR (CDCl$_3$, 300 MHz) δ 8.29 (s, 1H), 8.12 (s, 1H), 7.86 (s, 1H), 7.60 (m, 2H), 6.92 (m, 1H), 6.67 (m, 1H), 4.82 (m, 2H), 3.58 (m, 2H), 3.19 (m, 1H), 2.75 (m, 3H), 1.91 (m, 2H), 1.50 (m, 2H), 0.92 (d, 3H)

EXAMPLE 122

Preparation of (2R,3R)-2-(2,4-difluorophenyl)-3-((1-(2-fluorophenyl)piperidin-4-yl)amino)-1-(1H-1,2,4-triazol-1-yl)butan-2-ol To a solution of 1-(2-fluorophenyl)piperidin-4-one (36.0 mg, 0.19 mmol) in anhydrous ethanol (1 mL) was added (2R,3R)-3-amino-2-(2,4-difluorophenyl)-1-(1H-1,2,4-triazol-1-yl)butan-2-ol (50.0 mg, 0.19 mmol). While being stirred, the reaction solution was mixed at room temperature for four hrs with titanium (IV) isopropoxide (0.06 mL, 0.21 mmol) and then at room temperature for 18 hrs with sodium cyanoborohydride (35.0 mg, 0.56 mmol). The reaction was terminated by adding distilled water, after which the reaction mixture was concentrated by evaporation at reduced pressure and extracted with ethyl acetate to give an organic solvent layer. This organic layer was dried over anhydrous magnesium sulfate and purified by silica gel chromatography to afford the title compound (yield 44%).

$^1$H-NMR (CDCl$_3$, 300 MHz) δ7.93 (s, 1H), 7.76 (s, 1H), 7.39 (m, 2H), 4.92 (d, 1H, J=14.3 Hz), 4.73 (d, 1H, J=14.5 Hz), 3.42 (m, 2H), 3.21 (m, 1H), 2.73 (m, 3H), 1.94 (m, 2H), 1.59 (m, 2H), 0.93 (d, 3H, J=5.5 Hz).

Compounds of Examples 123 to 176 were synthesized in similar manners to the method of Example 122.

EXAMPLE 123

Preparation of (2R,3R)-2-(2,4-difluorophenyl)-3-((1-phenylpiperidin-4-yl)amino)-1-(1H-1,2,4-triazol-1-yl)butan-2-ol $^1$H-NMR (CDCl$_3$, 300 MHz) δ 7.90 (s, 1H), 7.77 (s, 1H), 7.35 (m, 2H), 7.18 (m, 2H), 6.83 (m, 2H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 124

Preparation of (2R,3R)-2-(2,4-difluorophenyl)-3-((1-(3-fluorophenyl)piperidin-4-yl)amino)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82

(m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 125

Preparation of (2R,3R)-2-(2,4-difluorophenyl)-3-((1-(4-fluorophenyl)piperidin-4-yl)amino)-1-(1H-1,2,4-triazol-1-yl)butan-2-ol $^1$H-NMR (CDCl$_3$, 300 MHz) δ 7.91 (s, 1H), 7.74 (s, 1H), 7.36 (m, 1H), 6.90 (m, 4H), 6.75 (t, 2H), 4.91 (d, 1H), 4.71 (d, 1H), 3.39 (m, 2H), 3.19 (m, 1H), 2.72 (m, 3H), 1.95 (m, 2H), 1.51 (m, 2H), 0.91 (d, 3H)

EXAMPLE 126

Preparation of (2R,3R)-3-((1-(2-chlorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.42 (m, 1H), 7.19 (m, 2H), 6.83 (m, 2H), 6.70 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 127

Preparation of (2R,3R)-3-((1-(3-chlorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 128

Preparation of (2R,3R)-3-((1-(4-chlorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.36 (m, 1H), 7.18 (m, 2H), 6.84 (m, 2H), 6.74 (m, 2H), 4.93 (d, 1H), 4.71 (d, 1H), 3.58 (m, 2H), 3.19 (m, 1H), 2.76 (m, 3H), 1.92 (m, 2H), 1.5 (m, 2H), 0.92 (d, 3H)

EXAMPLE 129

Preparation of (2R,3R)-3-((1-(2-bromophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.52 (m, 1H), 7.19 (m, 2H), 6.93 (m, 2H), 6.70 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 130

Preparation of (2R,3R)-3-((1-(3-bromophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 1H), 6.99 (m, 3H), 6.81 (m, 2H), 6.67 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 131

Preparation of (2R,3R)-3-((1-(4-bromophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 2H), 6.83 (m, 2H), 6.72 (m, 3H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 132

Preparation of (2R,3R)-2-(2,4-difluorophenyl)-1-(1H-1,2,4-triazol-1-yl)-3-((1-(2-(trifluoromethyl)phenyl)piperidin-4-yl)amino)butan-2-ol $^1$H-NMR (CDCl$_3$, 300 MHz) δ 7.91 (s, 1H), 7.77 (s, 1H), 7.50 (m, 1H), 7.17 (m, 2H), 6.92 (m, 2H), 6.69 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 133

Preparation of (2R,3R)-2-(2,4-difluorophenyl)-1-(1H-1,2,4-triazol-1-yl)-3-((1-(3-(trifluoromethyl)phenyl)piperidin-4-yl)amino)butan-2-ol $^1$H-NMR (CDCl$_3$, 300 MHz) δ 7.90 (s, 1H), 7.76 (s, 1H), 7.31 (m, 4H), 6.99 (m, 2H), 6.67 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 134

Preparation of (2R,3R)-2-(2,4-difluorophenyl)-1-(1H-1,2,4-triazol-1-yl)-3-((1-(4-(trifluoromethyl)phenyl)piperidin-4-yl)amino)butan-2-ol $^1$H-NMR (CDCl$_3$, 300 MHz) δ 7.91 (s, 1H), 7.77 (s, 1H), 7.34 (m, 2H), 6.83 (m, 2H), 6.74 (m, 3H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 135

2-(4-(((2R,3R)-3-(2,4-difluorophenyl)-3-hydroxy-4-(1H-1,2,4-triazol-1-yl)butan-2-yl)amino)piperidin-1-yl)benzonitrile $^1$H-NMR (CDCl$_3$, 300 MHz) δ 7.91 (s, 1H), 7.77 (s, 1H), 7.50 (m, 1H), 7.37 (m, 1H), 7.27 (m, 1H), 6.92 (m, 3H), 6.62 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 136

3-(4-(((2R,3R)-3-(2,4-difluorophenyl)-3-hydroxy-4-(1H-1,2,4-triazol-1-yl)butan-2-yl)amino)piperidin-1-yl)benzonitrile $^1$H-NMR (CDCl$_3$, 300 MHz) δ 7.90 (s, 1H), 7.76 (s, 1H), 7.26 (m, 3H), 6.99 (m, 2H), 6.67 (m, 2H), 4.82 (m, 2H), 3.58

(m, 2H), 3.19 (m, 1H), 2.99 (m, 4H), 2.15 (bs, 1H), 1.97 (m, 2H), 1.48 (m, 2H), 0.92 (d, 3H)

EXAMPLE 137

4-(4-(((2R,3R)-3-(2,4-difluorophenyl)-3-hydroxy-4-(1H-1,2,4-triazol-1-yl)butan-2-yl)amino)piperidin-1-yl)benzonitrile $^1$H-NMR (CDCl$_3$, 300 MHz) δ 7.91 (s, 1H), 7.77 (s, 1H), 7.47 (m, 2H), 7.32 (m, 2H), 6.83 (m, 2H), 6.74 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 138

Preparation of (2R,3R)-3-((1-(2,4-dichlorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.55 (m, 1H), 7.25 (m, 1H), 7.11 (d, 1H), 6.83 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 139

Preparation of (2R,3R)-3-((1-(3,4-dichlorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 2H), 7.11 (m, 1H), 6.83 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 140

Preparation of (2R,3R)-3-((1-(4-chloro-2-fluorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.45 (m, 1H), 7.25 (m, 1H), 7.01 (d, 1H), 6.83 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 141

Preparation of (2R,3R)-2-(2,4-difluorophenyl)-3-((1-(2,4-difluorophenyl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 1H), 6.94 (m, 1H), 6.83 (m, 1H), 6.72 (m, 2H), 6.55 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 142

Preparation of (2R,3R)-3-((1-(4-chloro-3-fluorophenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.37 (m, 2H), 7.11 (m, 1H), 6.65 (m, 1H), 6.49 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 143

Preparation of (2R,3R)-3-((1-(4-chloro-2-methylphenyl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.25 (m, 1H), 7.15 (m, 1H), 7.01 (d, 1H), 6.83 (m, 1H), 6.72 (m, 2H), 4.82 (m, 2H), 3.58 (m, 2H), 3.19 (m, 1H), 2.99 (m, 4H), 2.18 (s, 3H), 2.15 (bs, 1H), 1.97 (m, 2H), 1.48 (m, 2H), 0.92 (d, 3H)

EXAMPLE 144

Preparation of (2R,3R)-2-(2,4-difluorophenyl)-3-((1-(pyridin-2-yl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.75 (s, 1H), 7.55 (m, 1H), 7.30 (m, 1H), 6.94 (m, 1H), 6.83 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 145

Preparation of (2R,3R)-2-(2,4-difluorophenyl)-3-((1-(5-methylpyridin-2-yl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.65 (s, 1H), 7.30 (m, 2H), 6.94 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 146

Preparation of (2R,3R)-2-(2,4-difluorophenyl)-3-((1-(5-fluoropyridin-2-yl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.61 (s, 1H), 7.29 (m, 2H), 6.94 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 147

Preparation of (2R,3R)-3-((1-(5-chloropyridin-2-yl)piperidin-4-yl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.72 (s, 1H), 7.59 (m, 2H), 6.94 (m, 1H), 6.72 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 148

Preparation of (2R,3R)-2-(2,4-difluorophenyl)-3-((1-(3-methyl-5-(trifluoromethyl)pyridin-2-yl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.36 (m, 1H), 7.18 (m, 1H), 6.84 (m, 1H), 6.74 (m, 2H), 4.93

(d, 1H), 4.71 (d, 1H), 3.58 (m, 2H), 3.19 (m, 1H), 2.76 (m, 3H), 1.92 (m, 2H), 1.50 (m, 2H), 0.92 (d, 3H)

EXAMPLE 149

Preparation of (2R,3R)-2-(2,4-difluorophenyl)-3-((1-(pyrimidin-2-yl)piperidin-4-yl)amino)-1-(1H-1,2,4-triazol-1-yl)butan-2-ol $^1$H-NMR (CDCl$_3$, 300 MHz) δ 8.25 (s, 1H), 8.15 (s, 1H), 7.85 (s, 1H), 7.60 (m, 2H), 6.94 (m, 1H), 6.70 (m, 2H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 150

Preparation of (2R,3R)-2-(2,4-difluorophenyl)-3-((1-(5-methylpyrimidin-2-yl)piperidin-4-yl)amino)-1-(1H-1,2,4-triazol-1-yl)butan-2-ol $^1$H-NMR (CDCl$_3$, 300 MHz) δ 8.25 (s, 1H), 8.15 (s, 1H), 7.85 (s, 1H), 7.60 (m, 2H), 6.94 (m, 1H), 6.70 (m, 1H), 4.82 (m, 2H), 3.58 (m, 2H), 3.19 (m, 1H), 2.99 (m, 3H), 2.31 (s, 3H), 2.15 (bs, 1H), 1.97 (m, 2H), 1.48 (m, 2H), 0.92 (d, 3H)

EXAMPLE 151

Preparation of (2R,3R)-2-(2,4-difluorophenyl)-3-((1-(5-fluoropyrimidin-2-yl)piperidin-4-yl)-amino)-1-(1H-1,2,4-triazol-1-yl)butan-2-ol $^1$H-NMR (CDCl$_3$, 300 MHz) δ 8.19 (s, 1H), 7.89 (s, 1H), 7.76 (s, 1H), 7.37 (m, 2H), 6.75 (m, 2H), 4.93 (d, 1H), 4.72 (d, 1H), 4.53 (d, 2H), 3.22 (q, 1H), 3.06 (m, 2H), 2.86 (m, 1H), 1.89 (m, 2H), 1.37 (m, 2H), 0.92 (d, 3H)

EXAMPLE 152

Preparation of (2R,3R)-3-((1-(5-chloropyrimidin-2-yl)piperidin-4-yl)-amino)-2-(2,4-difluorophenyl)-1-(1H-1,2,4-triazol-1-yl)butan-2-ol $^1$H-NMR (CDCl$_3$, 300 MHz) δ 8.29 (s, 1H), 8.20 (s, 1H), 7.89 (s, 1H), 7.65 (m, 2H), 6.94 (m, 1H), 6.65 (m, 1H), 4.82 (m, 2H), 3.58 (m, 2H), 3.19 (m, 1H), 2.99 (m, 4H), 2.15 (bs, 1H), 1.97 (m, 2H), 1.48 (m, 2H), 0.92 (d, 3H)

EXAMPLE 153

Preparation of (2R,3R)-3-((1-(5-bromopyrimidin-2-yl)piperidin-4-yl)amino)-2-(2,4-difluorophenyl)-1-(1H-1,2,4-triazol-1-yl)butan-2-ol $^1$H-NMR (CDCl$_3$, 300 MHz) δ 8.28 (s, 2H), 7.88 (s, 1H), 7.76 (s, 1H), 7.36 (m, 1H), 6.75 (m, 2H), 4.92 (d, 1H), 4.71 (d, 1H), 4.54 (d, 1H), 3.21 (m, 1H), 3.07 (m, 2H), 2.83 (m, 1H), 1.88 (m, 2H), 1.35 (m, 2H), 0.97 (d, 3H)

EXAMPLE 154

Preparation of (2R,3R)-2-(2,4-difluorophenyl)-1-(1H-1,2,4-triazol-1-yl)-3-((1-(4-(trifluoromethyl)pyrimidin-2-yl)piperidin-4-yl)amino)butan-2-ol $^1$H-NMR (CDCl$_3$, 300 MHz) δ 8.47 (d, 1H), 7.88 (s, 1H), 7.76 (s, 1H), 7.36 (m, 1H), 6.74 (m, 3H), 4.94 (d, 1H), 4.72 (d, 1H), 3.18 (m, 3H), 2.88 (m, 1H), 1.91 (m, 2H), 1.43 (m, 2H), 0.92 (d, 3H)

EXAMPLE 155

Preparation of (2R,3R)-2-(2,4-difluorophenyl)-3-(methyl(1-phenylpiperidin-4-yl)amino)-1-(1H-1,2,4-triazol-1-yl)butan-2-ol $^1$H-NMR (CDCl$_3$, 300 MHz) δ 7.90 (s, 1H), 7.77 (s, 1H), 7.35 (m, 2H), 7.18 (m, 2H), 6.83 (m, 2H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 156

Preparation of (2R,3R)-2-(2,4-difluorophenyl)-3-((1-(2-fluorophenyl)piperidin-4-yl)(methyl)amino)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 1H), 7.09 (m, 2H), 6.83 (m, 2H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 157

Preparation of (2R,3R)-2-(2,4-difluorophenyl)-3-((1-(3-fluorophenyl)piperidin-4-yl)(methyl)amino)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 158

Preparation of (2R,3R)-2-(2,4-difluorophenyl)-3-((1-(4-fluorophenyl)piperidin-4-yl)(methyl)amino)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 1H), 7.10 (m, 2H), 6.83 (m, 2H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 159

Preparation of (2R,3R)-3-((1-(2-chlorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.42 (m, 1H), 7.19 (m, 2H), 6.83 (m, 2H), 6.70 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 160

Preparation of (2R,3R)-3-((1-(3-chlorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 2H), 6.99 (m, 1H), 6.81 (m, 2H), 6.69 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 161

Preparation of (2R,3R)-3-((1-(4-chlorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.28 (m, 3H), 6.83 (m, 2H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 162

Preparation of (2R,3R)-3-((1-(2-bromophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.52 (m, 1H), 7.19 (m, 2H), 6.93 (m, 2H), 6.70 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 163

Preparation of (2R,3R)-3-((1-(3-bromophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 1H), 6.99 (m, 3H), 6.81 (m, 2H), 6.67 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 164

Preparation of (2R,3R)-3-((1-(4-bromophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.32 (m, 2H), 6.83 (m, 2H), 6.72 (m, 3H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 165

Preparation of (2R,3R)-2-(2,4-difluorophenyl)-3-(methyl(1-(2-(trifluoromethyl)phenyl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.50 (m, 1H), 7.17 (m, 2H), 6.92 (m, 2H), 6.69 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 166

Preparation of (2R,3R)-2-(2,4-difluorophenyl)-3-(methyl(1-(3-(trifluoromethyl)phenyl)piperidin-4-yl)amino)-1-(1H-1,2,4-triazol-1-yl)butan-2-ol $^1$H-NMR (CDCl$_3$, 300 MHz) δ 7.90 (s, 1H), 7.76 (s, 1H), 7.31 (m, 4H), 6.99 (m, 2H), 6.67 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 167

Preparation of (2R,3R)-2-(2,4-difluorophenyl)-3-(methyl(1-(4-(trifluoromethyl)phenyl)piperidin-4-yl)amino)-1-(1H-1,2,4-triazol-1-yl)butan-2-ol $^1$H-NMR (CDCl$_3$, 300 MHz) δ 7.91 (s, 1H), 7.77 (s, 1H), 7.34 (m, 2H), 6.83 (m, 2H), 6.74 (m, 3H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 168

2-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile $^1$H-NMR (CDCl$_3$, 300 MHz) δ 7.91 (s, 1H), 7.77 (s, 1H), 7.50 (m, 1H), 7.37 (m, 1H), 7.27 (m, 1H), 6.92 (m, 3H), 6.62 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 169

3-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile $^1$H-NMR (CDCl$_3$, 300 MHz) δ 7.90 (s, 1H), 7.76 (s, 1H), 7.26 (m, 3H), 6.99 (m, 2H), 6.67 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 170

4-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile $^1$H-NMR (CDCl$_3$, 300 MHz) δ 7.91 (s, 1H), 7.77 (s, 1H), 7.47 (m, 2H), 7.32 (m, 2H), 6.83 (m, 2H), 6.74 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 171

Preparation of (2R,3R)-3-((1-(2,4-dichlorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.55 (m, 1H), 7.25 (m, 1H), 7.11 (d, 1H), 6.83 (m, 1H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 172

Preparation of (2R,3R)-3-((1-(3,4-dichlorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 2H), 7.11 (m, 1H), 6.83 (m, 1H), 6.72 (m, 2H), 4.82

(m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 173

Preparation of (2R,3R)-3-((1-(4-chloro-2-fluorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.45 (m, 1H), 7.25 (m, 1H), 7.01 (d, 1H), 6.83 (m, 1H), 6.72 (m, 2H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 174

Preparation of (2R,3R)-2-(2,4-difluorophenyl)-3-((1-(2,4-difluorophenyl)piperidin-4-yl)(methyl)amino)-1-(1H-1,2,4-triazol-1-yl)butan-2-ol $^1$H-NMR (CDCl$_3$, 300 MHz) δ 7.91 (s, 1H), 7.77 (s, 1H), 7.35 (m, 1H), 6.94 (m, 1H), 6.83 (m, 1H), 6.72 (m, 2H), 6.55 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 175

Preparation of (2R,3R)-3-((1-(4-chloro-3-fluorophenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.37 (m, 2H), 7.11 (m, 1H), 6.65 (m, 2H), 6.49 (m, 1H), 4.82 (m, 2H), 3.58 (m, 2H), 3.19 (m, 1H), 2.99 (m, 4H), 2.26 (s, 3H), 2.15 (bs, 1H), 1.97 (m, 2H), 1.48 (m, 2H), 0.92 (d, 3H)

EXAMPLE 176

Preparation of (2R,3R)-3-((1-(4-chloro-2-methylphenyl)piperidin-4-yl)(methyl)amino)-2-(2,4-difluorophenyl)-1-(1H-1,2,4-triazol-1-yl)butan-2-ol $^1$H-NMR (CDCl$_3$, 300 MHz) δ 7.91 (s, 1H), 7.77 (s, 1H), 7.25 (m, 1H), 7.15 (m, 1H), 7.01 (d, 1H), 6.83 (m, 1H), 6.72 (m, 2H), 4.82 (m, 2H), 3.58 (m, 2H), 3.19 (m, 1H), 2.99 (m, 4H), 2.26 (s, 3H), 2.18 (s, 3H), 2.15 (bs, 1H), 1.97 (m, 2H), 1.48 (m, 2H), 0.92 (d, 3H)

EXAMPLE 177

Preparation of (2R,3R)-2-(2,4-difluorophenyl)-3-((1-phenylpiperidin-3-yl)amino)-1-(1H-1,2,4-triazol-1-yl)butan-2-ol The same procedure as in Example 122 was repeated, with the exception of using 1-phenylpiperidin-3-on, to afford the title compound (yield 18%).

$^1$H-NMR (CDCl$_3$, 300 MHz) δ 7.90 (s, 1H), 7.77 (s, 1H), 7.35 (m, 2H), 7.18 (m, 2H), 6.83 (m, 2H), 6.72 (m, 2H), 4.82 (m, 2H), 3.58 (m, 2H), 3.19 (m, 2H), 2.97 (m, 3H), 2.15 (bs, 1H), 0.97 (m, 2H), 1.48 (m, 2H), 0.92 (d, 3H).

EXAMPLE 178

Preparation of (2R,3R)-2-(2,4-difluorophenyl)-3-(3-(phenylamino)pyrrolidin-1-yl)-1-(1H-1,2,4-triazol-1-yl)butan-2-ol The same procedure as in Example 1 was repeated, with the exception of using N-phenylpyrrolidin-3-amine, to afford the title compound.

$^1$H-NMR (CDCl$_3$, 300 MHz) δ 8.47 (d, 1H), 7.88 (s, 1H), 7.76 (s, 1H), 7.36 (m, 1H), 6.74 (m, 3H), 4.94 (d, 1H, J=14.3 Hz), 4.72 (d, 1H, J=14.6 Hz), 3.18 (m, 3H), 2.88 (m, 1H), 1.91 (m, 2H), 1.43 (m, 2H), 0.92 (d, 3H)

EXAMPLE 179

Preparation of (2R,3R)-3-((R)-3-(4-chlorophenoxy)pyrrolidin-1-yl)-2-(2,4-difluorophenyl)-1-(1H-1,2,4-triazol-1-yl)butan-2-ol The same procedure as in Example 1 was repeated, with the exception of using (R)-3-(4-chlorophenoxy)pyrrolidine, to afford the title compound (yield 28%).

$^1$H-NMR (CDCl$_3$, 300 MHz) δ 8.21 (d, 2H), 8.01 (s, 1H), 7.82 (s, 1H), 7.48 (m, 1H), 7.02 (m, 2H), 6.93 (d, 2H), 4.93 (m, 2H), 4.74 (d, 1H), 3.57 (m, 4H), 2.16 (m, 2H), 0.92 (d, 3H)

EXAMPLE 180

Preparation of (2R,3R)-3-((S)-3-(4-chlorophenoxy)pyrrolidin-1-yl)-2-(2,4-difluorophenyl)-1-(1H-1,2,4-triazol-1-yl)butan-2-ol The same procedure as in Example 1 was repeated, with the exception of using (S)-3-(4-chlorophenoxy)pyrrolidine, to afford the title compound.

$^1$H-NMR (CDCl$_3$, 300 MHz) δ 8.21 (d, 2H), 8.01 (s, 1H), 7.82 (s, 1H), 7.48 (m, 1H), 7.02 (m, 2H), 6.93 (d, 2H), 4.93 (m, 2H), 4.74 (d, 1H), 3.57 (m, 4H), 2.16 (m, 2H), 0.92 (d, 3H)

FORMULATION EXAMPLE 1

Tablets (2R,3R)-2-(2,4-difluorophenyl)-3-(4-(4-fluorophenoxy)piperidin-1-yl)-1-(1H-1,2,4-triazol-1-yl)butan-2-ol (50 mg), prepared in Example 1, was granulated, in combination with magnesium stearate (20 mg), using water-soluble starch (35 mg) and dried. The granules were mixed for 30 min with lactose (65 mg) and corn starch (30 mg) using a mechanical shaker and a mixer. The resulting mixture was pressurized into tablets.

TEST EXAMPLE 1

Test for in vitro Antifungal Activity

The compounds of the present invention were evaluated for inhibitory activity against yeast molds including *Candida albicans*, *Candida glabrata*, *Candida krusei*, *Candida tropicalis*, *Candida parapsilosis*, and *Cryptococcus neoformans*, and filamentous fungi including *Aspergillus fumigatus*, *Trichophyton mentagrophytes* (obtained from KCTC (Korean Collection for Type Cultures), and *Trichophyton rubrum* (obtained from KCCM (Korean Culture Center of Microorganisms). All the strains, but *Trichophyton mentagrophytes* and *Trichophyton rubrum*, were purchased from the ATCC (American Type Culture Collection).

Of the strains used in this test, *Candida albicans, Candida glabrata, Candida krusei, Candida tropicalis, Candida parapsilosis, Trichophyton mentagrophytes* and *Trichophyton rubrum* were inoculated into sabouraud dextrose agars (Difco, BD-0109), *Cryptococcus neoformans* into a yeast mold agar (YM agar, Difco, 271210), and *Aspergillus fumigatus* into a malt extract agar (Difco, 211220), before incubation at 35° C. for two to ten days.

From the agars on which the yeast molds were grown, single colonies were picked up, and each was sufficiently suspended in 5 mL of already prepared, 0.85% sterile saline. After correction of the absorbance to 0.108 at 530 nm, each of the suspensions was diluted to a ratio of 1:50 in an RPMI (Roswell park memorial institute) 1640 medium and then to a ratio of 1:20 to prepare an inoculum having a cell density of from $1.0 \times 10^3$ to $5.0 \times 10^3$ CFU/mL. The cell density was adjusted into $0.4 \times 10^2 \sim 5.0 \times 10^4$ CFU/mL for *Aspergillus fumigates* and $0.4 \times 10^4 \sim 5.0 \times 10^4$ CFU/mL for both *Trichophyton mentagrophytes* and *Trichophyton rubrum*.

The antifungal agent samples were prepared by diluting the active compounds in an RPMI 1640 medium to a serial density of from 0.0156 to 32 μg/mL. In this context, dimethylsulfoxide (DMSO) was used as an excipient at a final concentration of 1% (v/v). The serial dilutions were aliquoted at a volume of 0.1 mL and applied to 0.1 mL of the aliquots of each inoculum, followed by incubation.

With the naked eyes, an observation was made of all of the yeast molds, but *Cryptococcus neoformans* 24 hrs after the application, *Cryptococcus neoformans* and *Aspergillus fumigatus* 48 hrs after the application, and *Trichophyton mentagrophytes* and *Trichophyton* rubrum five days after the application to examine whether the fungi grew or not. In addition, Alamarblue™ as used to determine the concentrations of the compounds of the present invention at which the growth of the microorganisms was 80% inhibited compared to that of the negative control. All experiments were performed in duplicate for each of the test concentration groups. Test results of the antifungal activity are summarized in Tables 1 and 2, below.

TABLE 2

Antifungal Activity ($MIC_{80}$ μg/mL)

| Example No. | Candida albicans |
|---|---|
| 3 | ≤0.015 |
| 16 | ≤0.015 |
| 25 | ≤0.015 |
| 26 | ≤0.015 |
| 30 | ≤0.015 |
| 35 | ≤0.015 |
| 38 | ≤0.015 |
| 46 | ≤0.015 |
| 49 | ≤0.015 |
| 60 | ≤0.015 |
| 62 | ≤0.015 |
| 64 | ≤0.015 |
| 67 | ≤0.015 |
| 70 | ≤0.015 |
| 73 | ≤0.015 |
| 79 | ≤0.015 |
| 82 | ≤0.015 |
| 89 | ≤0.015 |
| 90 | ≤0.015 |
| 93 | ≤0.015 |
| 96 | ≤0.015 |
| 102 | ≤0.015 |
| 105 | ≤0.015 |
| 114 | ≤0.015 |
| 115 | ≤0.015 |
| 116 | ≤0.015 |
| 118 | ≤0.015 |
| 120 | ≤0.015 |
| 123 | ≤0.015 |
| 134 | ≤0.015 |
| 137 | ≤0.015 |
| 146 | ≤0.015 |
| 147 | ≤0.015 |
| 149 | ≤0.015 |
| 155 | ≤0.015 |
| 158 | ≤0.015 |
| 161 | ≤0.015 |
| 167 | ≤0.015 |
| 170 | ≤0.015 |

As is apparent from data of Tables 1 and 2, the compounds according to the present invention exhibited excellent inhibitory effects on a wide spectrum of fungi, compared to voriconazole and fluconazole.

TABLE 1

Antifungal Activity ($MIC_{80}$ μg/mL)

| Example No. | C. albicans | C. grabrata | C. krusei | C. tropicalis | C. parapsilosis | Cryptococcus neoformans | Aspergillus fumigatus | Trichophyton mentagrophytes | Trichophyton rubrum |
|---|---|---|---|---|---|---|---|---|---|
| 1 | ≤0.015 | 0.25 | 0.062 | 0.062 | ≤0.015 | ≤0.015 | ≤0.125 | ≤0.125 | ≤0.125 |
| 7 | ≤0.015 | — | — | — | — | — | ≤0.125 | — | — |
| 13 | ≤0.015 | — | — | — | — | — | 1 | — | — |
| 29 | ≤0.015 | 1 | 0.5 | 0.25 | 0.062 | ≤0.015 | 1 | 0.062 | ≤0.125 |
| 32 | ≤0.015 | 0.125 | 0.125 | ≤0.015 | ≤0.015 | ≤0.015 | ≤0.125 | ≤0.125 | 0.031 |
| 34 | ≤0.015 | 0.125 | 0.031 | ≤0.015 | ≤0.015 | ≤0.015 | ≤0.125 | ≤0.125 | ≤0.125 |
| 58 | ≤0.015 | 1 | 0.062 | 0.125 | 0.062 | — | 0.125 | ≤0.125 | ≤0.125 |
| 59 | ≤0.015 | 0.25 | 0.062 | 0.125 | ≤0.015 | ≤0.015 | 0.25 | ≤0.125 | ≤0.125 |
| 63 | ≤0.015 | 1 | ≤0.062 | — | — | — | 0.25 | ≤0.004 | 0.015 |
| 125 | ≤0.015 | 0.125 | 0.062 | 0.031 | ≤0.015 | ≤0.015 | 0.25 | ≤0.125 | ≤0.125 |
| 128 | ≤0.015 | 0.062 | ≤0.015 | 0.031 | 0.031 | ≤0.015 | 0.25 | 0.015 | ≤0.125 |
| 148 | ≤0.015 | 0.25 | ≤0.062 | — | — | — | 1 | — | — |
| 151 | ≤0.015 | 1 | 0.25 | 0.25 | 0.125 | — | 1 | ≤0.004 | 0.015 |
| 153 | ≤0.015 | 0.125 | 0.125 | 0.25 | ≤0.015 | ≤0.015 | 1 | 0.5 | ≤0.125 |
| Voriconazole | 0.031 | 2 | 0.5 | 0.25 | 0.5 | 0.25 | 0.25 | 0.125 | ≤0.125 |
| Fluconazole | 4 | >32 | 4 | >32 | >32 | 0.5 | >128 | 16 | 4 |

—: No tests performed

TEST EXAMPLE 2

Subacute Toxicity Test in Mice

Each of the compounds of Examples 32, 34, 63, 122 and 125 according to the present invention was suspended at a concentration of 10 mL/kg in an aqueous, 0.5% methyl cellulose base and used for a subacute test in which ICR mice (male, four weeks old, weighing about 30 g) were forced to be intragastrically administered with the suspension at a compound concentration of 10 mg/kg to 50 mg/kg once every day for two weeks using a 1 mL syringe equipped with a sonde.

No toxicity symptoms were observed in terms of survival for two weeks and changes in internal organs, liver enzymes and liver weight until the minimal oral dose of 10 mg/kg.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A compound, represented by the following Chemical Formula 1, or a pharmaceutically acceptable salt thereof:

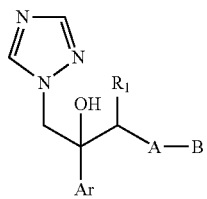

[Chemical Formula 1]

wherein,
Ar is phenyl which is substituted with one to five halogens;

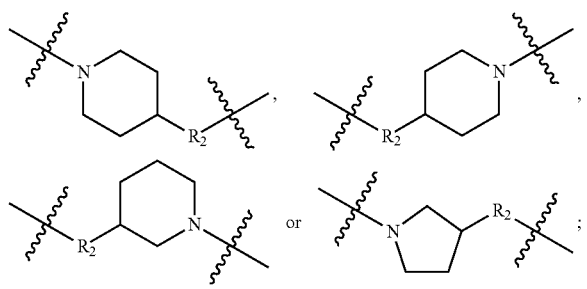

B is phenyl, pyridinyl or pyrimidinyl, which is unsubstituted or substituted with one or two $R_3$ groups;
$R_1$ is hydrogen or $C_{1-4}$ alkyl;
$R_2$ is O, NH or $NCH_3$; and
$R_3$ is independently halogen, $C_{1-4}$ alkyl, $C_{1-4}$ haloalkyl, or cyano.

2. The compound according to claim 1, wherein
B is pyridinyl which is unsubstituted or substituted with one or two $R_3$ groups, and
$R_3$ is independently halogen, $C_{1-4}$ alkyl, or $C_{1-4}$ haloalkyl.

3. The compound according to claim 1, wherein
B is pyrimidinyl which is unsubstituted or substituted with one $R_3$ group, and
$R_3$ is halogen, $C_{1-4}$ alkyl, or $C_{1-4}$ haloalkyl.

4. The compound according to claim 1, wherein
B is phenyl which is unsubstituted or substituted with one or two $R_3$ groups, and $R_2$ is $NCH_3$.

5. The compound according to claim 1, wherein
B is phenyl, pyridinyl or pyrimidinyl, which is substituted with two $R_3$ groups, and
one of the two $R_3$ groups is halogen, and the other is halogen, $C_{1-4}$ alkyl, or $C_{1-4}$ haloalkyl; or
one of the two $R_3$ groups is $C_{1-4}$ alkyl, and the other is $C_{1-4}$ haloalkyl.

6. The compound according to claim 1, wherein
$R_3$ is F, Cl, Br, methyl, trifluoromethyl, or cyano.

7. The compound according to claim 1, selected from the group consisting of:
1) (2R,3R)-2-(2,4-difluorophenyl)-3-(4-(4-fluorophenoxy)piperidin-1-yl)-1-(1H-1,2,4-triazol-1-yl)butan-2-ol,
2) (2R,3R)-2-(2,4-difluorophenyl)-3-(4-phenoxypiperidin-1-yl)-1-(1H-1,2,4-triazol-1-yl)butan-2-ol,
3) (2R,3R)-2-(2,4-difluorophenyl)-3-(4-(2-fluorophenoxy)piperidin-1-yl)-1-(1H-1,2,4-triazol-1-yl)butan-2-ol,
4) (2R,3R)-2-(2,4-difluorophenyl)-3-(4-(3-fluorophenoxy)piperidin-1-yl)-1-(1H-1,2,4-triazol-1-yl)butan-2-ol,
5) (2R,3R)-3-(4-(2-chlorophenoxy)piperidin-1-yl)-2-(2,4-difluorophenyl)-1-(1H-1,2,4-triazol-1-yl)butan-2-ol,
6) (2R,3R)-3-(4-(3-chlorophenoxy)piperidin-1-yl)-2-(2,4-difluorophenyl)-1-(1H-1,2,4-triazol-1-yl)butan-2-ol,
7) (2R,3R)-3-(4-(4-chlorophenoxy)piperidin-1-yl)-2-(2,4-difluorophenyl)-1-(1H-1,2,4-triazol-1-yl)butan-2-ol,
8) (2R,3R)-3-(4-(2-bromophenoxy)piperidin-1-yl)-2-(2,4-difluorophenyl)-1-(1H-1,2,4-triazol-1-yl)butan-2-ol,
19) (2R,3R)-3-(4-(3-bromophenoxy)piperidin-1-yl)-2-(2,4-difluorophenyl)-1-(1H-1,2,4-triazol-1-yl)butan-2-ol,
10) (2R,3R)-3-(4-(4-bromophenoxy)piperidin-1-yl)-2-(2,4-difluorophenyl)-1-(1H-1,2,4-triazol-1-yl)butan-2-ol,
11) (2R,3R)-2-(2,4-difluorophenyl)-1-(1H-1,2,4-triazol-1-yl)-3-(4-(2-(trifluoromethyl)phenoxy)piperidin-1-yl)butan-2-ol,
12) (2R,3R)-2-(2,4-difluorophenyl)-1-(1H-1,2,4-triazol-1-yl)-3-(4-(3-(trifluoromethyl)phenoxy)piperidin-1-yl)butan-2-ol,
13) (2R,3R)-2-(2,4-difluorophenyl)-1-(1H-1,2,4-triazol-1-yl)-3-(4-(4-(trifluoromethyl)phenoxy)piperidin-1-yl)butan-2-ol,
14) 2-((1-(((2R,3R)-3-(2,4-difluorophenyl)-3-hydroxy-4-(1H-1,2,4-triazol-1-yl)butan-2-yl)piperidin-4-yl)oxy)benzonitrile,
15) 3-((1-(((2R,3R)-3-(2,4-difluorophenyl)-3-hydroxy-4-(1H-1,2,4-triazol-1-yl)butan-2-yl)piperidin-4-yl)oxy)benzonitrile,
16) 4-((1-(((2R,3R)-3-(2,4-difluorophenyl)-3-hydroxy-4-(1H-1,2,4-triazol-1-yl)butan-2-yl)piperidin-4-yl)oxy)benzonitrile,
17) (2R,3R)-3-(4-(2,4-dichlorophenoxy)piperidin-1-yl)-2-(2,4-difluorophenyl)-1-(1H-1,2,4-triazol-1-yl)butan-2-ol, 18) (2R,3R)-3-(4-(3,4-dichlorophenoxy)piperidin-1-yl)-2-(2,4-difluorophenyl)-1-(1H-1,2,4-triazol-1-yl)butan-2-ol,
19) (2R,3R)-3-(4-(4-chloro-2-fluorophenoxy)piperidin-1-yl)-2-(2,4-difluorophenyl)-1-(1H-1,2,4-triazol-1-yl)butan-2-ol,
20) (2R,3R)-3-(4-(2,4-difluorophenoxy)piperidin-1-yl)-2-(2,4-difluorophenyl)-1-(1H-1,2,4-triazol-1-yl)butan-2-ol,
21) (2R,3R)-3-(4-(4-chloro-3-fluorophenoxy)piperidin-1-yl)-2-(2,4-difluorophenyl)-1-(1H-1,2,4-triazol-1-yl)butan-2-ol,
22) (2R,3R)-3-(4-(4-chloro-2-methylphenoxy)piperidin-1-yl)-2-(2,4-difluorophenyl)-1-(1H-1,2,4-triazol-1-yl)butan-2-ol,
23) (2R,3R)-2-(2,4-difluorophenyl)-3-(4-(pyridin-2-yloxy)piperidin-1-yl)-1-(1H-1,2,4-triazol-1-yl)butan-2-ol,
24) (2R,3R)-2-(2,4-difluorophenyl)-3-(4-((5-methylpyridin-2-yl)oxy)piperidin-1-yl)-1-(1H-1,2,4-triazol-1-yl)butan-2-ol,
25) (2R,3R)-2-(2,4-difluorophenyl)-3-(4-((5-fluoropyridin-2-yl)oxy)piperidin-1-yl)-1-(1H-1,2,4-triazol-1-yl)butan-2-ol,
26) (2R,3R)-3-(4-((5-chloropyridin-2-yl)oxy)piperidin-1-yl)-2-(2,4-difluorophenyl)-1-(1H-1,2,4-triazol-1-yl)butan-2-ol,
27) (2R,3R)-2-(2,4-difluorophenyl)-1-(1H-1,2,4-triazol-1-yl)-3-(4-((5-(trifluoromethyl)pyridin-2-yl)oxy)piperidin-1-yl)butan-2-ol,
28) (2R,3R)-3-(4-((3-chloro-5-(trifluoromethyl)pyridin-2-yl)oxy)piperidin-1-yl)-2-(2,4-difluorophenyl)-1-(1H-1,2,4-triazol-1-yl)butan-2-ol,
29) (2R,3R)-2-(2,4-difluorophenyl)-3-(4-(pyrimidin-2-yloxy)piperidin-1-yl)-1-(1H-1,2,4-triazol-1-yl)butan-2-ol,
30) (2R,3R)-2-(2,4-difluorophenyl)-3-(4-((5-fluoropyrimidin-2-yl)oxy)piperidin-1-yl)-1-(1H-1,2,4-triazol-1-yl)butan-2-ol,
31) (2R,3R)-3-(4-((5-chloropyrimidin-2-yl)oxy)piperidin-1-yl)-2-(2,4-difluorophenyl)-1-(1H-1,2,4-triazol-1-yl)butan-2-ol,
32) (2R,3R)-3-(4-((5-bromopyrimidin-2-yl)oxy)piperidin-1-yl)-2-(2,4-difluorophenyl)-1-(1H-1,2,4-triazol-1-yl)butan-2-ol,
33) (2R,3R)-2-(2,4-difluorophenyl)-3-(4-((5-methylpyrimidin-2-yl)oxy)piperidin-1-yl)-1-(1H-1,2,4-triazol-1-yl)butan-2-ol,
34) (2R,3R)-3-(4-((4-chlorophenyl)amino)piperidin-1-yl)-2-(2,4-difluorophenyl)-1-(1H-1,2,4-triazol-1-yl)butan-2-ol,
35) (2R,3R)-2-(2,4-difluorophenyl)-3-(4-(phenylamino)piperidin-1-yl)-1-(1H-1,2,4-triazol-1-yl)butan-2-ol,
36) (2R,3R)-2-(2,4-difluorophenyl)-3-(4-((2-fluorophenyl)amino)piperidin-1-yl)-1-(1H-1,2,4-triazol-1-yl)butan-2-ol,
37) (2R,3R)-2-(2,4-difluorophenyl)-3-(4-((3-fluorophenyl)amino)piperidin-1-yl)-1-(1H-1,2,4-triazol-1-yl)butan-2-ol,
38) (2R,3R)-2-(2,4-difluorophenyl)-3-(4-((4-fluorophenyl)amino)piperidin-1-yl)-1-(1H-1,2,4-triazol-1-yl)butan-2-ol,
39) (2R,3R)-3-(4-((2-chlorophenyl)amino)piperidin-1-yl)-2-(2,4-difluorophenyl)-1-(1H-1,2,4-triazol-1-yl)butan-2-ol,
40) (2R,3R)-3-(4-((3-chlorophenyl)amino)piperidin-1-yl)-2-(2,4-difluorophenyl)-1-(1H-1,2,4-triazol-1-yl)butan-2-ol,
41) (2R,3R)-3-(4-((2-bromophenyl)amino)piperidin-1-yl)-2-(2,4-difluorophenyl)-1-(1H-1,2,4-triazol-1-yl)butan-2-ol,
42) (2R,3R)-3-(4-((3-bromophenyl)amino)piperidin-1-yl)-2-(2,4-difluorophenyl)-1-(1H-1,2,4-triazol-1-yl)butan-2-ol,
43) (2R,3R)-3-(4-((4-bromophenyl)amino)piperidin-1-yl)-2-(2,4-difluorophenyl)-1-(1H-1,2,4-triazol-1-yl)butan-2-ol,
44) (2R,3R)-2-(2,4-difluorophenyl)-1-(1H-1,2,4-triazol-1-yl)-3-(4-((2-(trifluoromethyl)phenyl)amino)piperidin-1-yl)butan-2-ol,
45) (2R,3R)-2-(2,4-difluorophenyl)-1-(1H-1,2,4-triazol-1-yl)-3-(4-((3-(trifluoromethyl)phenyl)amino)piperidin-1-yl)butan-2-ol,
46) (2R,3R)-2-(2,4-difluorophenyl)-1-(1H-1,2,4-triazol-1-yl)-3-(4-((4-(trifluoromethyl)phenyl)amino)piperidin-1-yl)butan-2-ol,
47) 2-((1-((2R,3R)-3-(2,4-difluorophenyl)-3-hydroxy-4-(1H-1,2,4-triazol-1-yl)butan-2-yl)piperidin-4-yl)amino)benzonitrile,
48) 3-((1-((2R,3R)-3-(2,4-difluorophenyl)-3-hydroxy-4-(1H-1,2,4-triazol-1-yl)butan-2-yl)piperidin-4-yl)amino)benzonitrile,
49) 4-((1-((2R,3R)-3-(2,4-difluorophenyl)-3-hydroxy-4-(1H-1,2,4-triazol-1-yl)butan-2-yl)piperidin-4-yl)amino)benzonitrile,
50) (2R,3R)-3-(4-((2,4-dichlorophenyl)amino)piperidin-1-yl)-2-(2,4-difluorophenyl)-1-(1H-1,2,4-triazol-1-yl)butan-2-ol,
51) (2R,3R)-3-(4-((3,4-dichlorophenyl)amino)piperidin-1-yl)-2-(2,4-difluorophenyl)-1-(1H-1,2,4-triazol-1-yl)butan-2-ol,
52) (2R,3R)-3-(4-((4-chloro-2-fluorophenyl)amino)piperidin-1-yl)-2-(2,4-difluorophenyl)-1-(1H-1,2,4-triazol-1-yl)butan-2-ol,
53) (2R,3R)-2-(2,4-difluorophenyl)-3-(4-((2,4-difluorophenyl)amino)piperidin-1-yl)-1-(1H-1,2,4-triazol-1-yl)butan-2-ol,
54) (2R,3R)-3-(4-((4-chloro-3-fluorophenyl)amino)piperidin-1-yl)-2-(2,4-difluorophenyl)-1-(1H-1,2,4-triazol-1-yl)butan-2-ol,
55) (2R,3R)-3-(4-((4-chloro-2-methylphenyl)amino)piperidin-1-yl)-2-(2,4-difluorophenyl)-1-(1H-1,2,4-triazol-1-yl)butan-2-ol,
56) (2R,3R)-2-(2,4-difluorophenyl)-3-(4-(pyridin-2-ylamino)piperidin-1-yl)-1-(1H-1,2,4-triazol-1-yl)butan-2-ol,
57) (2R,3R)-2-(2,4-difluorophenyl)-3-(4-((5-methylpyridin-2-yl)amino)piperidin-1-yl)-1-(1H-1,2,4-triazol-1-yl)butan-2-ol,
58) (2R,3R)-2-(2,4-difluorophenyl)-3-(4-((5-fluoropyridin-2-yl)amino)piperidin-1-yl)-1-(1H-1,2,4-triazol-1-yl)butan-2-ol,
59) (2R,3R)-3-(4-((5-chloropyridin-2-yl)amino)piperidin-1-yl)-2-(2,4-difluorophenyl)-1-(1H-1,2,4-triazol-1-yl)butan-2-ol,
60) (2R,3R)-3-(4-((3-chloro-5-(trifluoromethyl)pyridin-2-yl)amino)piperidin-1-yl)-2-(2,4-difluorophenyl)-1-(1H-1,2,4-triazol-1-yl)butan-2-ol,
61) (2R,3R)-2-(2,4-difluorophenyl)-1-(1H-1,2,4-triazol-1-yl)-3-(4-((5-(trifluoromethyl)pyridin-2-yl)amino)piperidin-1-yl)butan-2-ol, 62) (2R,3R)-2-(2,4-difluorophenyl)-3-(4-(pyrimidin-2-ylamino)piperidin-1-yl)-1-(1H-1,2,4-triazol-1-yl)butan-2-ol,
63) (2R,3R)-2-(2,4-difluorophenyl)-3-(4-((5-fluoropyrimidin-2-yl)amino)piperidin-1-yl)-1-(1H-1,2,4-triazol-1-yl)butan-2-ol,
64) (2R,3R)-3-(4-((5-bromopyrimidin-2-yl)amino)piperidin-1-yl)-2-(2,4-difluorophenyl)-1-(1H-1,2,4-triazol-1-yl)butan-2-ol,
65) (2R,3R)-3-(4-((5-chloropyrimidin-2-yl)amino)piperidin-1-yl)-2-(2,4-difluorophenyl)-1-(1H-1,2,4-triazol-1-yl)butan-2-ol,
66) (2R,3R)-2-(2,4-difluorophenyl)-3-(4-((5-methylpyrimidin-2-yl)amino)piperidin-1-yl)-1-(1H-1,2,4-triazol-1-yl)butan-2-ol,
67) (2R,3R)-2-(2,4-difluorophenyl)-3-(4-(methyl(phenyl)amino)piperidin-1-yl)-1-(1H-1,2,4-triazol-1-yl)butan-2-ol,
68) (2R,3R)-2-(2,4-difluorophenyl)-3-(4-((2-fluorophenyl)(methyl)amino)piperidin-1-yl)-1-(1H-1,2,4-triazol-1-yl)butan-2-ol,
69) (2R,3R)-2-(2,4-difluorophenyl)-3-(4-((3-fluorophenyl)(methyl)amino)piperidin-1-yl)-1-(1H-1,2,4-triazol-1-yl)butan-2-ol,
70) (2R,3R)-2-(2,4-difluorophenyl)-3-(4-((4-fluorophenyl)(methyl)amino)piperidin-1-yl)-1-(1H-1,2,4-triazol-1-yl)butan-2-ol,
71) (2R,3R)-3-(4-((2-chlorophenyl)(methyl)amino)piperidin-1-yl)-2-(2,4-difluorophenyl)-1-(1H-1,2,4-triazol-1-yl)butan-2-ol,
72) (2R,3R)-3-(4-((3-chlorophenyl)(methyl)amino)piperidin-1-yl)-2-(2,4-difluorophenyl)-1-(1H-1,2,4-triazol-1-yl)butan-2-ol,
73) (2R,3R)-3-(4-((4-chlorophenyl)(methyl)amino)piperidin-1-yl)-2-(2,4-difluorophenyl)-1-(1H-1,2,4-triazol-1-yl)butan-2-ol,
74) (2R,3R)-3-(4-((2-bromophenyl)(methyl)amino)piperidin-1-yl)-2-(2,4-difluorophenyl)-1-(1H-1,2,4-triazol-1-yl)butan-2-ol,
75) (2R,3R)-3-(4-((3-bromophenyl)(methyl)amino)piperidin-1-yl)-2-(2,4-difluorophenyl)-1-(1H-1,2,4-triazol-1-yl)butan-2-ol,
76) (2R,3R)-3-(4-((4-bromophenyl)(methyl)amino)piperidin-1-yl)-2-(2,4-difluorophenyl)-1-(1H-1,2,4-triazol-1-yl)butan-2-ol,
77) (2R,3R)-2-(2,4-difluorophenyl)-3-(4-(methyl(2-(trifluoromethyl)phenyl)amino)piperidin-1-yl)-1-(1H-1,2,4-triazol-1-yl)butan-2-ol,
78) (2R,3R)-2-(2,4-difluorophenyl)-3-(4-(methyl(3-(trifluoromethyl)phenyl)amino)piperidin-1-yl)-1-(1H-1,2,4-triazol-1-yl)butan-2-ol,
79) (2R,3R)-2-(2,4-difluorophenyl)-3-(4-(methyl(4-(trifluoromethyl)phenyl)amino)piperidin-1-yl)-1-(1H-1,2,4-triazol-1-yl)butan-2-ol,
80) 2-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
81) 3-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
82) 4-((1-((2R,3R)-3-(2,4-difluorophenyl)-3-hydroxy-4-(1H-1,2,4-triazol-1-yl)butan-2-yl)piperidin-4-yl)(methyl)amino)benzonitrile,
83) (2R,3R)-3-(4-((2,4-dichlorophenyl)(methyl)amino)piperidin-1-yl)-2-(2,4-difluorophenyl)-1-(1H-1,2,4-triazol-1-yl)butan-2-ol,
84) (2R,3R)-3-(4-((3,4-dichlorophenyl)(methyl)amino)piperidin-1-yl)-2-(2,4-difluorophenyl)-1-(1H-1,2,4-triazol-1-yl)butan-2-ol,
85) (2R,3R)-3-(4-((4-chloro-2-fluorophenyl)(methyl)amino)piperidin-1-yl)-2-(2,4-difluorophenyl)-1-(1H-1,2,4-triazol-1-yl)butan-2-ol,
86) (2R,3R)-2-(2,4-difluorophenyl)-3-(4-((2,4-difluorophenyl)(methyl)amino)piperidin-1-yl)-1-(1H-1,2,4-triazol-1-yl)butan-2-ol,
87) (2R,3R)-3-(4-((4-chloro-3-fluorophenyl)(methyl)amino)piperidin-1-yl)-2-(2,4-difluorophenyl)-1-(1H-1,2,4-triazol-1-yl)butan-2-ol,
88) (2R,3R)-3-(4-((4-chloro-2-methylphenyl)(methyl)amino)piperidin-1-yl)-2-(2,4-difluorophenyl)-1-(1H-1,2,4-triazol-1-yl)butan-2-ol,
89) (2R,3R)-2-(2,4-difluorophenyl)-3-((1-(pyrimidin-2-yl)piperidin-4-yl)oxy)-1-(1H-1,2,4-triazol-1-yl)butan-2-ol,
90) (2R,3R)-2-(2,4-difluorophenyl)-3-((1-phenylpiperidin-4-yl)oxy)-1-(1H-1,2,4-triazol-1-yl)butan-2-ol,
91) (2R,3R)-2-(2,4-difluorophenyl)-3-((1-(2-fluorophenyl)piperidin-4-yl)oxy)-1-(1H-1,2,4-triazol-1-yl)butan-2-ol,
92) (2R,3R)-2-(2,4-difluorophenyl)-3-((1-(3-fluorophenyl)piperidin-4-yl)oxy)-1-(1H-1,2,4-triazol-1-yl)butan-2-ol,
93) (2R,3R)-2-(2,4-difluorophenyl)-3-((1-(4-fluorophenyl)piperidin-4-yl)oxy)-1-(1H-1,2,4-triazol-1-yl)butan-2-ol,
94) (2R,3R)-3-((1-(2-bromophenyl)piperidin-4-yl)oxy)-2-(2,4-difluorophenyl)-1-(1H-1,2,4-triazol-1-yl)butan-2-ol,
95) (2R,3R)-3-((1-(3-chlorophenyl)piperidin-4-yl)oxy)-2-(2,4-difluorophenyl)-1-(1H-1,2,4-triazol-1-yl)butan-2-ol,
96) (2R,3R)-3-((1-(4-chlorophenyl)piperidin-4-yl)oxy)-2-(2,4-difluorophenyl)-1-(1H-1,2,4-triazol-1-yl)butan-2-ol,
97) (2R,3R)-3-((1-(2-bromophenyl)piperidin-4-yl)amino)-2-(2,4-difluorophenyl)-1-(1H-1,2,4-triazol-1-yl)butan-2-ol,
98) (2R,3R)-3-((1-(3-bromophenyl)piperidin-4-yl)oxy)-2-(2,4-difluorophenyl)-1-(1H-1,2,4-triazol-1-yl)butan-2-ol,
99) (2R,3R)-3-((1-(4-bromophenyl)piperidin-4-yl)oxy)-2-(2,4-difluorophenyl)-1-(1H-1,2,4-triazol-1-yl)butan-2-ol,
100) (2R,3R)-2-(2,4-difluorophenyl)-1-(1H-1,2,4-triazol-1-yl)-3-((1-(2-(trifluoromethyl)phenyl)piperidin-4-yl)oxy)butan-2-ol,
101) (2R,3R)-2-(2,4-difluorophenyl)-1-(1H-1,2,4-triazol-1-yl)-3-((1-(3-(trifluoromethyl)phenyl)piperidin-4-yl)oxy)butan-2-ol,
102) (2R,3R)-2-(2,4-difluorophenyl)-1-(1H-1,2,4-triazol-1-yl)-3-((1-(4-(trifluoromethyl)phenyl)piperidin-4-yl)oxy)butan-2-ol,
103) 2-(4-(((2R,3R)-3-(2,4-difluorophenyl)-3-hydroxy-4-(1H-1,2,4-triazol-1-yl)butan-2-yl)oxy)piperidin-1-yl)benzonitrile,
104) 3-(4-(((2R,3R)-3-(2,4-difluorophenyl)-3-hydroxy-4-(1H-1,2,4-triazol-1-yl)butan-2-yl)oxy)piperidin-1-yl)benzonitrile,
105) 4-(4-(((2R,3R)-3-(2,4-difluorophenyl)-3-hydroxy-4-(1H-1,2,4-triazol-1-yl)butan-2-yl)oxy)piperidin-1-yl)benzonitrile, 106) (2R,3R)-3-((1-(2,4-dichlorophenyl)piperidin-4-yl)oxy)-2-(2,4-difluorophenyl)-1-(1H-1,2,4-triazol-1-yl)butan-2-ol,
107) (2R,3R)-3-((1-(3,4-dichlorophenyl)piperidin-4-yl)oxy)-2-(2,4-difluorophenyl)-1-(1H-1,2,4-triazol-1-yl)butan-2-ol,
108) (2R,3R)-3-((1-(4-chloro-2-fluorophenyl)piperidin-4-yl)oxy)-2-(2,4-difluorophenyl)-1-(1H-1,2,4-triazol-1-yl)butan-2-ol,
109) (2R,3R)-2-(2,4-difluorophenyl)-3-((1-(2,4-difluorophenyl)piperidin-4-yl)oxy)-1-(1H-1,2,4-triazol-1-yl)butan-2-ol,
110) (2R,3R)-3-((1-(4-chloro-3-fluorophenyl)piperidin-4-yl)oxy)-2-(2,4-difluorophenyl)-1-(1H-1,2,4-triazol-1-yl)butan-2-ol,
111) (2R,3R)-3-((1-(4-chloro-2-methylphenyl)piperidin-4-yl)oxy)-2-(2,4-difluorophenyl)-1-(1H-1,2,4-triazol-1-yl)butan-2-ol,
112) (2R,3R)-2-(2,4-difluorophenyl)-3-((1-(pyridin-2-yl)piperidin-4-yl)oxy)-1-(1H-1,2,4-triazol-1-yl)butan-2-ol,
113) (2R,3R)-2-(2,4-difluorophenyl)-3-((1-(5-methylpyridin-2-yl)piperidin-4-yl)oxy)-1-(1H-1,2,4-triazol-1-yl)butan-2-ol,
114) (2R,3R)-2-(2,4-difluorophenyl)-3-((1-(5-fluoropyridin-2-yl)piperidin-4-yl)oxy)-1-(1H-1,2,4-triazol-1-yl)butan-2-ol,
115) (2R,3R)-3-((1-(5-chloropyridin-2-yl)piperidin-4-yl)oxy)-2-(2,4-difluorophenyl)-1-(1H-1,2,4-triazol-1-yl)butan-2-ol,
116) (2R,3R)-2-(2,4-difluorophenyl)-3-((1-(3-methyl-5-(trifluoromethyl)pyridin-2-yl)piperidin-4-yl)oxy)-1-(1H-1,2,4-triazol-1-yl)butan-2-ol,
117) (2R,3R)-2-(2,4-difluorophenyl)-3-((1-(5-methylpyrimidin-2-yl)piperidin-4-yl)oxy)-1-(1H-1,2,4-triazol-1-yl)butan-2-ol,
118) (2R,3R)-2-(2,4-difluorophenyl)-3-((1-(5-fluoropyrimidin-2-yl)piperidin-4-yl)oxy)-1-(1H-1,2,4-triazol-1-yl)butan-2-ol,
119) (2R,3R)-3-((1-(5-chloropyrimidin-2-yl)piperidin-4-yl)oxy)-2-(2,4-difluorophenyl)-1-(1H-1,2,4-triazol-1-yl)butan-2-ol,
120) (2R,3R)-3-((1-(5-bromopyrimidin-2-yl)piperidin-4-yl)oxy)-2-(2,4-difluorophenyl)-1-(1H-1,2,4-triazol-1-yl)butan-2-ol,
121) (2R,3R)-2-(2,4-difluorophenyl)-1-(1H-1,2,4-triazol-1-yl)-3-((1-(4-(trifluoromethyl)pyrimidin-2-yl)piperidin-4-yl)oxy)butan-2-ol,
122) (2R,3R)-2-(2,4-difluorophenyl)-3-((1-(2-fluorophenyl)piperidin-4-yl)amino)-1-(1H-1,2,4-triazol-1-yl)butan-2-ol,
123) (2R,3R)-2-(2,4-difluorophenyl)-3-((1-phenylpiperidin-4-yl)amino)-1-(1H-1,2,4-triazol-1-yl)butan-2-ol,
124) (2R,3R)-2-(2,4-difluorophenyl)-3-((1-(3-fluorophenyl)piperidin-4-yl)amino)-1-(1H-1,2,4-triazol-1-yl)butan-2-ol,
125) (2R,3R)-2-(2,4-difluorophenyl)-3-((1-(4-fluorophenyl)piperidin-4-yl)amino)-1-(1H-1,2,4-triazol-1-yl)butan-2-ol,
126) (2R,3R)-3-((1-(2-chlorophenyl)piperidin-4-yl)amino)-2-(2,4-difluorophenyl)-1-(1H-1,2,4-triazol-1-yl)butan-2-ol,
127) (2R,3R)-3-((1-(3-chlorophenyl)piperidin-4-yl)amino)-2-(2,4-difluorophenyl)-1-(1H-1,2,4-triazol-1-yl)butan-2-ol,
128) (2R,3R)-3-((1-(4-chlorophenyl)piperidin-4-yl)amino)-2-(2,4-difluorophenyl)-1-(1H-1,2,4-triazol-1-yl)butan-2-ol,
129) (2R,3R)-3-((1-(2-bromophenyl)piperidin-4-yl)amino)-2-(2,4-difluorophenyl)-1-(1H-1,2,4-triazol-1-yl)butan-2-ol,
130) (2R,3R)-3-((1-(3-bromophenyl)piperidin-4-yl)amino)-2-(2,4-difluorophenyl)-1-(1H-1,2,4-triazol-1-yl)butan-2-ol,
131) (2R,3R)-3-((1-(4-bromophenyl)piperidin-4-yl)amino)-2-(2,4-difluorophenyl)-1-(1H-1,2,4-triazol-1-yl)butan-2-ol,
132) (2R,3R)-2-(2,4-difluorophenyl)-1-(1H-1,2,4-triazol-1-yl)-3-((1-(2-(trifluoromethyl)phenyl)piperidin-4-yl)amino)butan-2-ol,
133) (2R,3R)-2-(2,4-difluorophenyl)-1-(1H-1,2,4-triazol-1-yl)-3-((1-(3-(trifluoromethyl)phenyl)piperidin-4-yl)amino)butan-2-ol,
134) (2R,3R)-2-(2,4-difluorophenyl)-1-(1H-1,2,4-triazol-1-yl)-3-((1-(4-(trifluoromethyl)phenyl)piperidin-4-yl)amino)butan-2-ol,
135) 2-(4-(((2R,3R)-3-(2,4-difluorophenyl)-3-hydroxy-4-(1H-1,2,4-triazol-1-yl)butan-2-yl)amino)piperidin-1-yl)benzonitrile,
136) 3-(4-(((2R,3R)-3-(2,4-difluorophenyl)-3-hydroxy-4-(1H-1,2,4-triazol-1-yl)butan-2-yl)amino)piperidin-1-yl)benzonitrile,
137) 4-(4-(((2R,3R)-3-(2,4-difluorophenyl)-3-hydroxy-4-(1H-1,2,4-triazol-1-yl)butan-2-yl)amino)piperidin-1-yl)benzonitrile,
138) (2R,3R)-3-((1-(2,4-dichlorophenyl)piperidin-4-yl)amino)-2-(2,4-difluorophenyl)-1-(1H-1,2,4-triazol-1-yl)butan-2-ol,
139) (2R,3R)-3-((1-(3,4-dichlorophenyl)piperidin-4-yl)amino)-2-(2,4-difluorophenyl)-1-(1H-1,2,4-triazol-1-yl)butan-2-ol,
140) (2R,3R)-3-((1-(4-chloro-2-fluorophenyl)piperidin-4-yl)amino)-2-(2,4-difluorophenyl)-1-(1H-1,2,4-triazol-1-yl)butan-2-ol,
141) (2R,3R)-2-(2,4-difluorophenyl)-3-((1-(2,4-difluorophenyl)piperidin-4-yl)amino)-1-(1H-1,2,4-triazol-1-yl)butan-2-ol,
142) (2R,3R)-3-((1-(4-chloro-3-fluorophenyl)piperidin-4-yl)amino)-2-(2,4-difluorophenyl)-1-(1H-1,2,4-triazol-1-yl)butan-2-ol,
143) (2R,3R)-3-((1-(4-chloro-2-methylphenyl)piperidin-4-yl)amino)-2-(2,4-difluorophenyl)-1-(1H-1,2,4-triazol-1-yl)butan-2-ol,
144) (2R,3R)-2-(2,4-difluorophenyl)-3-((1-(pyridin-2-yl)piperidin-4-yl)amino)-1-(1H-1,2,4-triazol-1-yl)butan-2-ol,
145) (2R,3R)-2-(2,4-difluorophenyl)-3-((1-(5-methylpyridin-2-yl)piperidin-4-yl)amino)-1-(1H-1,2,4-triazol-1-yl)butan-2-ol,
146) (2R,3R)-2-(2,4-difluorophenyl)-3-((1-(5-fluoropyridin-2-yl)piperidin-4-yl)amino)-1-(1H-1,2,4-triazol-1-yl)butan-2-ol,
147) (2R,3R)-3-((1-(5-chloropyridin-2-yl)piperidin-4-yl)amino)-2-(2,4-difluorophenyl)-1-(1H-1,2,4-triazol-1-yl)butan-2-ol,
148) (2R,3R)-2-(2,4-difluorophenyl)-3-((1-(3-methyl-5-(trifluoromethyl)pyridin-2-yl)piperidin-4-yl)amino)-1-(1H-1,2,4-triazol-1-yl)butan-2-ol,
149) (2R,3R)-2-(2,4-difluorophenyl)-3-((1-(pyrimidin-2-yl)piperidin-4-yl)amino)-1-(1H-1,2,4-triazol-1-yl)butan-2-ol, 150) (2R,3R)-2-(2,4-difluorophenyl)-3-((1-(5-methylpyrimidin-2-yl)piperidin-4-yl)amino)-1-(1H-1,2,4-triazol-1-yl)butan-2-ol,
151) (2R,3R)-2-(2,4-difluorophenyl)-3-((1-(5-fluoropyrimidin-2-yl)piperidin-4-yl)amino)-1-(1H-1,2,4-triazol-1-yl)butan-2-ol,
152) (2R,3R)-3-((1-(5-chloropyrimidin-2-yl)piperidin-4-yl)amino)-2-(2,4-difluorophenyl)-1-(1H-1,2,4-triazol-1-yl)butan-2-ol,
153) (2R,3R)-3-((1-(5-bromopyrimidin-2-yl)piperidin-4-yl)amino)-2-(2,4-difluorophenyl)-1-(1H-1,2,4-triazol-1-yl)butan-2-ol,
154) (2R,3R)-2-(2,4-difluorophenyl)-1-(1H-1,2,4-triazol-1-yl)-3-((1-(4-(trifluoromethyl)pyrimidin-2-yl)piperidin-4-yl)amino)butan-2-ol,
155) (2R,3R)-2-(2,4-difluorophenyl)-3-(methyl(1-phenylpiperidin-4-yl)amino)-1-(1H-1,2,4-triazol-1-yl)butan-2-ol,
156) (2R,3R)-2-(2,4-difluorophenyl)-3-((1-(2-fluorophenyl)piperidin-4-yl)(methyl)amino)-1-(1H-1,2,4-triazol-1-yl)butan-2-ol,
157) (2R,3R)-2-(2,4-difluorophenyl)-3-((1-(3-fluorophenyl)piperidin-4-yl)(methyl)amino)-1-(1H-1,2,4-triazol-1-yl)butan-2-ol,
158) (2R,3R)-2-(2,4-difluorophenyl)-3-((1-(4-fluorophenyl)piperidin-4-yl)(methyl)amino)-1-(1H-1,2,4-triazol-1-yl)butan-2-ol,
159) (2R,3R)-3-((1-(2-chlorophenyl)piperidin-4-yl)(methyl)amino)-2-(2,4-difluorophenyl)-1-(1H-1,2,4-triazol-1-yl)butan-2-ol,
160) (2R,3R)-3-((1-(3-chlorophenyl)piperidin-4-yl)(methyl)amino)-2-(2,4-difluorophenyl)-1-(1H-1,2,4-triazol-1-yl)butan-2-ol,
161) (2R,3R)-3-((1-(4-chlorophenyl)piperidin-4-yl)(methyl)amino)-2-(2,4-difluorophenyl)-1-(1H-1,2,4-triazol-1-yl)butan-2-ol,
162) (2R,3R)-3-((1-(2-bromophenyl)piperidin-4-yl)(methyl)amino)-2-(2,4-difluorophenyl)-1-(1H-1,2,4-triazol-1-yl)butan-2-ol,
163) (2R,3R)-3-((1-(3-bromophenyl)piperidin-4-yl)(methyl)amino)-2-(2,4-difluorophenyl)-1-(1H-1,2,4-triazol-1-yl)butan-2-ol,
164) (2R,3R)-3-((1-(4-bromophenyl)piperidin-4-yl)(methyl)amino)-2-(2,4-difluorophenyl)-1-(1H-1,2,4-triazol-1-yl)butan-2-ol,
165) (2R,3R)-2-(2,4-difluorophenyl)-3-(methyl(1-(2-(trifluoromethyl)phenyl)piperidin-4-yl)amino)-1-(1H-1,2,4-triazol-1-yl)butan-2-ol,
166) (2R,3R)-2-(2,4-difluorophenyl)-3-(methyl(1-(3-(trifluoromethyl)phenyl)piperidin-4-yl)amino)-1-(1H-1,2,4-triazol-1-yl)butan-2-ol,
167) (2R,3R)-2-(2,4-difluorophenyl)-3-(methyl(1-(4-(trifluoromethyl)phenyl)piperidin-4-yl)amino)-1-(1H-1,2,4-triazol-1-yl)butan-2-ol,
168) 2-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
169) 3-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
170) 4-(4-(((2R,3R)-3-(2,4-difluorophenyl)-3-hydroxy-4-(1H-1,2,4-triazol-1-yl)butan-2-yl)(methyl)amino)piperidin-1-yl)benzonitrile,
171) (2R,3R)-3-((1-(2,4-dichlorophenyl)piperidin-4-yl)(methyl)amino)-2-(2,4-difluorophenyl)-1-(1H-1,2,4-triazol-1-yl)butan-2-ol,
172) (2R,3R)-3-((1-(3,4-dichlorophenyl)piperidin-4-yl)(methyl)amino)-2-(2,4-difluorophenyl)-1-(1H-1,2,4-triazol-1-yl)butan-2-ol,
173) (2R,3R)-3-((1-(4-chloro-2-fluorophenyl)piperidin-4-yl)(methyl)amino)-2-(2,4-difluorophenyl)-1-(1H-1,2,4-triazol-1-yl)butan-2-ol,
174) (2R,3R)-2-(2,4-difluorophenyl)-3-((1-(2,4-difluorophenyl)piperidin-4-yl)(methyl)amino)-1-(1H-1,2,4-triazol-1-yl)butan-2-ol,
175) (2R,3R)-3-((1-(4-chloro-3-fluorophenyl)piperidin-4-yl)(methyl)amino)-2-(2,4-difluorophenyl)-1-(1H-1,2,4-triazol-1-yl)butan-2-ol,
176) (2R,3R)-3-((1-(4-chloro-2-methylphenyl)piperidin-4-yl)(methyl)amino)-2-(2,4-difluorophenyl)-1-(1H-1,2,4-triazol-1-yl)butan-2-ol,
177) (2R,3R)-2-(2,4-difluorophenyl)-3-((1-phenylpiperidin-3-yl)amino)-1-(1H-1,2,4-triazol-1-yl)butan-2-ol,
178) (2R,3R)-2-(2,4-difluorophenyl)-3-(3-(phenylamino)pyrrolidin-1-yl)-1-(1H-1,2,4-triazol-1-yl)butan-2-ol,
179) (2R,3R)-3-((R)-3-(4-chlorophenoxy)pyrrolidin-1-yl)-2-(2,4-difluorophenyl)-1-(1H-1,2,4-triazol-1-yl)butan-2-ol, and
180) (2R,3R)-3-((S)-3-(4-chlorophenoxy)pyrrolidin-1-yl)-2-(2,4-difluorophenyl)-1-(1H-1,2,4-triazol-1-yl)butan-2-ol.

8. A method for the preparation of a compound represented by Chemical Formula 1, comprising reacting a compound represented by Chemical Formula 2 having the following structure with a compound represented by Chemical Formula 3a, 3b, 3c or 3d each having the following structures:

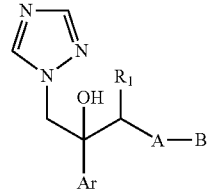

[Chemical Formula 1]

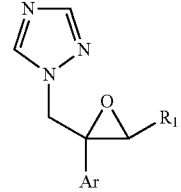

[Chemical Formula 2]

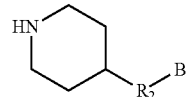

[Chemical Formula 3a]

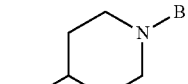

[Chemical Formula 3b]

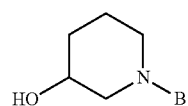

[Chemical Formula 3c]

-continued

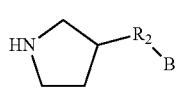
[Chemical Formula 3d]

wherein, in the Chemical Formulae 1, 2, 3a, 3b, 3c and 3d,
A is

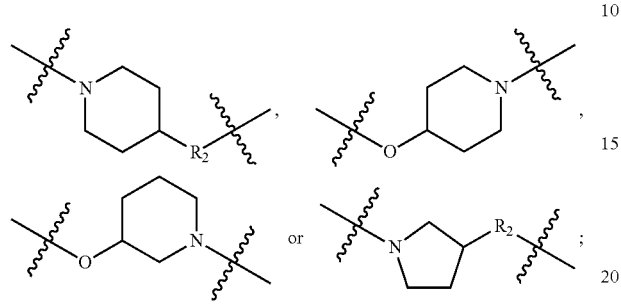

Ar is phenyl which is substituted with one to five halogens;
B is phenyl, pyridinyl or pyrimidinyl, which is unsubstituted or substituted with one or two $R_3$ groups;
$R_1$ is hydrogen or $C_{1-4}$ alkyl;
$R_2$ is O, NH or $NCH_3$; and
$R_3$ is independently halogen, $C_{1-4}$ alkyl, $C_{1-4}$ haloalkyl or cyano.

9. The method according to claim 8, wherein the molar ratio of the compound represented by Chemical Formula 2 and the compound represented by Chemical Formula 3a, 3b, 3c or 3d is 1:1 to 1:3.

10. The method according to claim 8, wherein the reaction is performed in a basic condition.

11. The method according to claim 10, wherein sodium hydride, calcium carbonate sodium methoxide, triethylamine, or 1,8-diazabicyclo[5,4,0]undec-7-ene(DBU) is used for the basic condition.

12. The method according to claim 8, wherein the reaction is performed under an acid catalyst selected from the group consisting of lithium perchlorate, sodium perchlorate, potassium perchlorate, and cesium perchlorate.

13. A method for the preparation of a compound represented by Chemical Formula 1, comprising reacting a compound represented by Chemical Formula 4 having the following structure with a compound represented by Chemical Formula 5a or 5b each having the following structures:

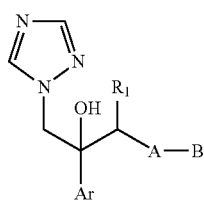
[Chemical Formula 1]

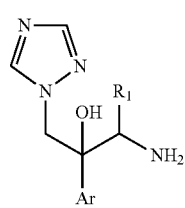
[Chemical Formula 4]

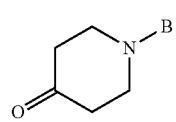
[Chemical Formula 5a]

[Chemical Formula 5b]

wherein, in the Chemical Formulae 1, 4, 5a and 5b,
A is

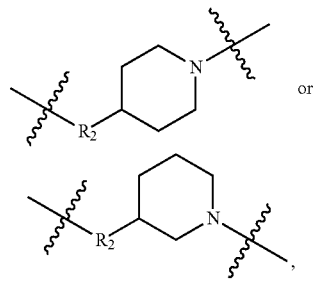

Ar is phenyl which is substituted with one to five halogens;
B is phenyl, pyridinyl or pyrimidinyl, which is unsubstituted or substituted with one or two $R_3$ groups;
$R_1$ is hydrogen or $C_{1-4}$ alkyl;
$R_2$ is NH;
$R_3$ is independently halogen, $C_{1-4}$ alkyl, $C_{1-4}$ haloalkyl, or cyano.

14. The method according to claim 13, wherein the molar ratio of the compound represented by Chemical Formula 4 and the compound represented by Chemical Formula 5a or 5b is 1:0.5 to 1:2.

15. The method according to claim 14, wherein the reaction is performed by using titanium (IV) isopropoxide in the presence of a reducing agent selected from the group consisting of sodium cyanoborohydride, sodium triacetoxyborohydride and borane-pyridine.

16. A method for the preparation of a compound represented by Chemical Formula 1, comprising reacting a compound represented by Chemical Formula 1e or 1f having the following structures with a compound represented by Chemical Formula 6 having the following structure:

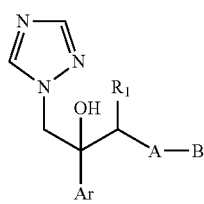
[Chemical Formula 1]

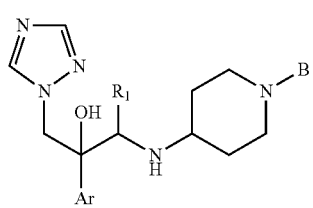
[Chemical Formula 1e]

[Chemical Formula 1f]

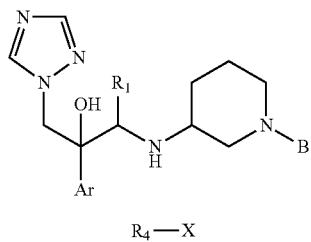

[Chemical Formula 6]

R₄—X wherein, in the Chemical Formulae 1, 1e, 1f, and 6,
Ar is phenyl which is substituted with one to five halogens;
B is phenyl, pyridinyl or pyrimidinyl, which is unsubstituted or substituted with one or two $R_3$ groups;
A is

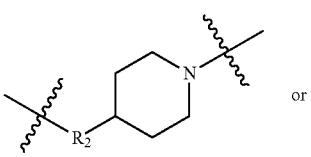 or

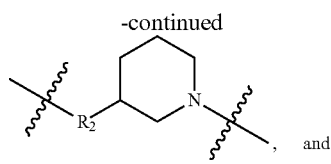, and $R_1$ is hydrogen or $C_{1-4}$ alkyl;
$R_2$ is $NCH_3$,
$R_3$ is independently halogen, $C_{1-4}$ alkyl, $C_{1-4}$ haloalkyl or cyano;
$R_4$ is $CH_3$, and
X is halogen.

17. A antifungal composition comprising the compound or the pharmaceutically acceptable salt of claim 1.

18. A method for treatment of fungal infections in a subject in need thereof, comprising administering to the subject a therapeutically effective amount of the compound or the pharmaceutically acceptable salt of claim 1.

* * * * *

UNITED STATES PATENT AND TRADEMARK OFFICE
CERTIFICATE OF CORRECTION

Page 1 of 1

PATENT NO. : 8,940,768 B2
APPLICATION NO. : 13/578590
DATED : January 27, 2015
INVENTOR(S) : Joon Seok Park et al.

It is certified that error appears in the above-identified patent and that said Letters Patent is hereby corrected as shown below:

Claims

Column 52, Line 42, claim 7
"19) (2R,3R)-3-(4-(3-bromophenoxy)piperidin-1-yl)-2-(2,4-difluorophenyl)-1-(1H-1,2,4-triazol-1-yl)butan-2-ol," should read, --9) (2R,3R)-3-(4-(3-bromophenoxy)piperidin-1-yl)-2-(2,4-difluorophenyl)-1-(1H-1,2,4-triazol-1-yl)butan-2-ol,--.

Signed and Sealed this
Eighth Day of December, 2015

Michelle K. Lee
*Director of the United States Patent and Trademark Office*